(12) United States Patent
Zeng et al.

(10) Patent No.: US 11,857,648 B2
(45) Date of Patent: Jan. 2, 2024

(54) DIMERIZATION STRATEGIES AND COMPOUNDS FOR MOLECULAR IMAGING AND/OR RADIOIMMUNOTHERAPY

(71) Applicant: UNIVERSITY OF PITTSBURGH—OF THE COMMONWEALTH SYSTEM OF HIGHER EDUCATION, Pittsburgh, PA (US)

(72) Inventors: Dexing Zeng, Portland, OR (US); Lingyi Sun, Pittsburgh, PA (US); Yongkang Gai, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 16/179,817

(22) Filed: Nov. 2, 2018

(65) Prior Publication Data

US 2019/0134240 A1 May 9, 2019

Related U.S. Application Data

(63) Continuation of application No. PCT/US2017/030662, filed on May 2, 2017.

(60) Provisional application No. 62/373,036, filed on Aug. 10, 2016, provisional application No. 62/346,783, filed on Jun. 7, 2016, provisional application No. 62/330,622, filed on May 2, 2016.

(51) Int. Cl.

| | | |
|---|---|---|
| *A61K 51/08* | (2006.01) | |
| *C07K 16/30* | (2006.01) | |
| *C07K 7/06* | (2006.01) | |
| *C07K 7/64* | (2006.01) | |
| *G01N 33/50* | (2006.01) | |
| *G01N 33/60* | (2006.01) | |
| *A61K 51/10* | (2006.01) | |
| *A61K 47/68* | (2017.01) | |
| *C07D 255/02* | (2006.01) | |
| *C07D 257/02* | (2006.01) | |
| *A61K 9/51* | (2006.01) | |

(52) U.S. Cl.
CPC ............ *A61K 51/082* (2013.01); *A61K 9/51* (2013.01); *A61K 47/6893* (2017.08); *A61K 51/1027* (2013.01); *C07D 255/02* (2013.01); *C07D 257/02* (2013.01); *C07K 7/06* (2013.01); *C07K 7/64* (2013.01); *C07K 16/30* (2013.01); *G01N 33/5008* (2013.01); *G01N 33/60* (2013.01); *C07K 2319/00* (2013.01)

(58) Field of Classification Search
CPC ...... A61K 51/00; A61K 51/082; A61K 51/04; A61K 51/1027; A61K 2121/00; C07D 257/02; C07D 255/02; C07K 7/64; C07K 7/06; C07K 16/30; G01N 33/60; G01N 33/5008
USPC .......... 424/1.11, 1.49, 1.65, 1.69, 1.73, 1.81, 424/1.85, 1.89, 9.1; 534/7, 10–16; 530/300; 514/1, 1.1

See application file for complete search history.

(56) References Cited

U.S. PATENT DOCUMENTS

| | | | |
|---|---|---|---|
| 6,656,448 | B1 | 12/2003 | Carpenter, Jr. et al. |
| 7,666,979 | B2 * | 2/2010 | Fan .................... A61K 49/0043 530/331 |
| 2005/0059101 | A1 | 3/2005 | Ringold |
| 2005/0130167 | A1 | 6/2005 | Bao et al. |
| 2009/0202435 | A1 | 8/2009 | Port |
| 2010/0196271 | A1 | 8/2010 | Conti et al. |
| 2011/0280801 | A1 | 11/2011 | McBride et al. |
| 2013/0122516 | A1 | 5/2013 | Hong et al. |
| 2015/0125904 | A1 | 5/2015 | Ting et al. |
| 2015/0132219 | A1 | 5/2015 | Kjaer et al. |

FOREIGN PATENT DOCUMENTS

| | | |
|---|---|---|
| WO | WO 2009/135015 A2 | 11/2009 |
| WO | WO 2011/045394 A1 | 4/2011 |

OTHER PUBLICATIONS

Liu et al, J. Med. Chem., vol. 52, No. 2, pp. 425-432 (Year: 2009).*
Oliveira et al, Melanoma Research, vol. 22, No. 1, pp. 45-53 (Year: 2012).*
Schweinsberg et al., Bioconjugate Chemistry, vol. 19, No. 12, pp. 2432-2439. (Year: 2008).*
Gai et al (Journal of Nuclear Medicine, May 15, 2015, vol. 56, Supplement 3, Abstract No. 1053). (Year: 2015).*
Yim, Thesis: Synthesis and Evaluation of Radiolabeled Peptide Multimers for Tumor Targeting, 169 pages (Year: 2011).*
Gai et al (Bioconjugate Chemistry, Feb. 18, 2016, vol. 27, pp. 515-520). (Year: 2016).*
U.S. Appl. No. 16/179,785, filed Nov. 2, 2018.
Ali et al., "Simultaneous targeting of the epidermal growth factor receptor and cyclooxygenase-2 pathways for pancreatic cancer therapy," Molecular Cancer Therapeutics 4(12):1943-1951 (2005).
Ariyama et al., "Imaging of Small Pancreatic Ductal Adenocarcinoma," Pancreas 16(3):396-401 (1998).

(Continued)

*Primary Examiner* — D. L. Jones
(74) *Attorney, Agent, or Firm* — Baker Botts L.L.P.

(57) ABSTRACT

The present invention provides a multivalent compound for targeted molecular imaging and/or targeted drug delivery, wherein two components or targeting molecules each interacts with one or more biomarkers on a cell. The present invention further provides a multifunctional chelator to combine the targeting molecules. The present invention also provides an in vitro high-throughput screening assay to determine the length of the spacer molecules. The present invention also relates to compounds/probes, kits and methods for use in targeted molecular imaging and/or targeted drug delivery.

8 Claims, 27 Drawing Sheets

Figure 1:
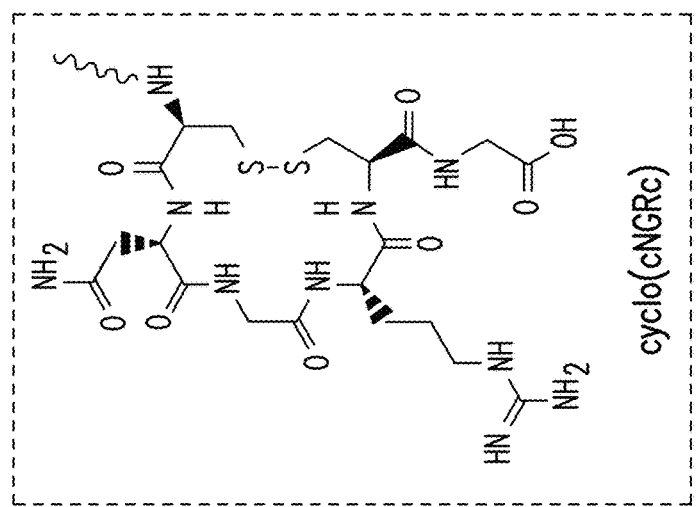
Figure 1:
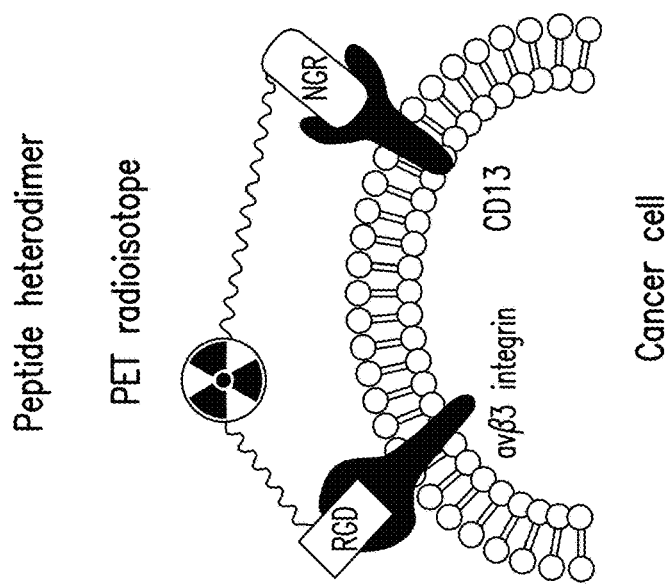
Figure 1:
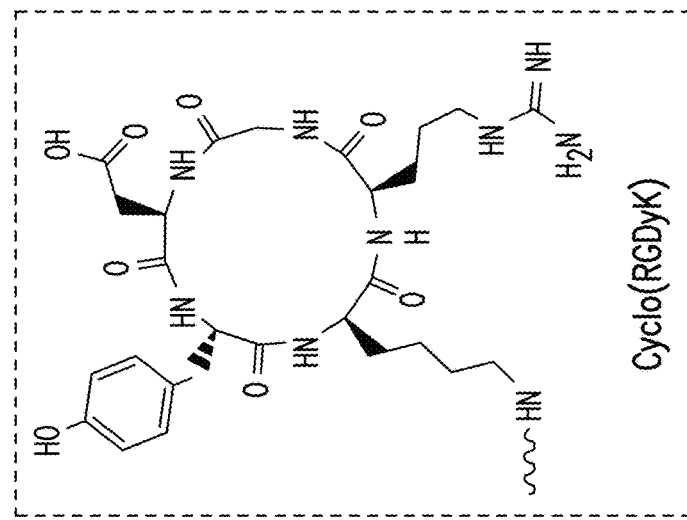

Specification includes a Sequence Listing.

(56) References Cited

OTHER PUBLICATIONS

Brooks, "Role of Integrins in Angiogenesis," European Journal of Cancer 32A(14):2423-2429 (1996).
Brooks et al., "Requirement of Vascular Integrin αvβ3 for Angiogenesis," Science 264:569-571 (1994).
Carroll et al., "Bioorthogonal chemistry for pre-targeted molecular imaging-progress and prospects," Organic & Biomolecular Chemistry 11:5772-5781 (2013).
Cascinu et al., "Cetuximab plus gemcitabine and cisplatin compared with gemcitabine and cisplatin alone in patients with advanced pancreatic cancer: a randomised, multicentre, phase II trial," Lancet Oncol 9:39-44 (2008).
Castanon et al., "Epidermal Growth Factor Receptor Targeting in Non-Small Cell Lung Cancer: Revisiting Different Strategies Against the Same Target," Current Drug Targets 15:1273-1283 (2014).
Chang et al., "Development and Characterization of (89)Zr-Labeled Panitumumab for Immuno-Positron Emission Tomographic Imaging of the Epidermal Growth Factor Receptor," Molecular Imaging 12:17-27 (2013).
Chen et al., "Clinical Application of Radiolabeled RGD Peptides for PET Imaging of Integrin αvβ3," Theranostics 6:78-92 (2016).
Ciardiello et al., "EGFR Antagonists in Cancer Treatment," N Engl. J Med 358:1160-1174 (2008).
Cohen et al., "Inert coupling of IRDye800CW to monoclonal antibodies for clinical optical imaging of tumor targets," EJNMMI Research 1:31 (2011), 13 pages.
Deri et al., "PET Imaging with 89Zr: From Radiochemistry to the Clinic," Nucl Med Biol 40:3-14 (2013).
Desgrosellier et al., "Integrins in cancer: biological implications and therapeutic opportunities," Nature Reviews Cancer 10:9-22 (2010).
Egawa et al., "Clinicopathological Aspects of Small Pancreatic Cancer," Pancreas 28:235-240 (2004).
Evans et al., "A bioorthogonal (68)Ga-labelling strategy for rapid in vivo imaging," Chemical Communications 50:9557-9560 (2014).
Gai et al., "Novel TACN chelator: a scaffold designed for dual-receptor targeted PET imaging," Journal of Nuclear Medicine 56(3):1053 (2015).
Ghadirian et al., "Epidemiology of pancreatic cancer: an overview," Cancer Detection and Prevention 27:87-93 (2003).
Girgis et al., "CA19-9 as a Potential Target for Radiolabeled Antibody-Based Positron Emission Tomography of Pancreas Cancer," International Journal of Molecular Imaging Article ID 834515, 9 pages (2011).
Goggins, "Identifying Molecular Markers for the Early Detection of Pancreatic Neoplasia," Seminars in Oncology 34:303-310 (2007).
Goldenberg et al., "Radioimmunodetection in Cancer Identification," Journal of Nuclear Medicine 33:803-814 (1992).
Goldenberg, "Cancer Imaging with CEA antibodies: historical and current perspectives," The International Journal of Biological Markers 7(3):183-188 (1992).
Goldenberg et al., "Pretargeted Molecular Imaging and Radioimmunotherapy," Theranostics 2(5):523-540 (2012).
Goldenberg et al., "Use of RadioLabeled Antibodies to Carcinoembryonic Antigen for the Detection and Localization of Diverse Cancers by External Photoscanning," The New England Journal of Medicine 298(25):1384-1388 (1978).
Goodwin et al., "Pre-Targeted Immunoscintigraphy of Murine Tumors with Indium-111-Labeled Bifunctional Haptens," Journal of Nuclear Medicine 29:226-234 (1988).
Goodwin et al., "Monoclonal antibody hapten radiopharmaceutical delivery," Nuclear Medicine Communications 7:569-580 (1986).
Haubner et al., "Noninvasive Visualization of the Activated αvβ3 Integrin in Cancer Patients by Positron Emission Tomography and [18F]Galacto-RGD," PLoS Medicine 2(3):e70 (2005).
Hosotani et al., "Expression of Integrin αVβ3 in Pancreatic Carcinoma: Relation to MMP-2 Activation and Lymph Node Metastasis," Pancreas 25(2):e30-e35 (2002).
Hutchinson, "Imaging: PET is prognostic of survival in pancreatic cancer patients," Nat Rev Clin Oncol 7:551 (2010).
Hynes et al., "ERBB Receptors and Cancer: The Complexity of Targeted Inhibitors," Nature Reviews, Cancer 5:341-354 (2005).
International Search Report dated Sep. 25, 2017 in International Application No. PCT/US17/30652.
International Search Report dated Sep. 25, 2017 in International Application No. PCT/US17/30662.
Kelly et al., "Targeted Nanoparticles for Imaging Incipient Pancreatic Ductal Adenocarcinoma," PLoS Medicine 5(4):e85 (2008).
Knight et al., "Bioorthogonal chemistry: implications for pretargeted nuclear (PET/SPECT) imaging and therapy," American Journal of Nuclear Medicine and Molecular Imaging 4(2):96-113 (2014).
Kubas et al., "Multivalent cyclic RGD ligands: influence of linker lengths on receptor binding," Nucl Med Biol 37:885-891 (2010).
Lamberts et al., "Antibody Positron Emission Tomography Imaging in Anticancer Drug Development," Journal of Clinical Oncology 33:1491-1504 (2015).
Larson et al., "PET Scanning of Iodine-124-3F9 as an Approach to Tumor Dosimetry during Treatment Planning for Radioimmunotherapy in a Child with Neuroblastoma," Journal of Nuclear Medicine 33:2020-2023 (1992).
Li et al., "(64)Cu-Labeled Tetrameric and Octameric Rgd Peptides for Small-Animal PET of Tumor α(v)β(3) Integrin Expression," Journal of Nuclear Medicine 48:1162-1171 (2007).
Lurje et al., "EGFR Signaling and Drug Discovery," Oncology 77:400-410 (2009).
McNitt et al., "Photochemical generation of oxa-dibenzocyclooctyne (ODIBO) for metal-free click ligations," Org. Biomol. Chem. 10:8200-8202 (2012).
Mendelsohn et al., "Epidermal Growth Factor Receptor Targeting in Cancer," Seminars in Oncology 33:369-385 (2006).
Menke-van der Houven van Oordt et al., "(89)Zr-cetuximab PET imaging in patients with advanced colorectal cancer," Oncotarget 6(30):30384-30393 (2015).
Meyer et al., "(18)F-Based Pretargeted PET Imaging Based on Bioorthogonal Diels-Alder Click Chemistry," Bioconjugate Chemistry 27:298-301 (2016).
Michaud, "Epidemiology of Pancreatic Cancer," Minerva Chir 59(2):99-111 (2004).
Mizejewski, "Role of Integrins in Cancer: Survey of Expression Patterns," Proceedings of the Society for Experimental Biology and Medicine 222:124-138 (1999).
Neoptolemos et al., "A Randomized Trial of Chemoradiotherapy and Chemotherapy after Resection of Pancreatic Cancer," N Engl. J Med 350:1200-1210 (2004).
Persson et al., "First-in-human uPAR PET: Imaging of Cancer Aggressiveness," Theranostics 5(12):1303-1316 (2015).
Pfeifer et al., "Clinical PET of Neuroendocrine Tumors Using (64)Cu-Dotatate: First-in-Humans Study," Journal of Nuclear Medicine 53:1207-1215 (2012).
Li et al., "Receptor-binding, biodistribution, and metabolism studies of 64Cu-DOTA-cetuximab, a PET-imaging agent for epidermal growth-factor receptor-positive tumors," Cancer Biotherapy & Radiopharmaceuticals 23:158-171 (2008).
Reardan et al., "Antibodies against metal chelates," Nature 316:265-268 (1985).
Robinson et al., "Quantitative Immuno-Positron Emission Tomography Imaging of HER2-Positive Tumor Xenografts with an Iodine-124 Labeled Anti-HER2 Diabody," Cancer Research 65(4):1471-1478 (2005).
Rossin et al., "Highly Reactive trans-Cyclooctene Tags with Improved Stability for Diels-Alder Chemistry in Living Systems," Bioconjugate Chemistry 24:1210-1217 (2013).
Rossin et al., "In Vivo Chemistry for Pretargeted Tumor Imaging in Live Mice," Angew. Chem 122:3447-3450 (2010).
Rossin et al., "Diels-Alder Reaction for Tumor Pretargeting: In Vivo Chemistry Can Boost Tumor Radiation Dose Compared with Directly Labeled Antibody," Journal of Nuclear Medicine 54:1-7 (2013).
Rossin et al., "Tumor pretargeting with Diels-Alder: A TCO derivative with improved properties," Nuclear Medicine and Biology 64:630 (2014).
Rossin et al., "Trans-Cyclooctene Tag with Improved Properties for Tumor Pretargeting with the Diels-Alder Reaction," Molecular Pharmaceutics 11:3090-3096 (2014).

(56) References Cited

OTHER PUBLICATIONS

Roxin et al., "Flexible or fixed: a comparative review of linear and cyclic cancer-targeting peptides," Future Med. Chem. 4(12):1601-1618 (2012).
Sharkey et al., "Signal amplification in molecular imaging by pretargeting a multivalent, bispecific antibody," Nature Medicine 11(11):1250-1255 (2005).
Siegel et al., "Cancer statistics, 2014" CA Cancer J Clin 64:9-29 (2014).
Sohn et al., "Resected Adenocarcinoma of the Pancreas-616 Patients: Results, Outcomes, and Prognostic Indicators," J Gastrointest Surg 4:567-579 (2000).
Trajkovic-Arsic et al., "Multimodal Molecular Imaging of Integrin αvβ3 for In Vivo Detection of Pancreatic Cancer," Journal of Nuclear Medicine 55:446-451 (2014).
Xiong et al., "Cetuximab, a Monoclonal Antibody Targeting the Epidermal Growth Factor Receptor, in Combination with Gemcitabine for Advanced Pancreatic Cancer: A Multicenter Phase II Trial," Journal of Clinical Oncology 22(13):2610-2616 (2004).
Yoshimoto et al., "In vivo SPECT Imaging with (111)In-DOTA-c(RGDfK) to Detect Early Pancreatic Cancer in a Hamster Pancreatic Carcinogenesis Model," Journal of Nuclear Medicine 53:765-771 (2012).
Zeglis et al., "A Pretargeted PET Imaging Strategy Based on Bioorthogonal Diels-Alder Click Chemistry," Journal of Nuclear Medicine 54:1389-1396 (2013).
Zeglis et al., "Optimization of a Pretargeted Strategy for the PET Imaging of Colorectal Carcinoma via the Modulation of Radioligand Pharmacokinetics," Molecular Pharmaceutics 12:3575-3587 (2015).
Zeng et al., "Comparison of Conjugation Strategies of Cross-Bridged Macrocyclic Chelators with Cetuximab for Copper-64 Radiolabeling and PET Imaging of EGFR in Colorectal Tumor-Bearing Mice," Mol. Pharmaceutics 11:3980-3987 (2014).
Zeng et al., "The Growing Impact of Bioorthogonal Click Chemistry on the Development of Radiopharmaceuticals," Journal of Nuclear Medicine 54:829-832 (2013).
U.S. Appl. No. 16/179,785, filed Aug. 5, 2020 Non-Final Office Action.

* cited by examiner

AE105-NOTA-RGD

AE105-PEG4-DOTA-PEG4-RGD

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Cys Asn Gly Arg Cys
1               5

DIMERIZATION STRATEGIES AND COMPOUNDS FOR MOLECULAR IMAGING AND/OR RADIOIMMUNOTHERAPY

CROSS-REFERENCE TO RELATED APPLICATIONS

This application is a continuation of International Patent Application No. PCT/US2017/030662, filed May 2, 2017, which claims priority to U.S. Provisional Application No. 62/330,622, filed May 2, 2016, U.S. Provisional Application No. 62/346,783, filed Jun. 7, 2016, and U.S. Provisional Application No. 62/373,036, filed Aug. 10, 2016, the contents of each and all of which are hereby incorporated by reference in their entireties.

GRANT INFORMATION

This invention was made with government support under Grant Nos. EB017317 and EB020737 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jun. 15, 2020, is named 072396_0739_SL.txt and is 702 bytes in size.

1. INTRODUCTION

The present invention relates to a multivalent molecular imaging and/or targeted drug delivery method, wherein the multivalent molecule targeting different biomarkers carries the imaging label and/or drug. Therefore, the multivalent molecule can bind to at least two biomarkers, which can be the same or different, resulting in increased sensitivity, increased specificity, increased binding affinity, increased Bmax, longer blood retention, improved signal to noise ratio, and improved pharmacokinetic performance. In particular, the multivalent molecules can image cancer or other diseases/disorders at an early stage and/or when the amount of biomarker is relatively low. The present invention also relates to chelators useful to prepare the multivalent molecules as well as other dimer molecules, including coupling of ligands to dye molecules. The chelators of the invention provide an improved ability to couple molecules without using additional chemical platforms. The present invention further relates to an in vitro high-throughput screening platform for the optimization of spacers in multivalent molecules.

2. BACKGROUND OF THE INVENTION

The clinical utility of monovalent imaging probes is often limited by a variety of factors, including receptor density, binding affinity, and in vivo pharmacokinetics. A multivalent strategy that improves avidity via multiple interactions is a promising approach to imaging and therapy. For example, hetero-bivalency, featuring the simultaneous binding of two linked ligands against two different receptors, has emerged as a promising targeting strategy due to several advantages over the mono-receptor targeted strategy. First, hetero-bivalency can easily convert low-affinity monovalent ligands ($K_d$~μM) to ligands having high avidity ($K_d$~nM). Second, hetero-bivalency presents a new mechanism of action not available for monomers (or homodimers), and the second binding site can be a receptor with low density, low specificity, or even non-specificity (such as a hydrophobic patch on a monomeric protein). Therefore, enhanced specific uptake is highly expected if two ligands were connected with an appropriate linkage. Third, due to changes in size and lipophilicity, heterodimers can have improved pharmacokinetic performance, especially in cases where clearance properties and excretion rates are not optimal for their monovalent counterparts. The probes to date, however, show limited capacity to identify cancer at early stages due to the heterogeneity of tumors and the complex tumor microenvironment.

Therefore, there is a need in the art for a molecular imaging and/or radioimmunotherapy method with increased sensitivity, increased specificity, increased binding affinity, increased Bmax, improved pharmacokinetics (e.g., longer blood retention and in cases where the clearance properties and excretion rates are not optimal for monovalent ligands), and improved signal to noise ratio, as well as for improved methods for generating multimers to be used for molecular imaging and radioimmunotherapy.

An example of such an approach is multivalency for molecular imaging and therapy as disclosed herein. It has been widely recognized that the length of spacer dramatically affects the avidity of bivalency in multimers. The traditional strategy of creating a multivalent compound comprises preparing analogues with varied length spacers between the ligands followed by corresponding in vitro and/or in vivo testing to find out the most suitable length of the spacer. This strategy, however, involves lengthy and costly synthetic work. In some cases, the length of a suitable spacer might be predicted from computer modeling studies, but this strategy is limited to the situation where the two targeted receptors interacted with each other, and the prediction can be incorrect. Therefore, there exists a need for an improved method for generating multivalent compounds with appropriate spacing between the ligands of the multivalent compounds.

3. SUMMARY OF THE INVENTION

The present invention relates to compounds, kits, and methods for targeted molecular imaging and/or therapy. In its broadest aspect, the present invention relates to two components or molecules which interact with biomarkers on a cell, tissue, or structure of interest. It is based, at least in part, on the discovery that targeting at least two biomarkers on the cell (e.g., tumor cell) increases the sensitivity and/or specificity of the imaging label and/or active agent and also improves the pharmacokinetic properties of the molecules. The present invention also relates to methods of targeted molecular imaging and/or targeted drug delivery.

The present invention provides for compounds, compositions, methods, and kits for molecular imaging. In certain non-limiting embodiments, the molecular imaging multivalent compound comprises at least one first targeting molecule that binds and/or interacts with at least one biomarker; at least one second targeting molecule that binds and/or interacts with at least one other biomarker; and a detectable label. In certain embodiments, the compound can have more than one detectable label.

In certain non-limiting embodiments, a molecular imaging multimodal and/or multivalent compound comprises at least one targeting molecule that binds and/or interacts with at least one biomarker; at least one first detectable label; and at least one second detectable label.

In certain non-limiting embodiments, the detectable label is an imaging label. In certain non-limiting embodiments, the imaging label can be, but is not limited to an isotope selected from the group consisting of $^{64}$Cu, $^{68}$Ga, $^{18}$F, $^{89}$Zr, $^{111}$In, Al$^{18}$F or $^{99m}$Tc. In certain non-limiting embodiments, the detectable label is a dye molecule. In certain non-limiting embodiments, the dye molecule can be, but is not limited to, cyanine, FluoProbes, or DyLight Fluor dye.

The present invention provides for compounds, compositions, methods, and kits for targeting drug delivery. In certain non-limiting embodiments, the targeted drug delivery multivalent compound comprises at least one first targeting molecule that binds and/or interacts with at least one biomarker; at least one second targeting molecule that binds and/or interacts with at least one other biomarker; and at least one active agent.

In certain non-limiting embodiments, the active agent can be, but is not limited to, a protein, peptide, small molecule, nanoparticle, pharmaceutical, or radiopharmaceutical. In certain non-limiting embodiments, the radiopharmaceutical can comprise $^{67}$Cu, $^{177}$Lu, $^{90}$Y, $^{131}$I, $^{212}$Bi, $^{211}$At, $^{225}$Ac, $^{188}$Re, or $^{111}$In. Non-limiting examples of pharmaceuticals (which can optionally incorporate a radioisotope) include anticancer agents, antiinfective agents, antiproliferative agents, agents that modulate the immune response including agents that augment or that reduce the immune response, antithrombotic agents, etc. In certain non-limiting embodiments, the small molecule can be, but is not limited to, doxorubicin, paclitaxel or fluorouracil.

In certain non-limiting embodiments, the first targeting molecule and/or second targeting molecule of the multivalent compound binds to at least one biomarker of a biological subject of interest. In certain non-limiting embodiments, the first targeting molecule and/or second targeting molecule can each individually be, but is not limited to, a protein, antibody, peptide, small molecule, nanoparticle, polysaccharide, or polynucleotide. In certain non-limiting embodiments, the first targeting molecule and/or second targeting molecule can be internalizable or non-internalizable.

In certain non-limiting embodiments, the first and second targeting molecules target the same or different biomarker of a biological subject of interest. In certain non-limiting embodiments, if the first and second targeting molecules bind two different biomarkers, the biomarkers are expressed on the same biological subject. In certain non-limiting embodiments, the biological subject of interest can be, but is not limited to, a cell. In certain non-limiting embodiments, the biological subject of interest can be, but is not limited to, a cell, tissue, or structure of interest, for example a tumor or cancer cell. In certain non-limiting embodiments, the biomarker can be expressed on the surface of the cell or internally. In certain non-limiting embodiments, the biomarker can be, but is not limited to, a cell surface protein. In certain non-limiting embodiments, the biomarker can be, but is not limited to, an integrin. In certain non-limiting embodiments, the biomarker can be, but is not limited to, CD13 and/or integrin αvβ3. In certain non-limiting embodiments, the biomarker can be, but is not limited to, uPAR and/or integrin αvβ3.

In certain non-limiting embodiments, the targeting molecule can be, but is not limited to, a CD13 targeting molecule. In certain non-limiting embodiments, the CD13 targeting molecule can be, but is not limited to, peptides containing the Asn-Gly-Arg (NGR) motif. In certain non-limiting embodiments, the CD13 targeting molecule can be a peptide such as, but is not limited to, cyclo(cNGRc), cyclo(cPNGRc), cyclo(NGRyK), linear cNGRc, or linear cPNGRc. In certain non-limiting embodiments, the targeting molecule can be, but is not limited to, integrin αvβ3 targeting molecules. In certain non-limiting embodiments, the integrin αvβ3 targeting molecule can be, but is not limited to a protein with an exposed arginine-glycine-aspartic (RGD) tripeptide motif. In certain non-limiting embodiments, the integrin αvβ3 targeting molecule can be a peptide such as, but not limited to, cyclo(RGDyK) or cyclo(RADyK). In certain non-limiting embodiments, the targeting molecule can be, but is not limited to, a uPAR targeting molecule. In certain non-limiting embodiments, the uPAR targeting molecule can be, but is not limited to, uPA, ATF (amino terminal fragment of urokinase), AE105, or AE105mut.

In certain non-limiting embodiments, the at least one first targeting molecule and at least one second targeting molecule can be attached via a spacer (e.g., polymer). In certain non-limiting embodiments, the at least one first targeting molecule and at least one second targeting molecule can be attached via a chelator. In certain non-limiting embodiments, the at least one first targeting molecule and the at least one second targeting molecule are attached to the chelator via a spacer (e.g., polymer). In certain non-limiting embodiments, the chelator comprises a multifunctional chelator. In certain non-limiting embodiments, the chelator combines a carboxylic acid or active ester group for an amide bond connection, an azide group suitable for click chemistry, and a chelating core. In certain non-limiting embodiments, the chelator comprises a 1, 4, 7-triazacyclonenonane (TACN)-based chelator. In certain non-limiting embodiments, the chelator comprises NOTA, DOTA, L-NETA, $N_3$—NO'$B_2$ or $N_3$-DO'$B_3$. In certain non-limiting embodiments, the chelator can be bound to one targeting molecule (e.g., either the first or second targeting molecule) for monomers. In certain non-limiting embodiments, the chelator can be bound to two of the same targeting molecules (e.g., either two of the first or two of the second targeting molecule) for homodimers. In certain non-limiting embodiments, the chelator can be bound to two different targeting molecules (e.g., the first and second targeting molecule) for heterodimers. In certain non-limiting embodiments, the chelator can be bound to one targeting molecule (e.g., either the first or second targeting molecule) and one dye molecule for multimodalities.

In certain non-limiting embodiments, the presently disclosed compounds can be used in methods of imaging a cell, tissue, or structure of interest in a subject in need of such treatment, for example a subject having a disease or disorder, at risk of having a disease or disorder, or being screened/tested for a disease of disorder, wherein the subject is administered a compound in accordance with the present invention.

In certain non-limiting embodiments, the invention provides an in vitro high-throughput screening platform for optimizing the length of spacers between the targeting molecules of the multivalent compounds. In certain non-limiting embodiments, the method combines click chemistry and radio chemistry to optimize the spacer length. In certain non-limiting embodiments, cells can be used as a screening platform via on-site formation of multivalent compound. In certain non-limiting embodiments, the targeting molecules of the multivalent compound can be functionalized separately with a reactive group and a photolabile (i.e., phototriggerable) group. In certain non-limiting embodiments, the in vitro high-throughput screening platform comprises exposing cells to a first functionalized targeting molecule and a second functionalized targeting molecule, wherein at least one of the functionalized targeting molecules can be attached to spacers of different lengths and at least one other set of functionalized targeting molecules is attached to a spacer with a set length. In certain non-limiting embodiments, the targeting molecules are functionalized with functional groups that allow the spacers of the first functionalized targeting molecules to bind to the spacers of the second functionalized targeting molecules. In certain non-limiting embodiments, at least one of the functional groups is activated by photon energy to allow binding to the other functionalized groups. In certain non-limiting embodiments, radio-metal labeled reactive groups can be added to bind to at least one population of functionalized targeting molecules that are not bound via its spacer to another functionalized targeting molecule. In certain non-limiting embodiments, the amount of bound radio-metal (e.g., $^{68}$Ga, $^{64}$Cu, Al$^{18}$F, $^{177}$Lu, $^{111}$In, and $^{89}$Zr)-labeled reactive groups is measured to determine which spacer length resulted in the most binding between the two functionalized targeting molecule populations.

The present invention also provides for kits for targeted medical imaging and/or targeted drug delivery. In certain non-limiting embodiments, the kit includes at least one multivalent compound comprising at least one first targeting molecule, at least one second targeting molecule, and at least one detectable label and/or active agent. In certain non-limiting embodiments, the kit includes at least one compound comprising one targeting molecule and at least one detectable label or active agent. In certain non-limiting embodiments, the kit comprises a chelator that can attach at least one first targeting molecule and at least one second targeting molecule. In certain non-limiting embodiments, the kit comprises a spacer (e.g., polymer) for attaching the at least one first targeting molecule and the at least one second targeting molecule to each other or a chelator. In certain non-limiting embodiments, the chelator comprises a multifunctional chelator. In certain non-limiting embodiments, the kit contains instructions for using the kit.

4. BRIEF DESCRIPTION OF THE FIGURES

FIG. 1. A non-limiting schematic of multivalent compounds of the invention.

Figure 2:
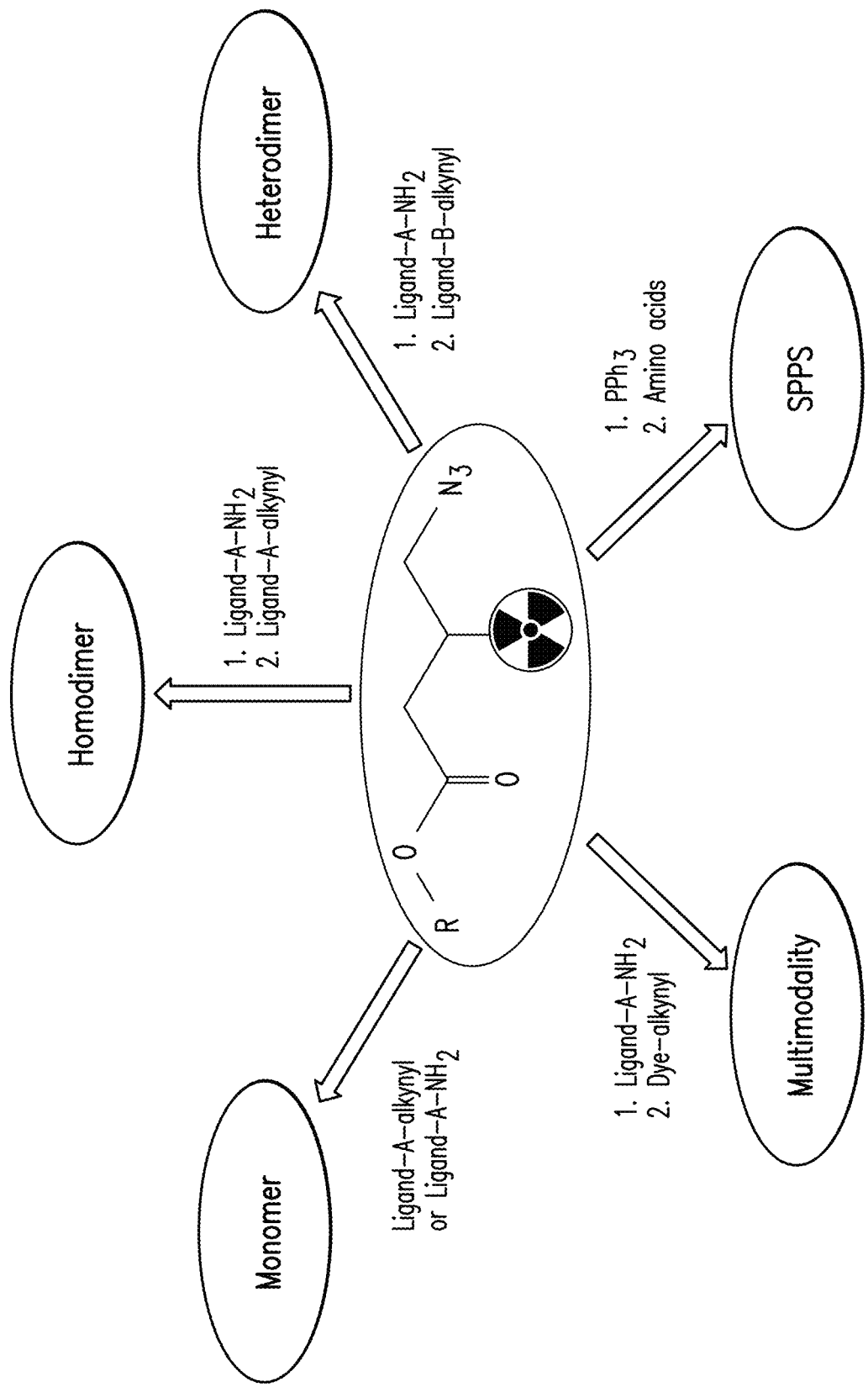

FIG. 2. A non-limiting schematic for making multivalent compounds of the invention.

Figure 3:
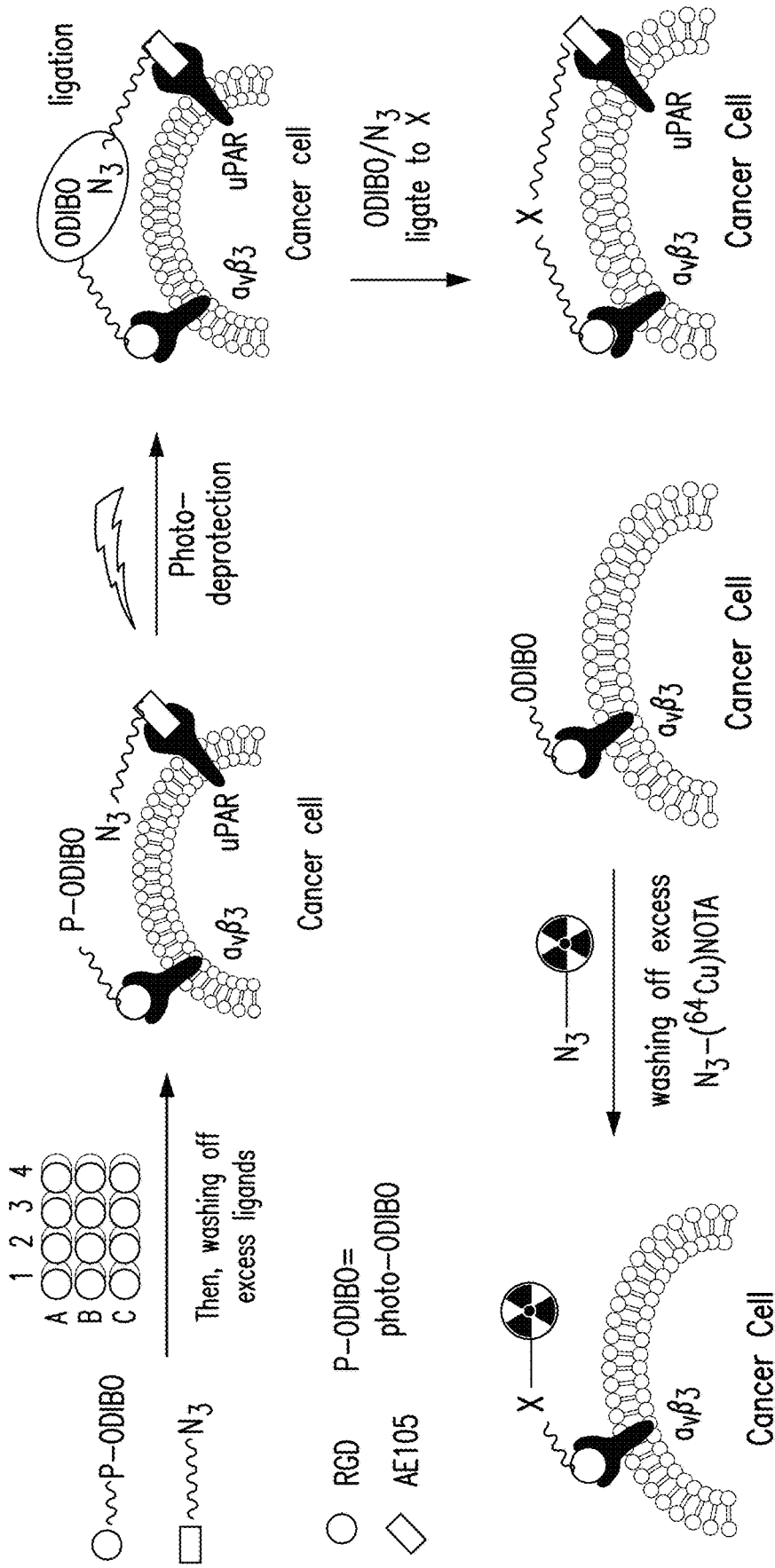

FIG. 3. A non-limiting schematic of the high-throughput screening platform of the invention.

Figure 4:
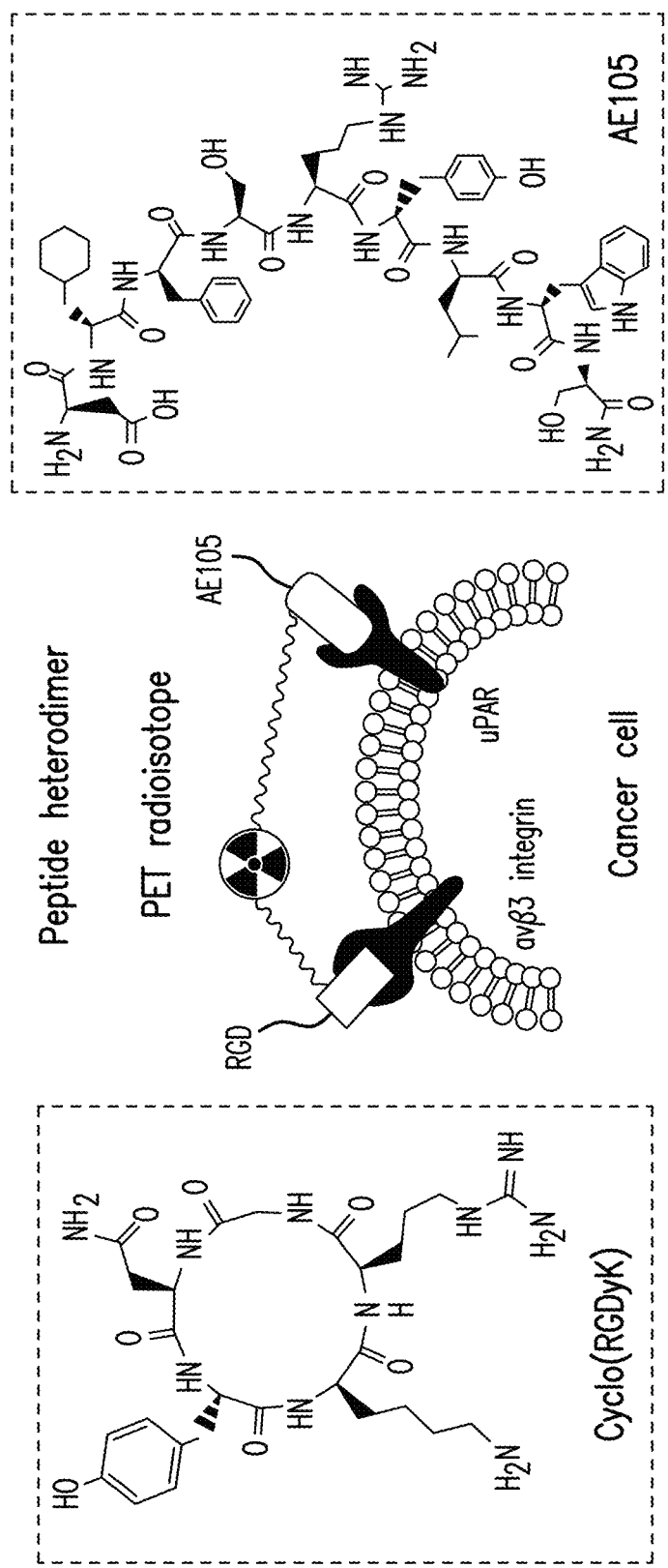
Figure 4:
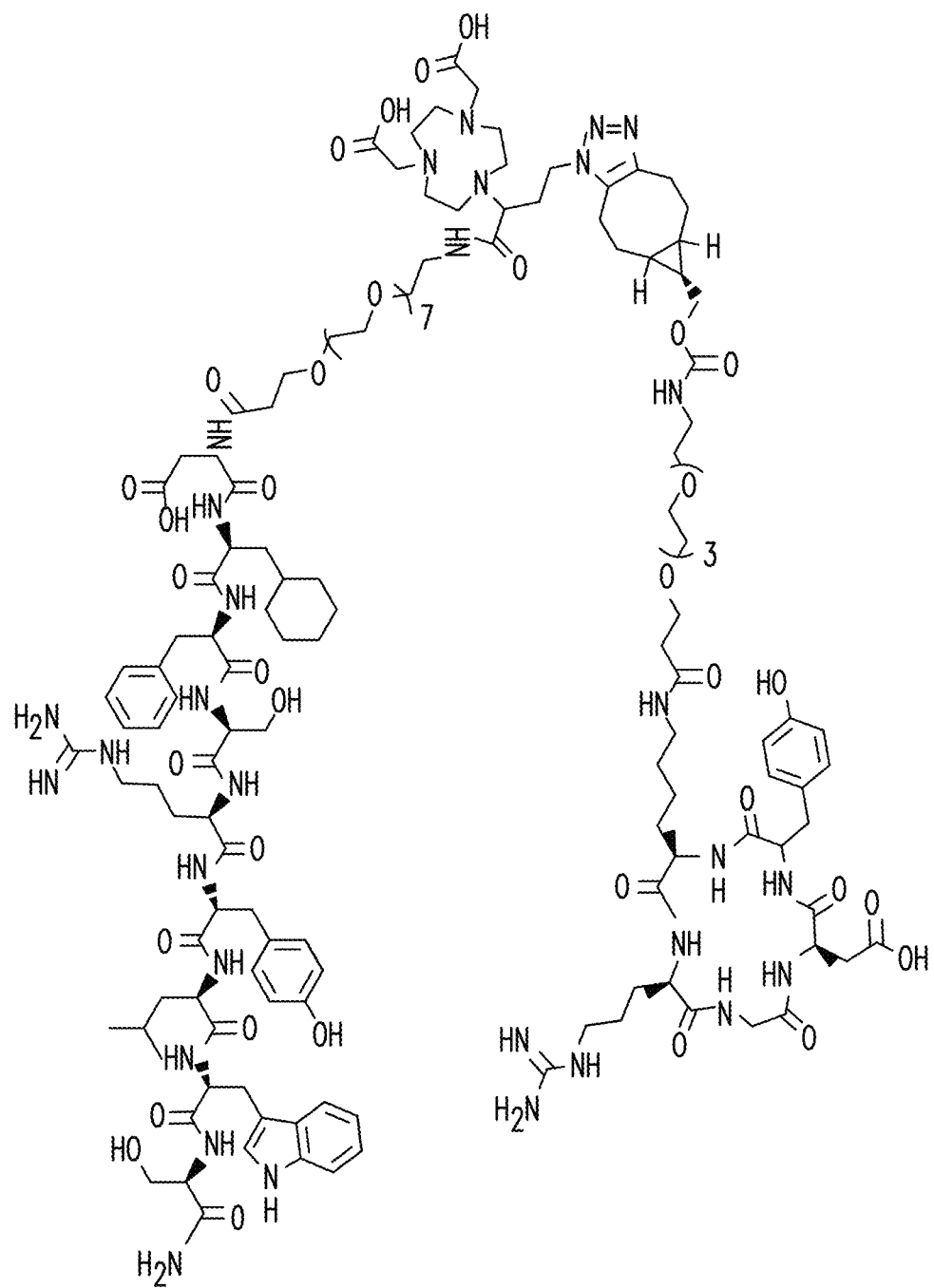

FIG. 4. Structure of AE105-NOTA-RGD.

Figure 5:
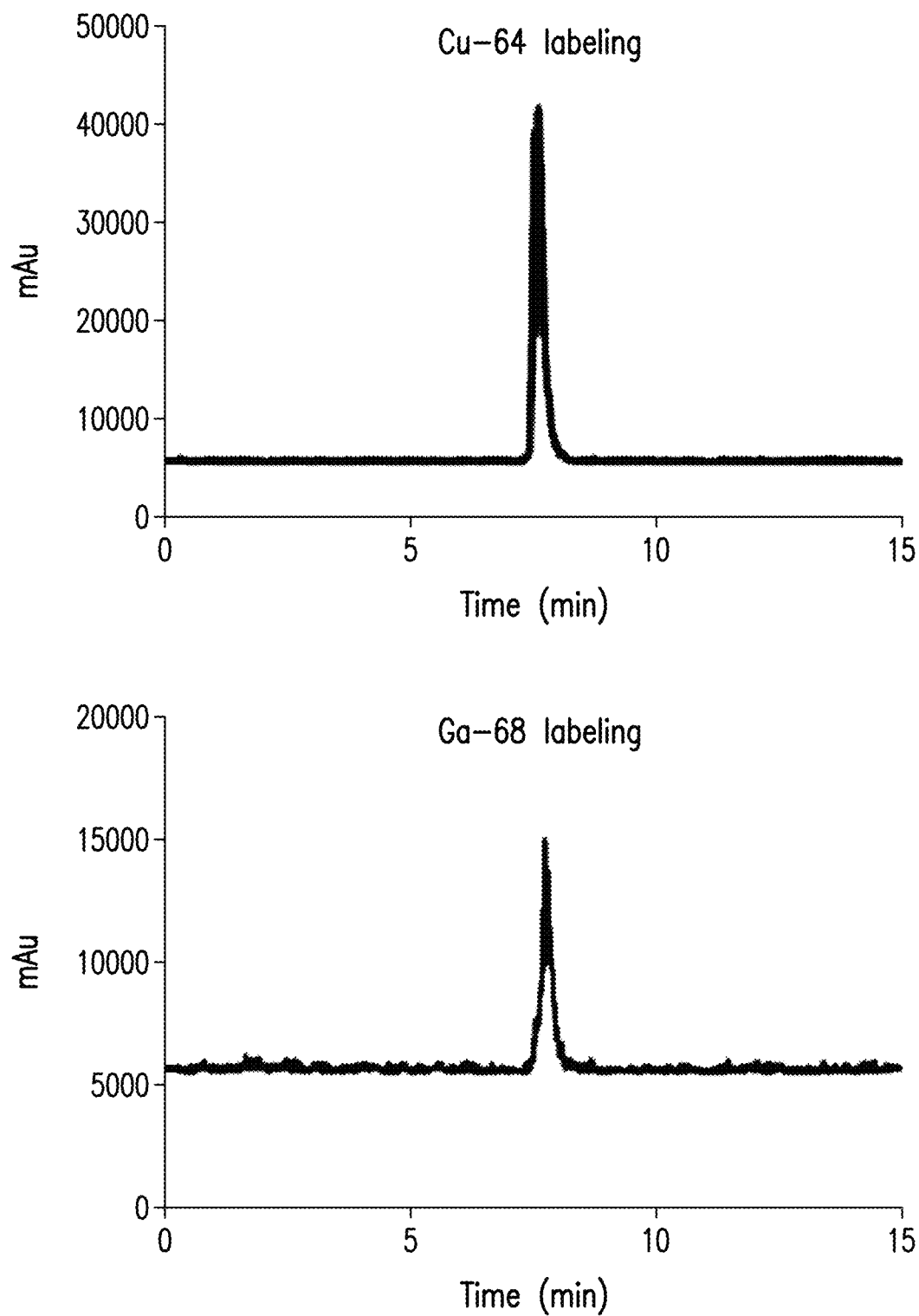

FIG. 5. Representative HPLC results of radiolabeling of probes.

Figure 6:
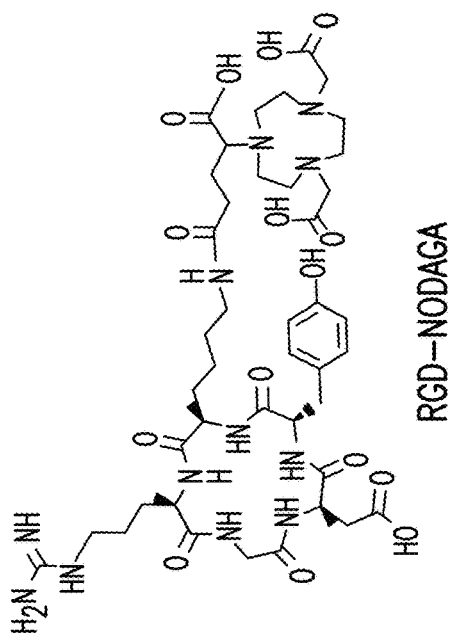
Figure 6:
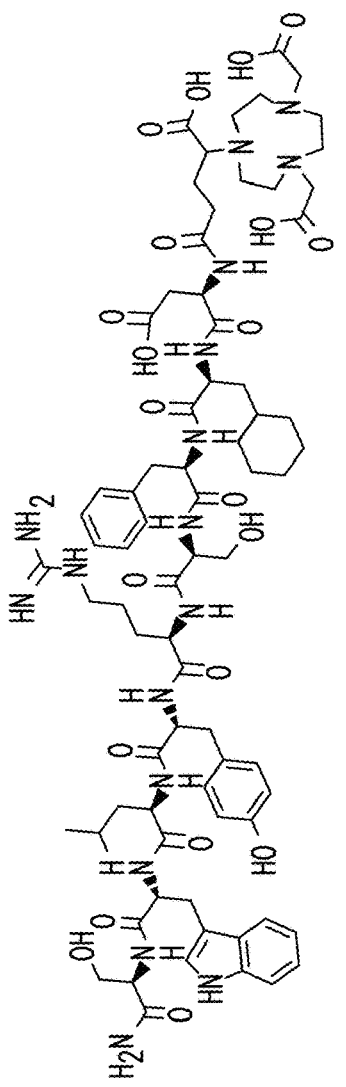

FIG. 6. Structures of AE105-NODAGA and RGD-NODAGA.

Figure 7:
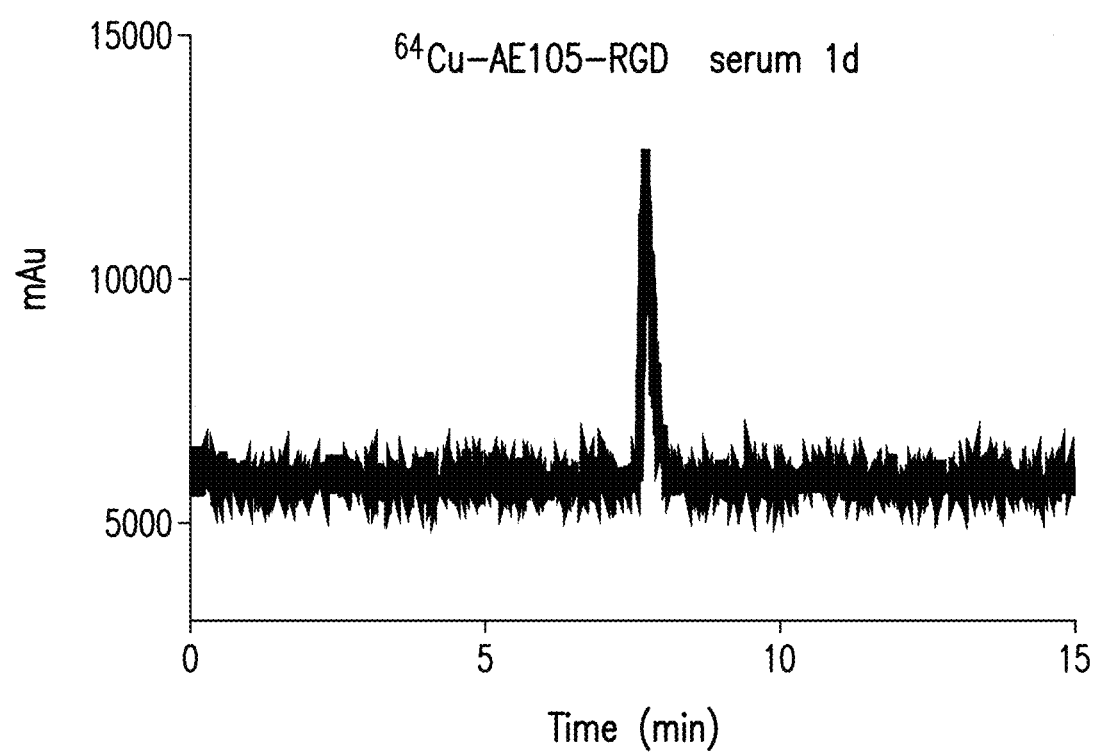

FIG. 7. Radio-HPLC results showing no significant $^{64}$Cu-disassociation after incubating the probe in serum for 1 day.

Figure 8:
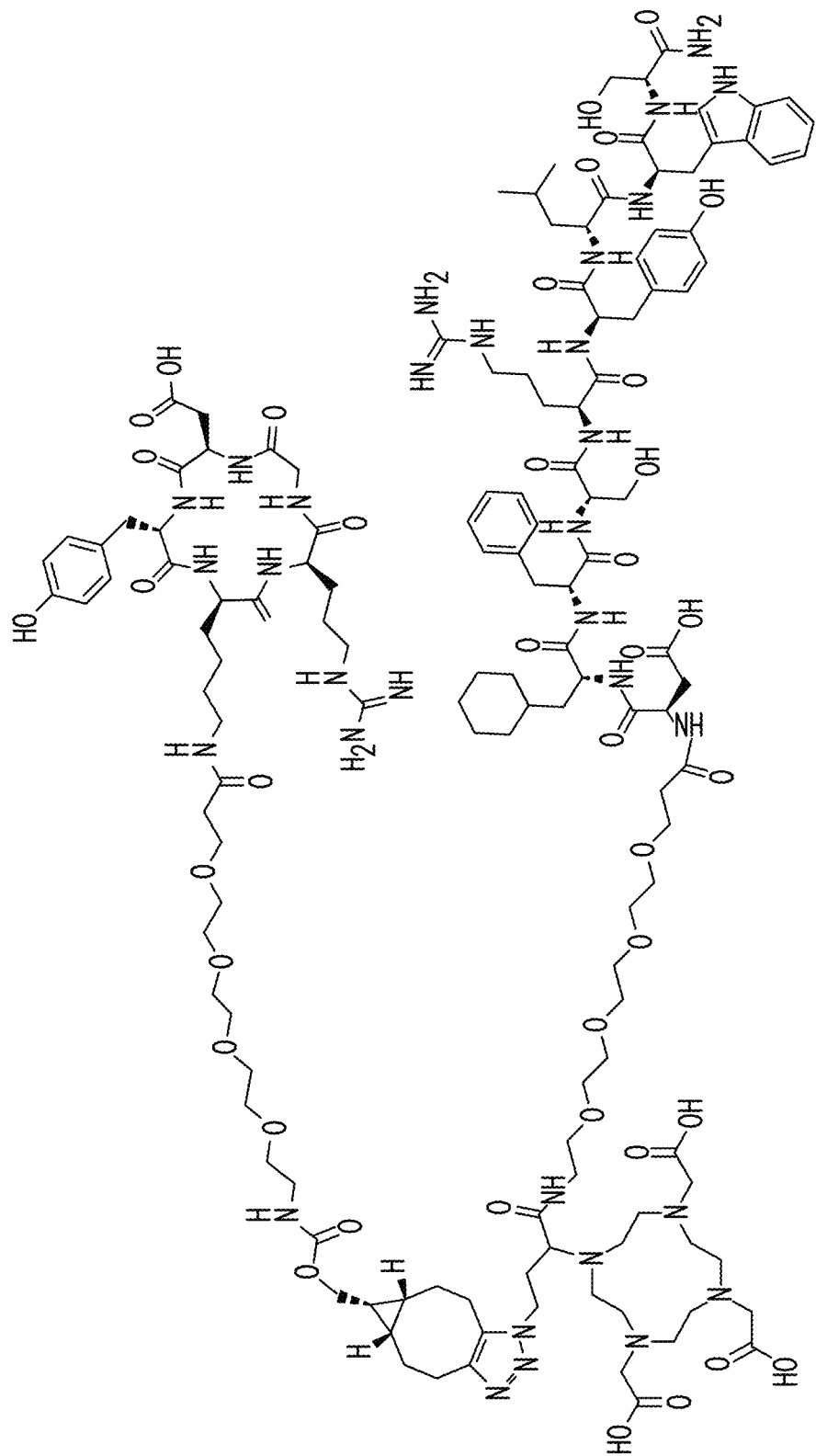

FIG. 8. Structure of AE105-PEG4-DOTA-PEG4-RGD.

Figure 9A:
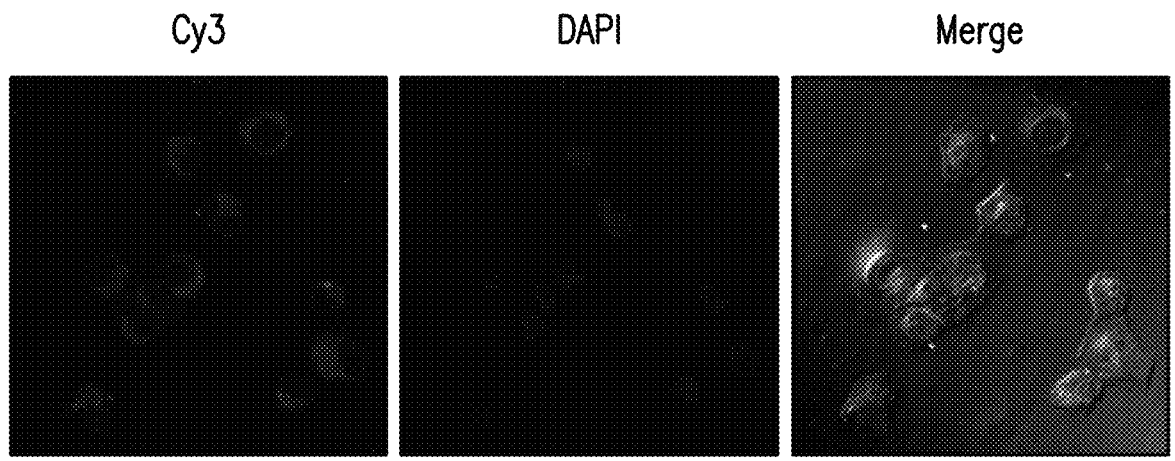
Figure 9B:
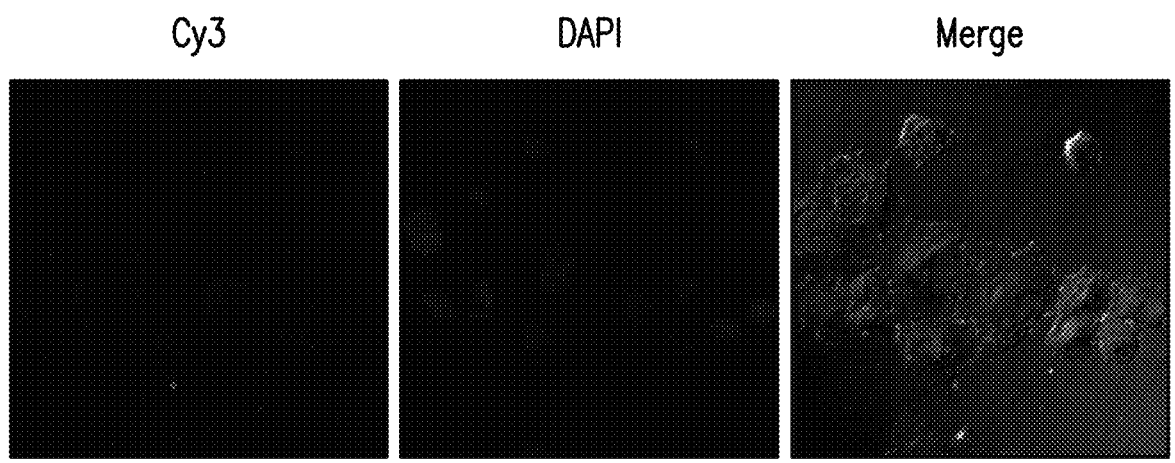

FIGS. 9A-9B. U87MG cell stain using AE105-NOTA-NHCO-Cy3 (A) and blockade (B)

Figure 10:
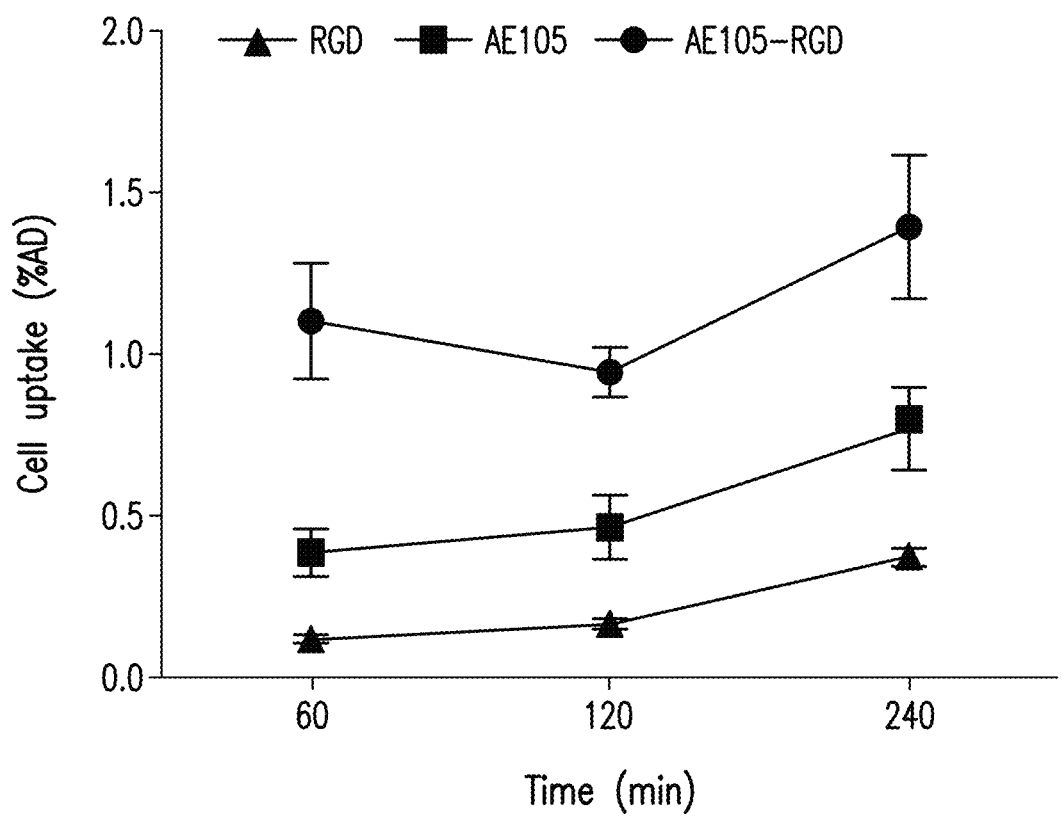

FIG. 10. Cell-uptake assay of AE105-NOTA-RGD, AE105-NODAGA and RGD-NODAGA.

Figure 11:
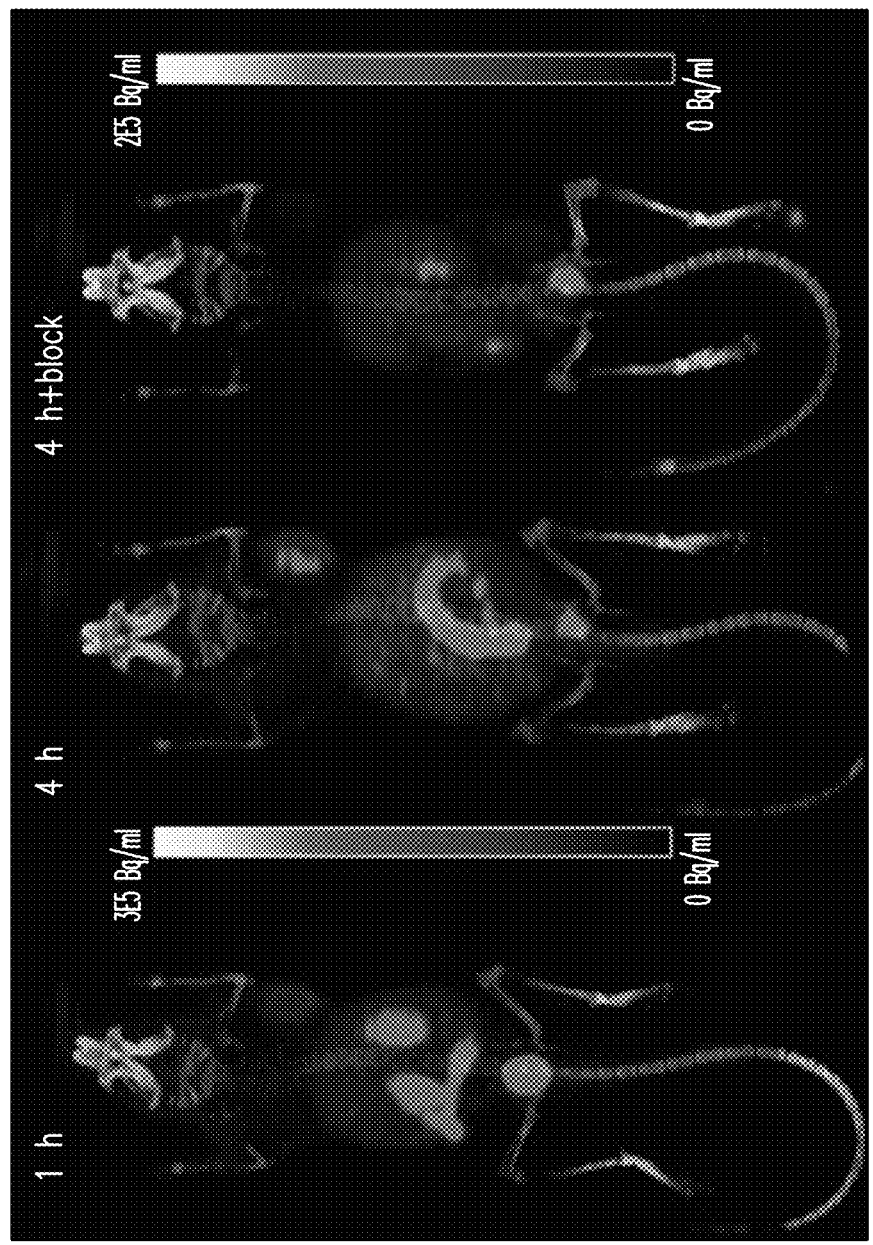

FIG. 11. PET imaging of mice bearing human U87MG tumor cells 1 hour and 4 hours after injection of the $^{64}$CU-labeled AE105-NOTA-RGD compound.

Figure 12:
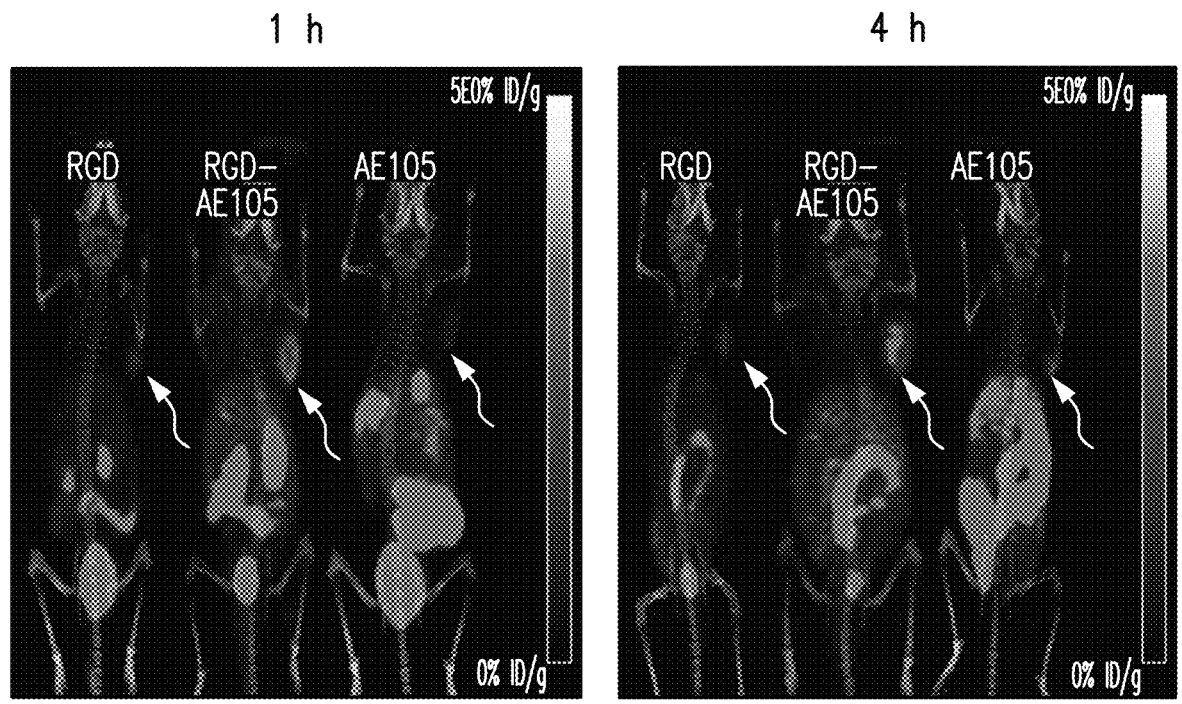
Figure 12:
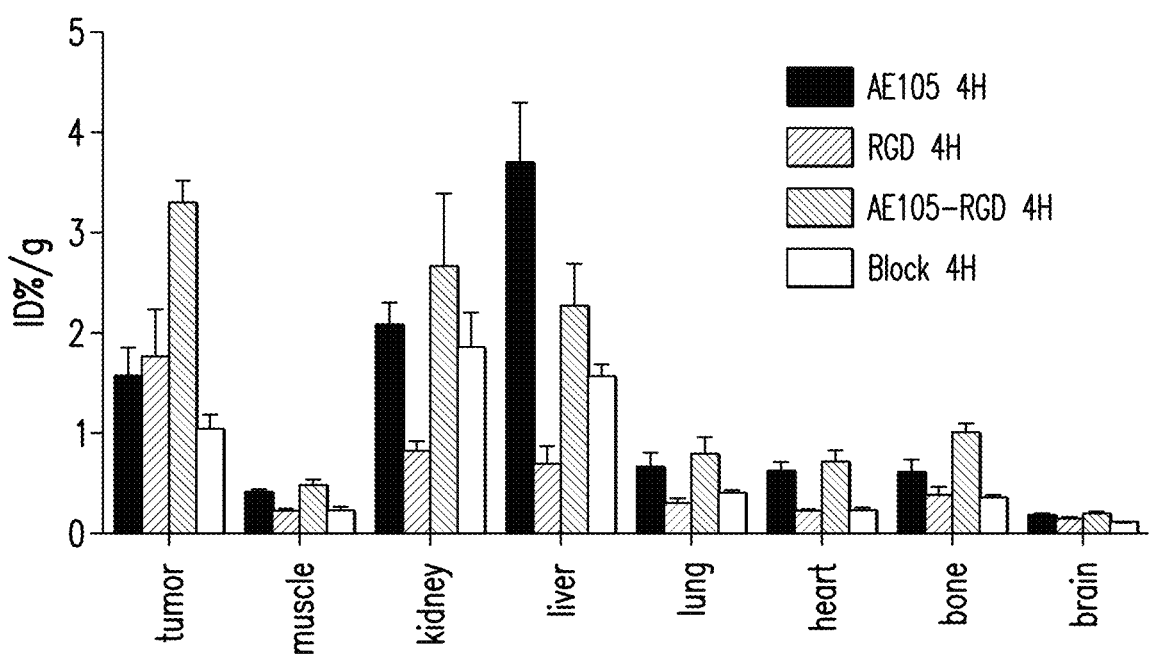

FIG. 12. Comparison of PET images between the $^{64}$Cu-labeled heterodimer and monomers at 1 h and 4 h post injection.

Figure 13:
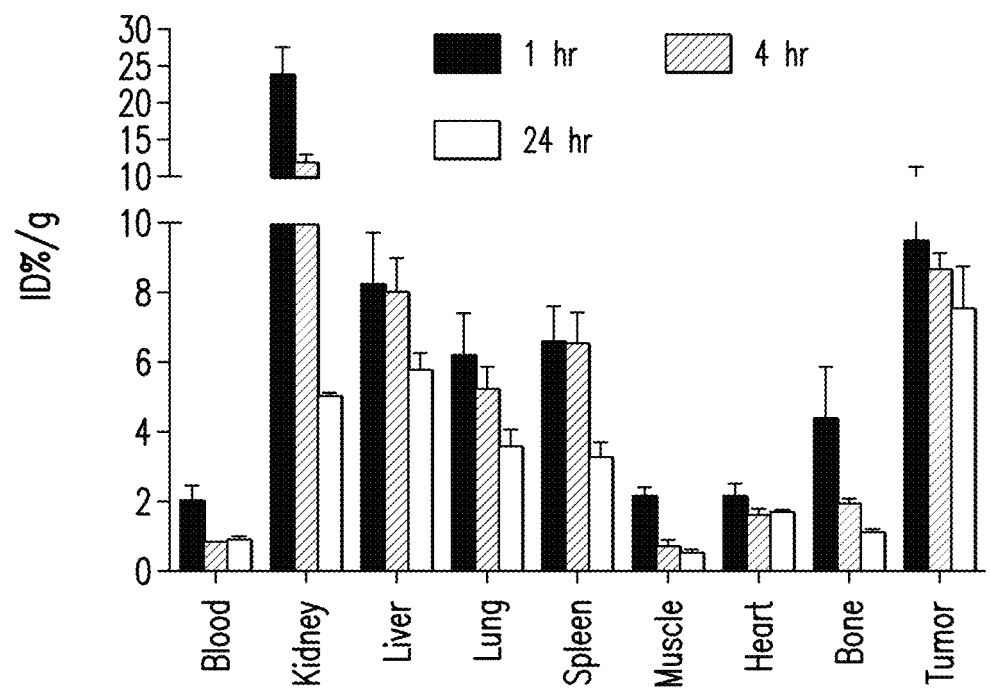
Figure 13:
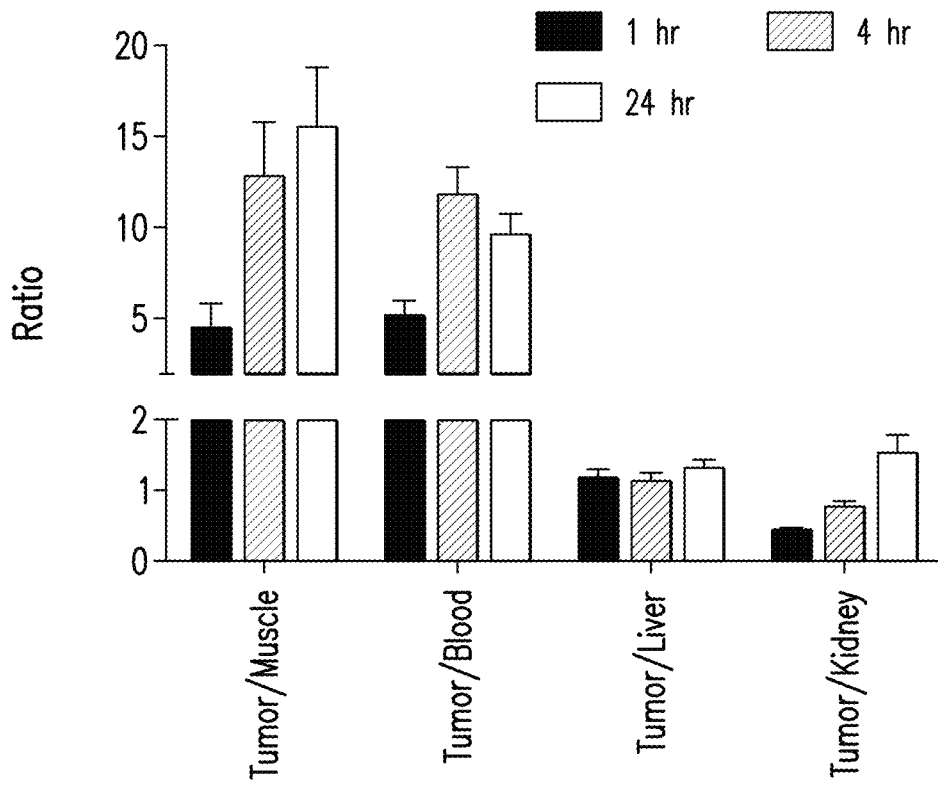

FIG. 13. Ex vivo biodistribution of the $^{64}$Cu-labeled AE105-NOTA-RGD compound, and tumor-to-non-tumor ration of the uptake.

Figure 14:
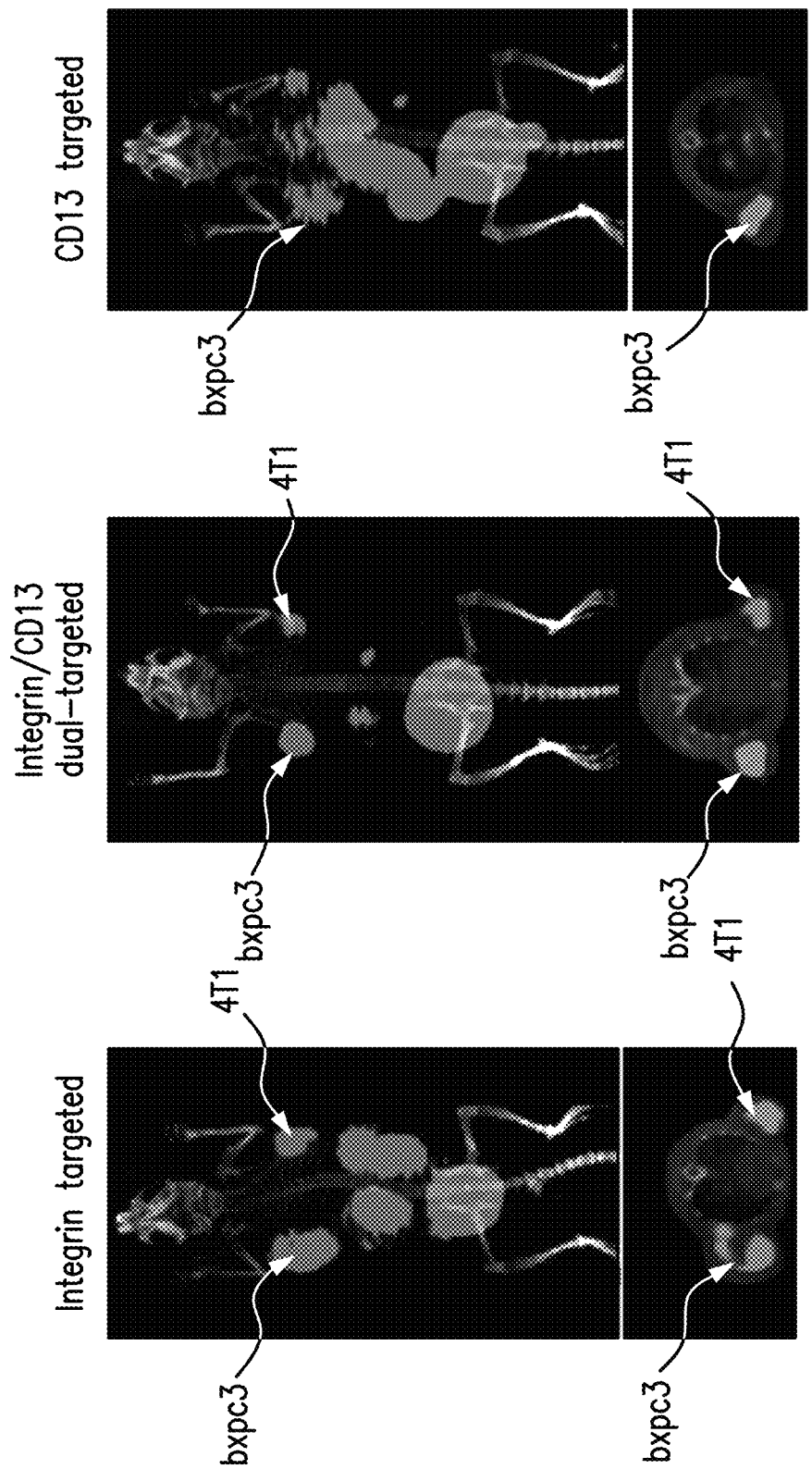

FIG. 14. PET imaging of mice bearing human bxpc3 and 4T1 tumor cells after injection of CNGRC-($^{68}$Ga)NOTA-RGDyK heterodimer ("CNGRC" disclosed as SEQ ID NO: 1), ($^{68}$Ga)NOTA(CNGRC) ("CNGRC" disclosed as SEQ ID NO: 1), or ($^{68}$Ga)NOTA(RGDyK).

Figure 15A:
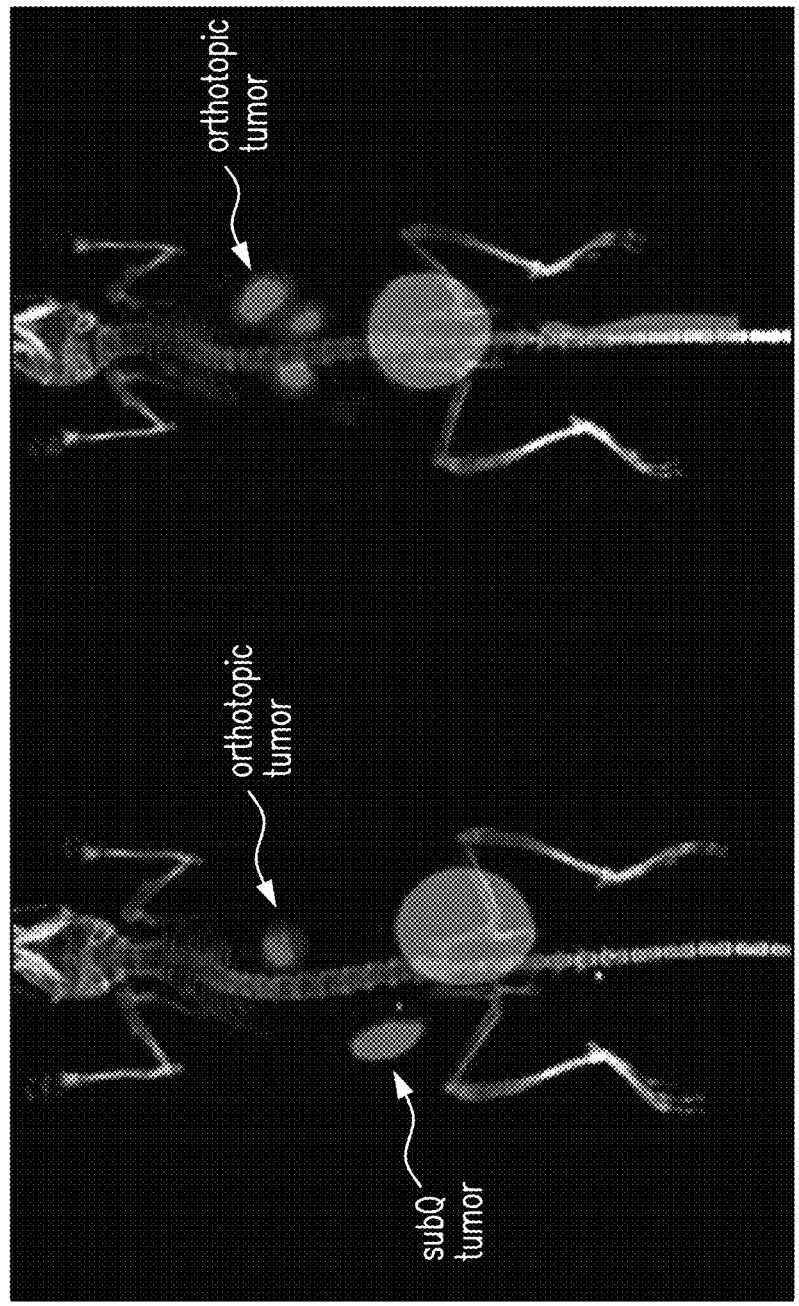
Figure 15B:
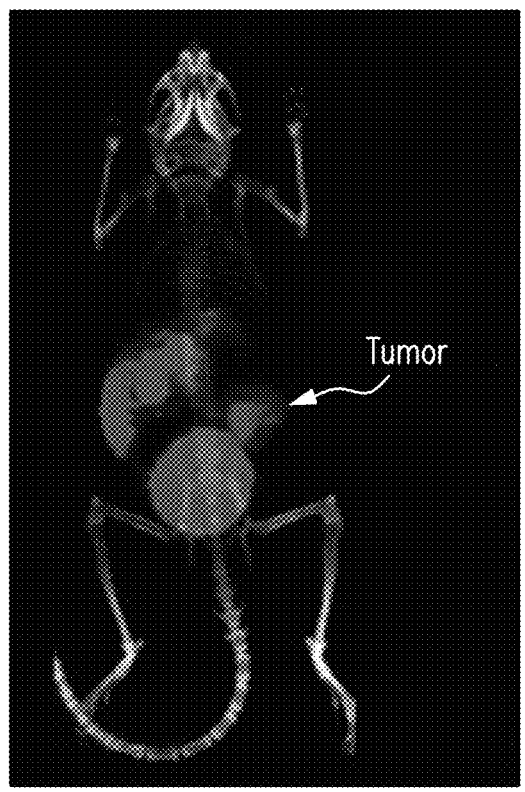
Figure 15C:
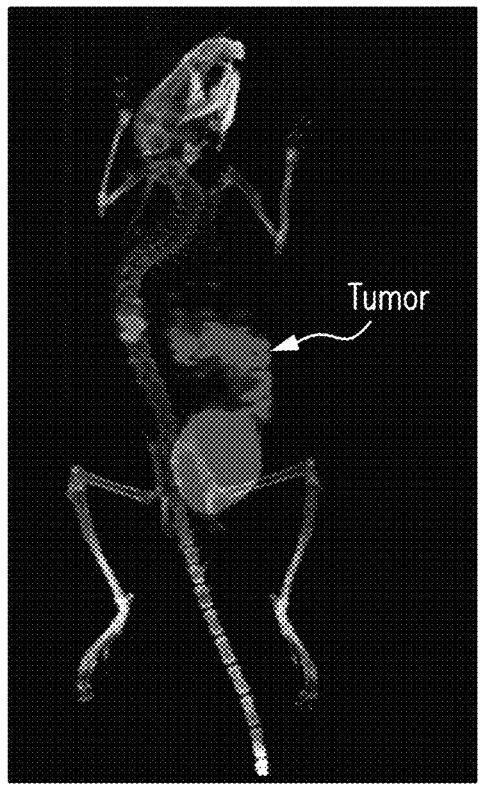

FIGS. 15A-15C. PET imaging in the orthotopic xenograft mouse model. FIG. 15A provides PET image after injection of CNGRC-($^{68}$Ga)NOTA-RGDyK heterodimer ("CNGRC" disclosed as SEQ ID NO: 1). FIG. 15B provides PET image after injection of RGD monomer. FIG. 15C provides PET image after injection of NGR monomer.

Figure 16A:
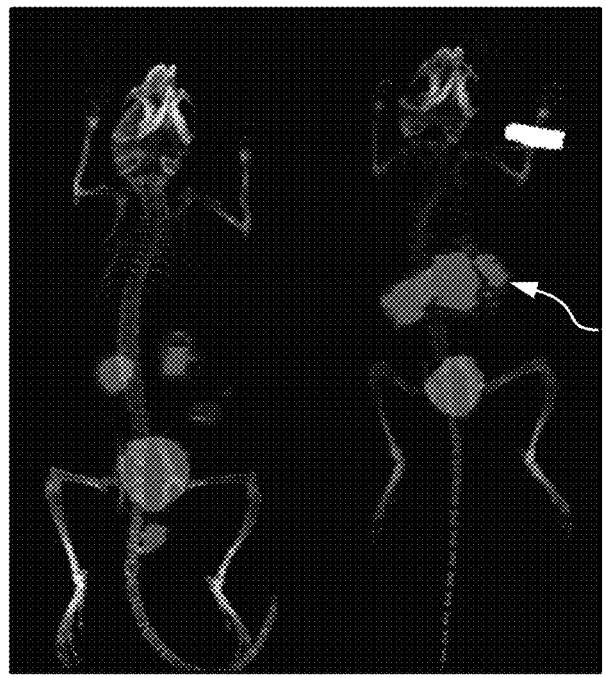
Figure 16B:
Figure 16C:
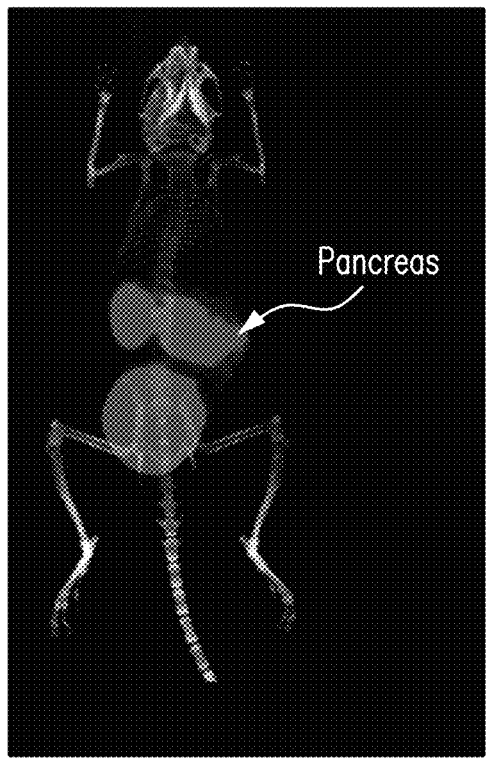
Figure 16D:
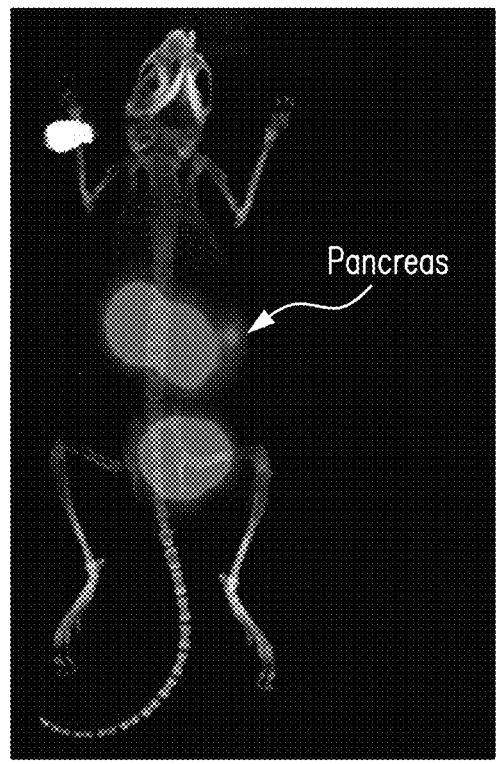

FIGS. 16A-16D. PET imaging in a genetically engineered mouse (GEM) model. FIG. 16A provides PET image after injection of CNGRC-($^{68}$Ga)NOTA-RGDyK heterodimer ("CNGRC" disclosed as SEQ ID NO: 1). FIG. 16B provides PET image after injection of $^{18}$F-FDG. FIG. 16C provides PET image after injection of RGD monomer. FIG. 16D provides PET image after injection of NGR monomer.

Figure 17:
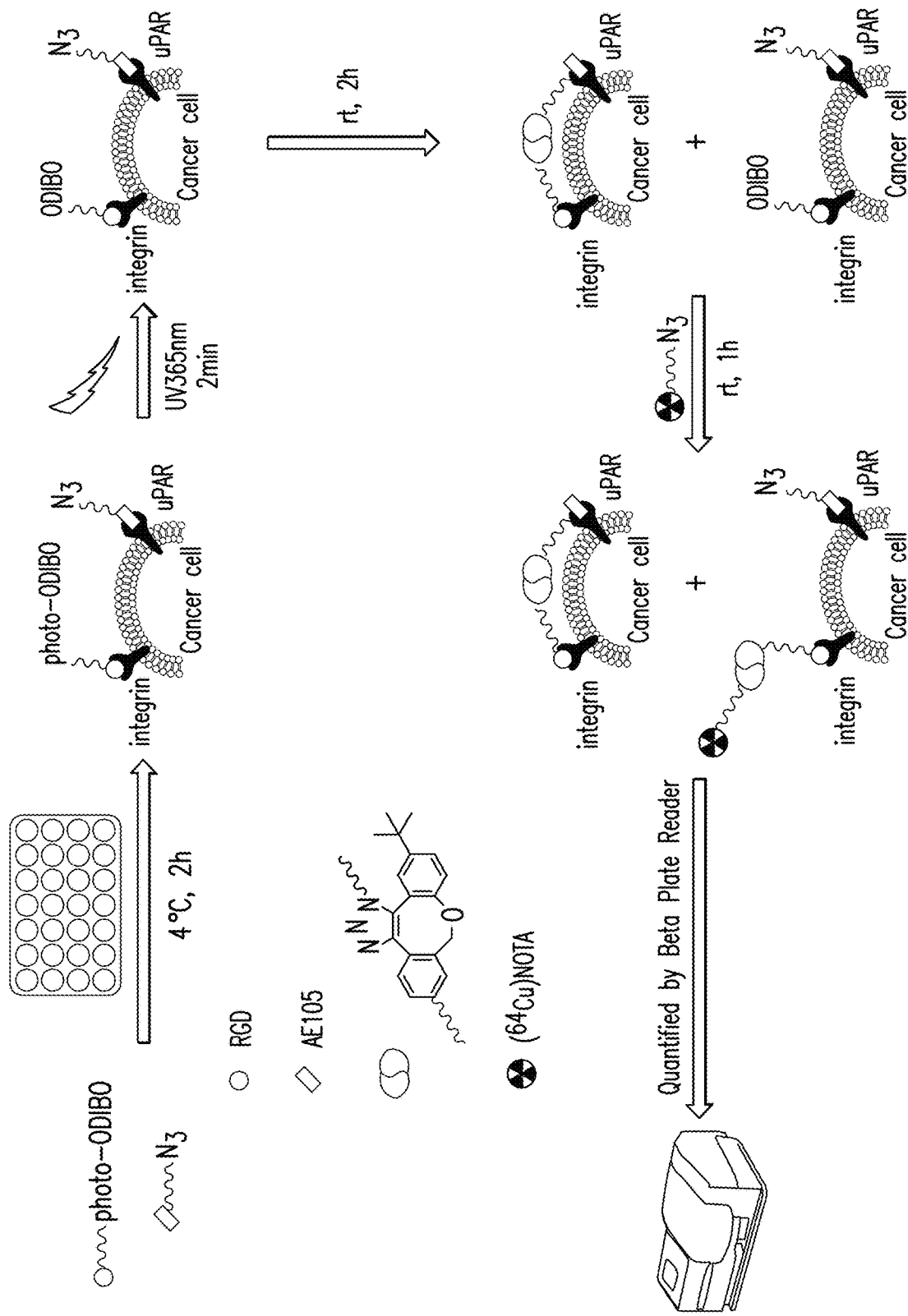

FIG. 17. Schematic illustration of the working rationale of an in vitro screening platform according to the present invention.

Figure 18A:
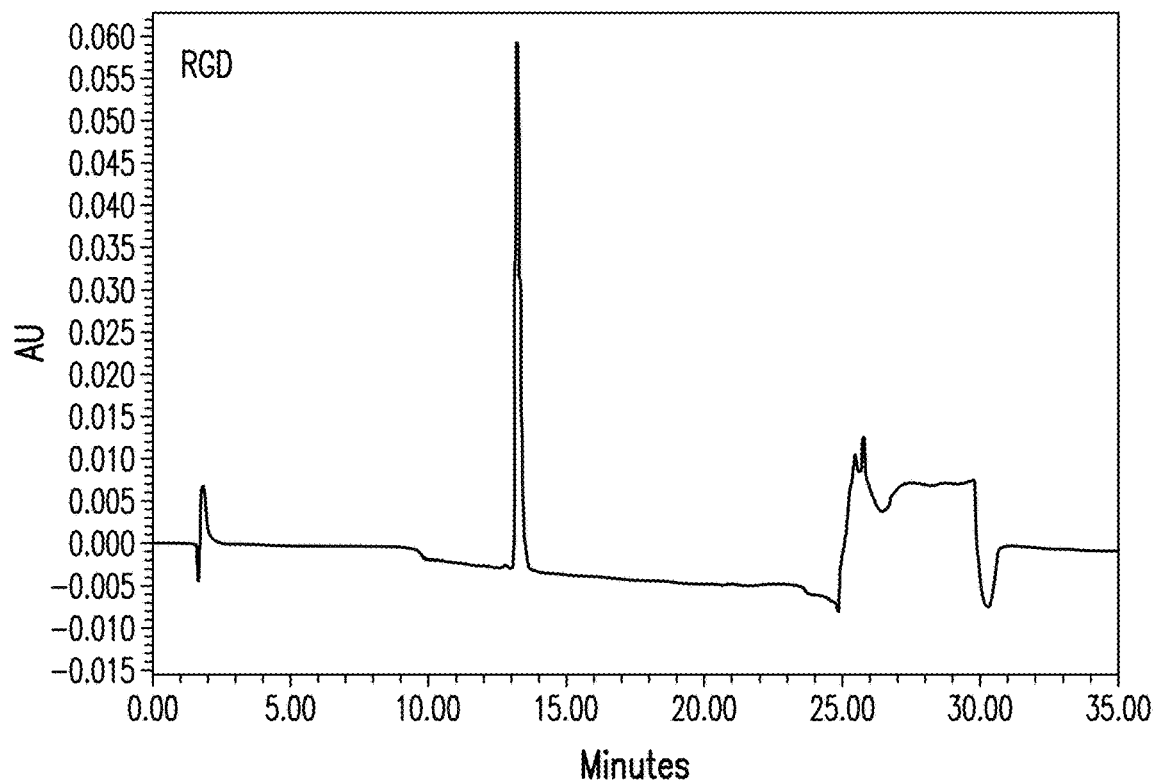
Figure 18B:
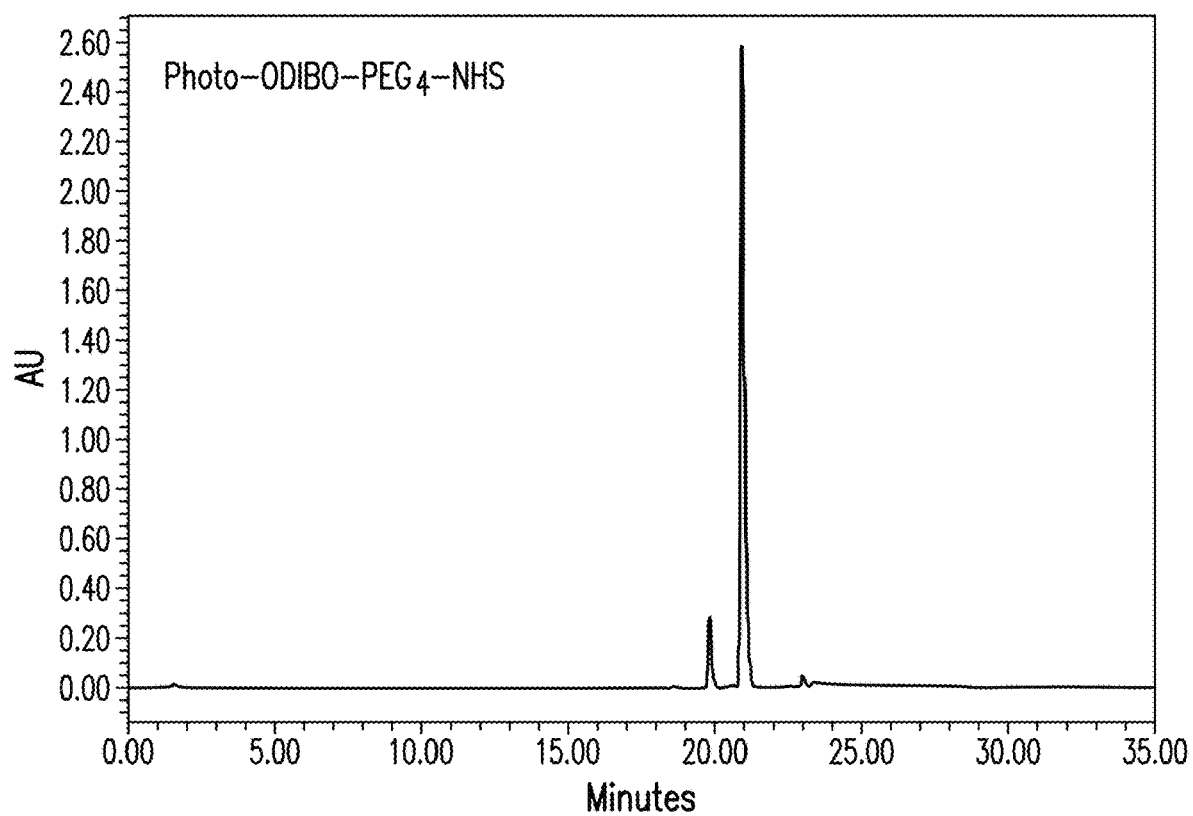
Figure 18C:
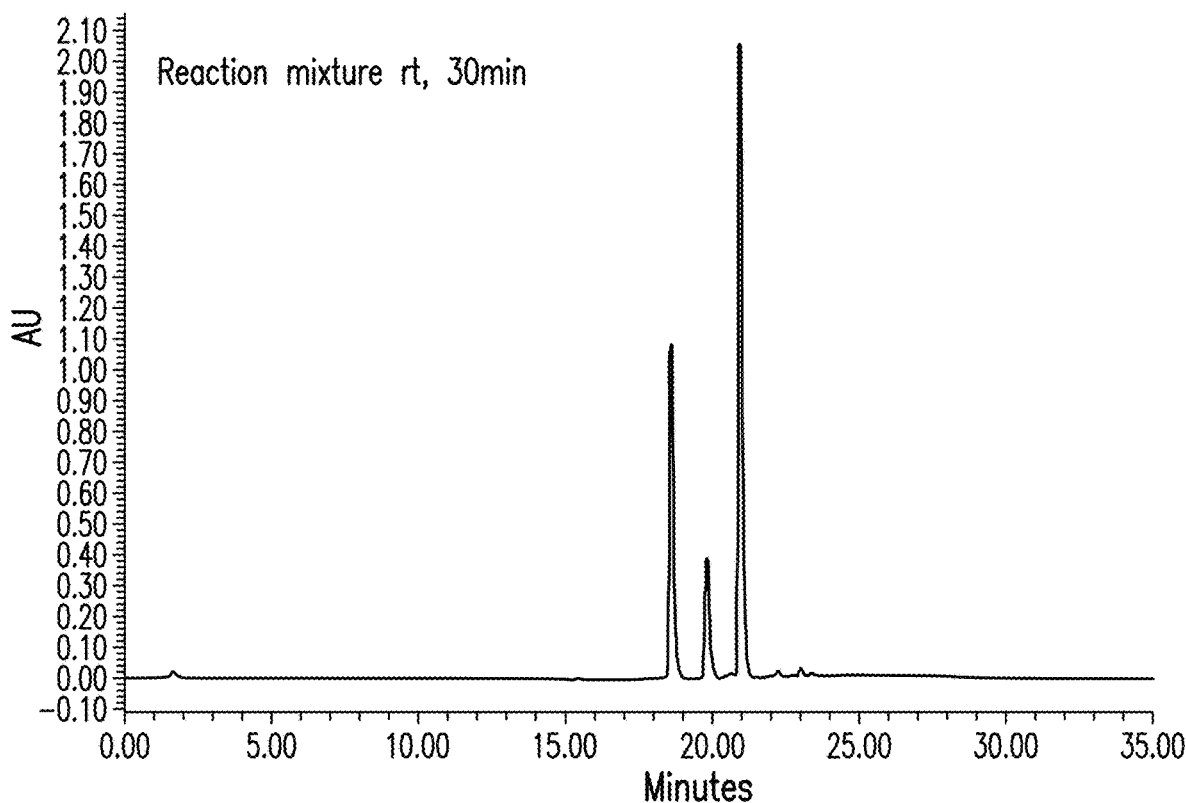
Figure 18D:
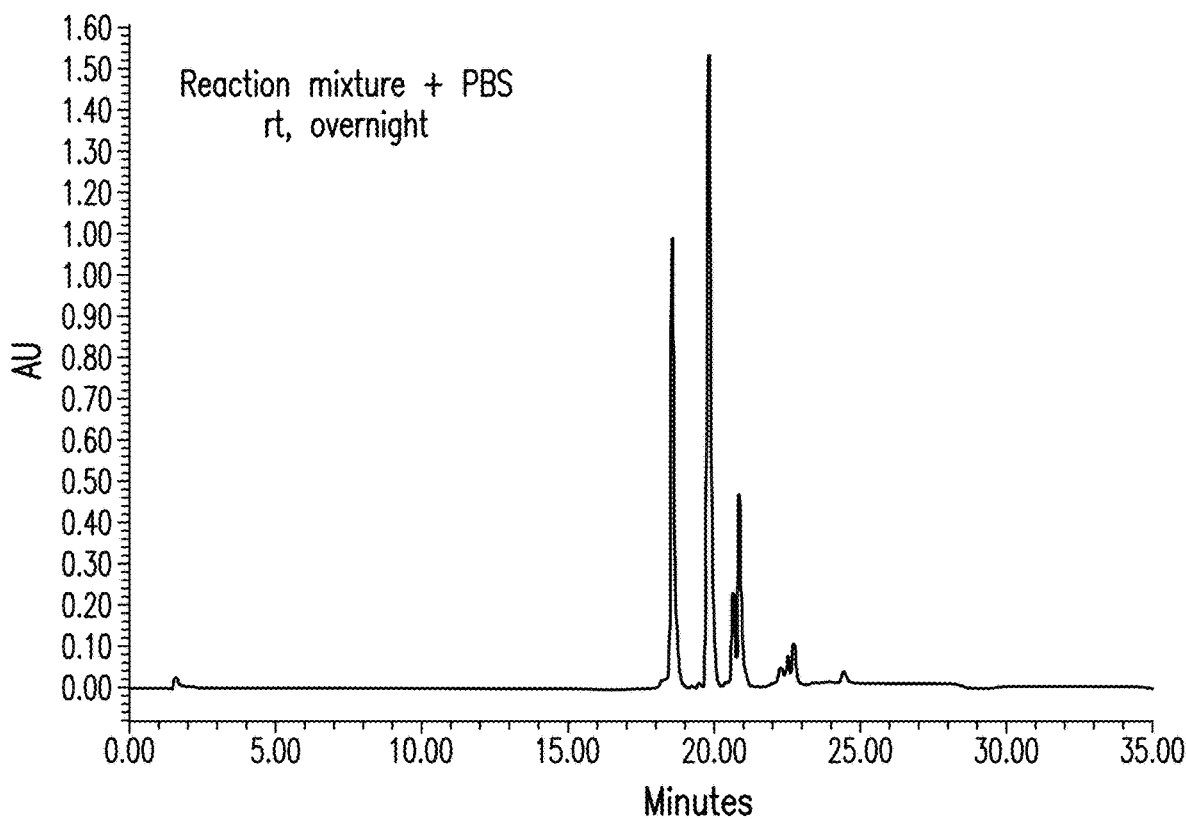

FIGS. 18A-18D. HPLC monitoring of RGD functionalization. FIG. 18A shows HPLC of RGD. FIG. 18B shows HPLC of Photo-ODIBO-PEG4-NHS. FIG. 18C shows HPLC of the reaction mixture of Example 13 after 30 minutes. FIG. 18D shows HPLC of the reaction mixture of Example 13 after addition of PBS and overnight incubation.

Figure 19:
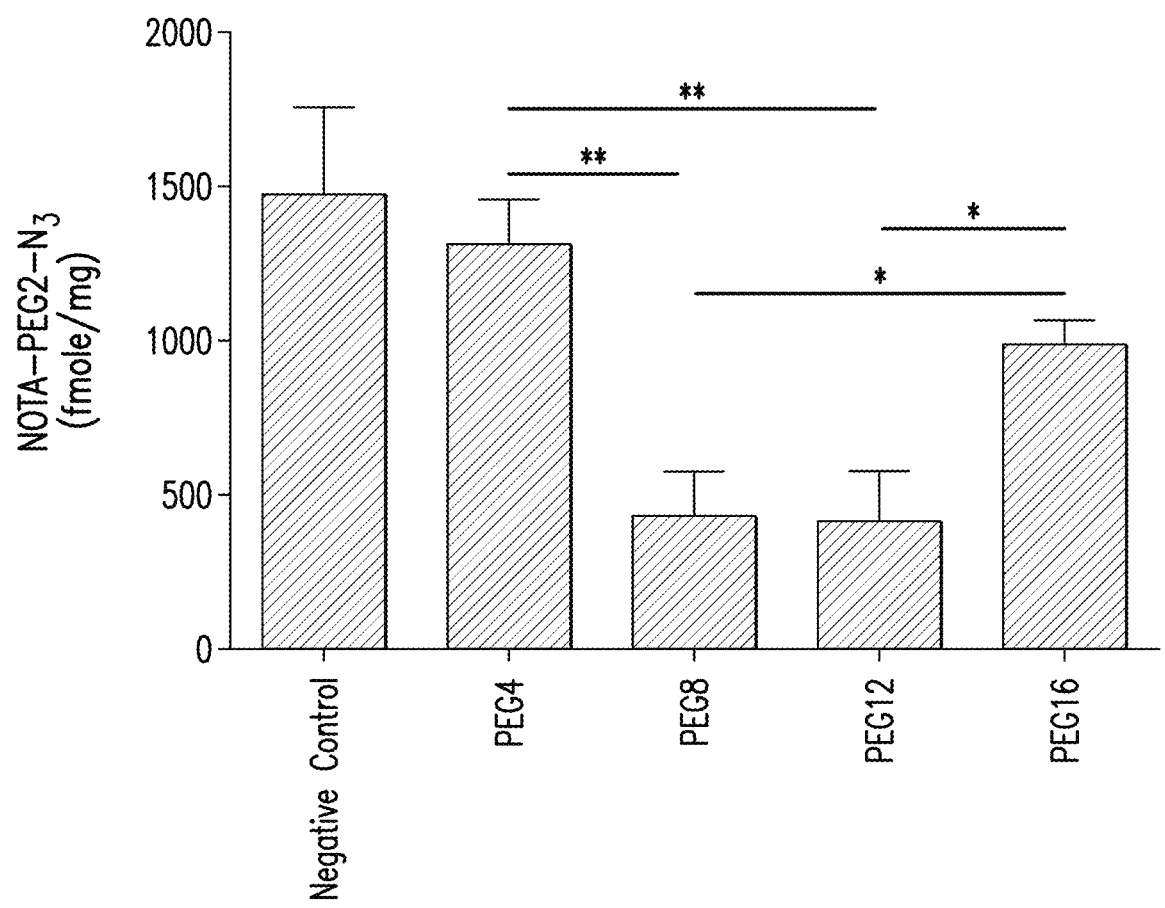

FIG. 19. In vitro screening of selected spacers via the developed platform. (*, P<0.05; **, P<0.01.)

Figure 20A:
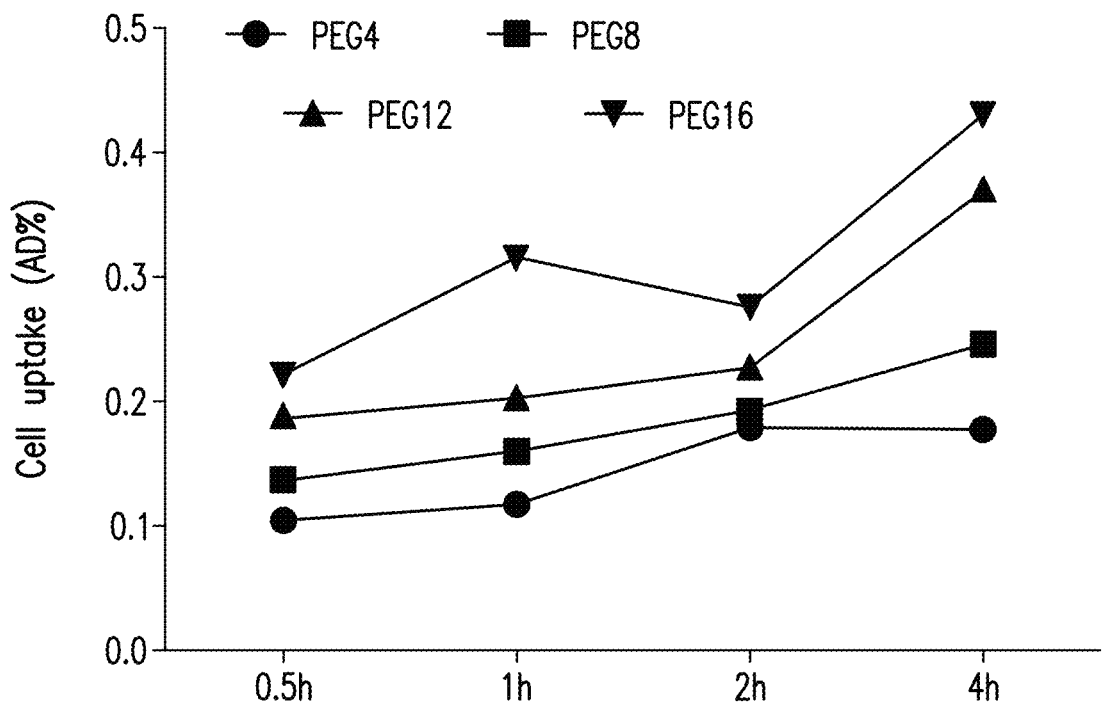
Figure 20B:
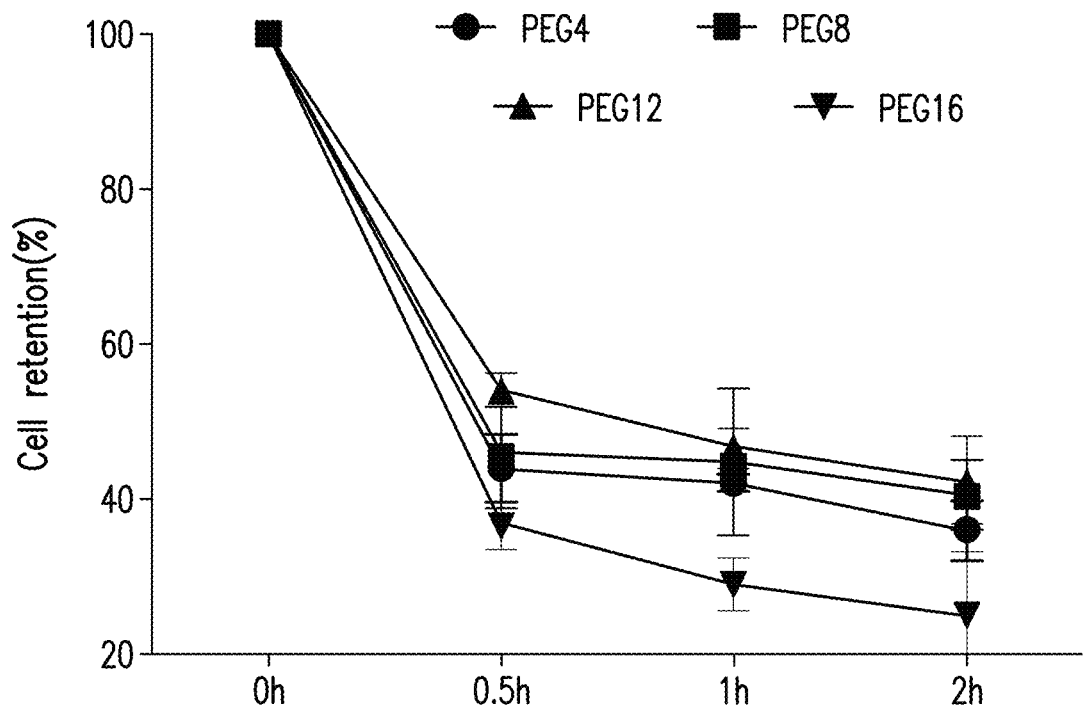

FIGS. 20A-20B. Cell uptake and efflux studies. FIG. 20A provides results of the cell uptake study for heterodimers with varied spacers according to Example 13.

FIG. 20B provides results of the cell efflux study for heterodimers with varied spacers according to Example 13.

Figure 21:
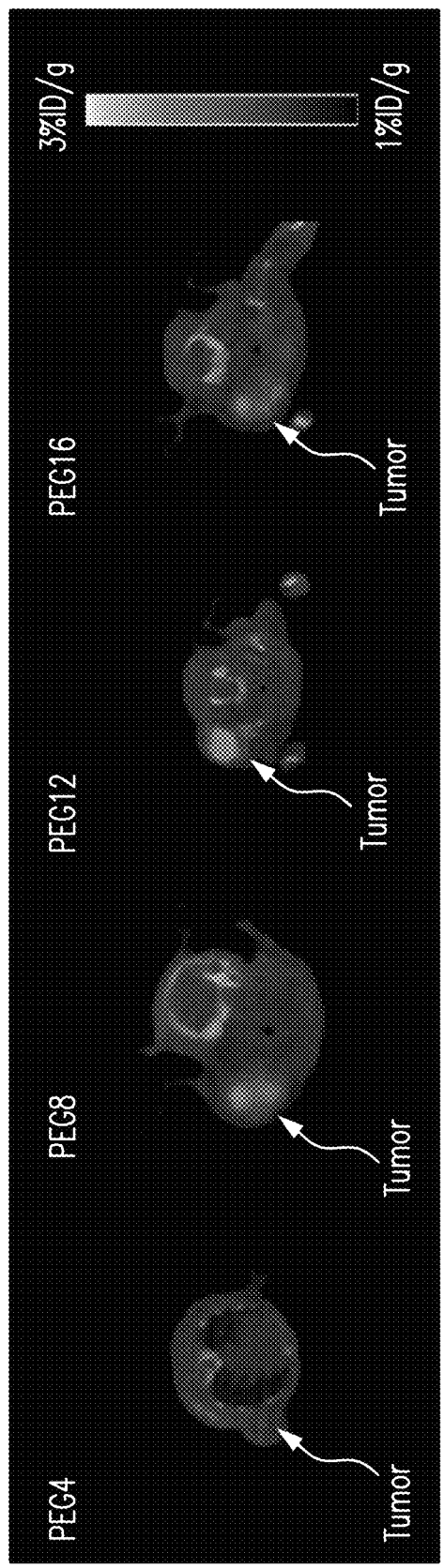

FIG. 21. PET imaging of the u87MG tumor using Ga$^{68}$ labeled heterodimers bearing the same length spacers as selected for the in vitro screening.

Figure 22:
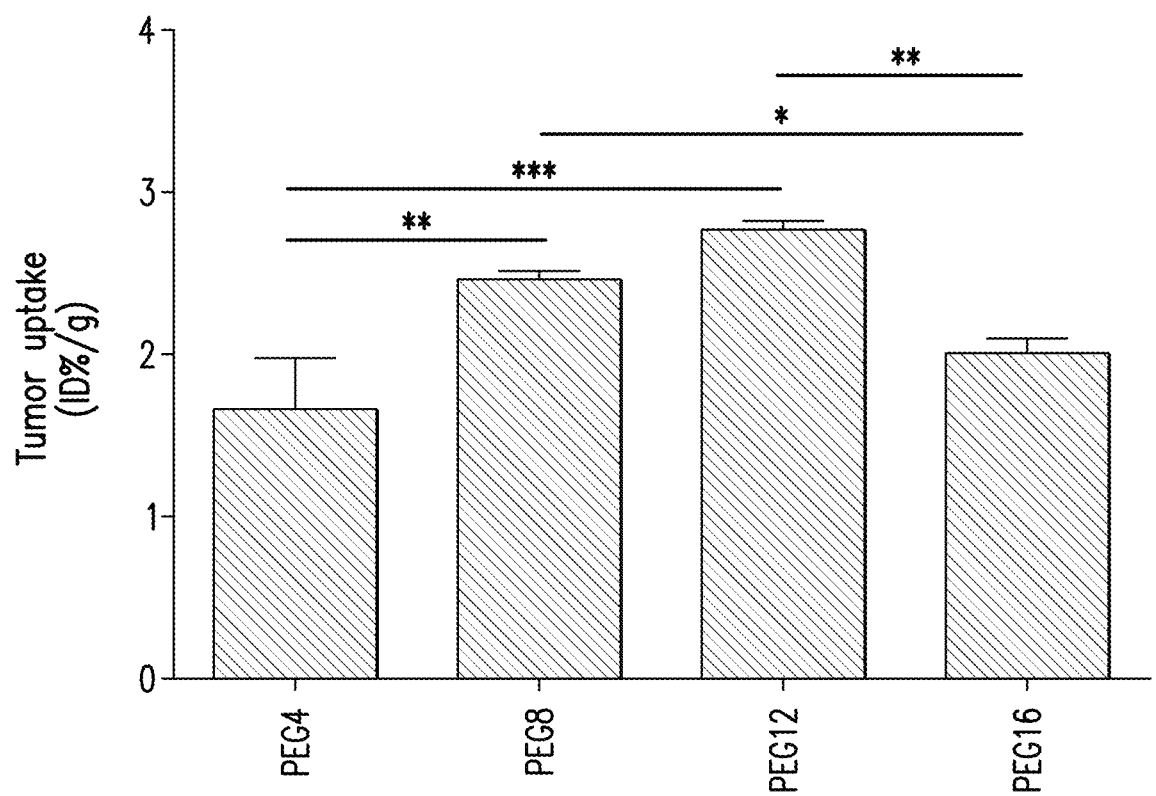

FIG. 22. ROI quantification based on PET images. (*, P<0.05; , P<0.01; *P<0.001).

Figure 23:
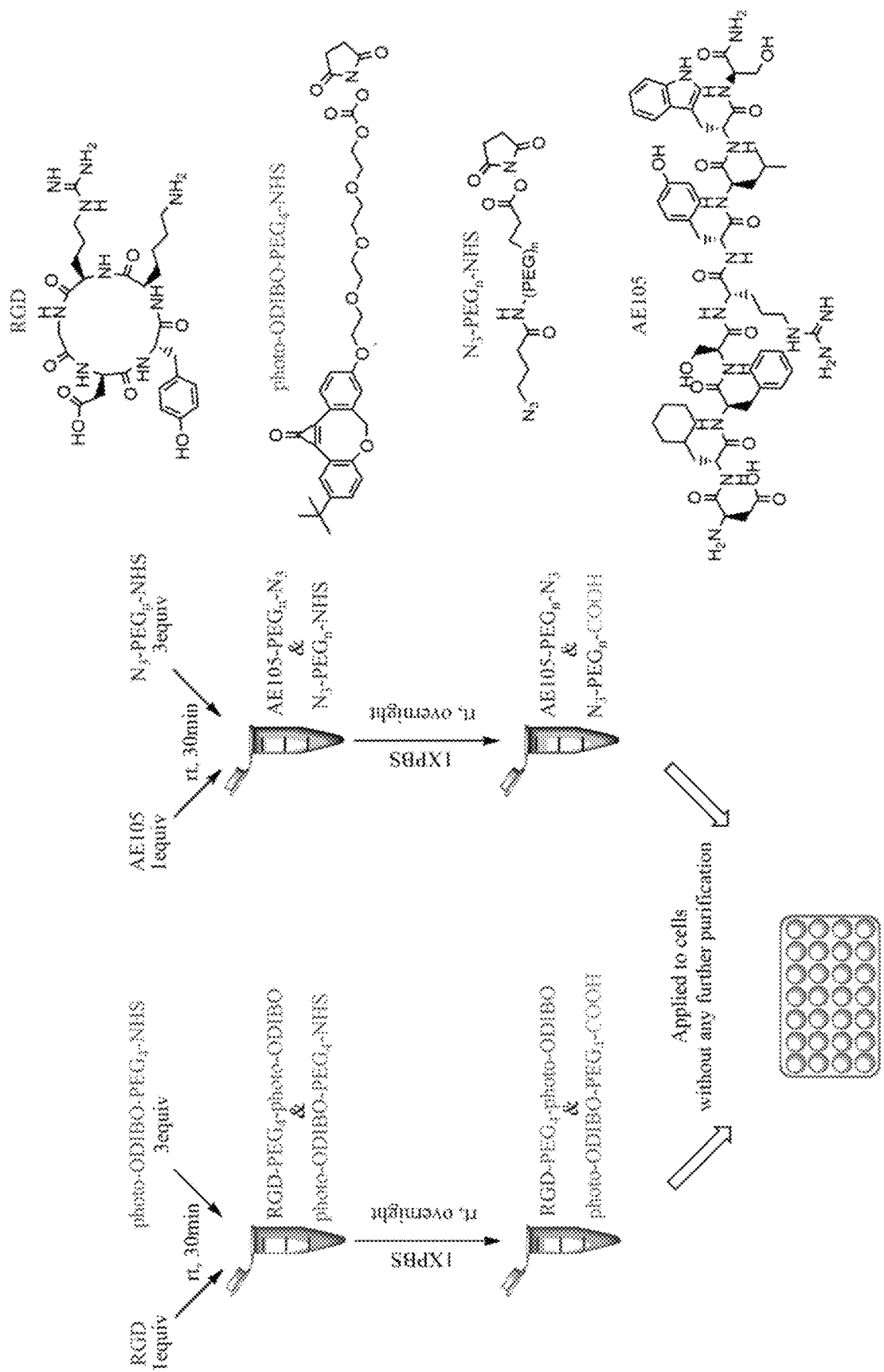

FIG. 23. A schematic of preparation of chemical tools used in the high-throughput screening platform described in Example 13.

5. DETAILED DESCRIPTION OF THE INVENTION

The present invention relates to compounds, kits, and methods for targeted molecular imaging and/or therapy, wherein targeting molecules interact with corresponding biomarkers on a biological subject. In certain non-limiting embodiments, the biological subject is a normal or diseased or degenerated cell, tissue, or other structure of interest. In certain non-limiting embodiments, the biological subject is a tumor or cancer cell. The present invention further relates to compounds/compositions/molecules/chelators and kits for targeted molecular imaging and/or therapy. The present invention also relates to in vitro high-throughput screening methods for identifying the appropriate spacer length for multivalent targeted molecular imaging and/or therapy compounds.

In certain non-limiting embodiments, the disclosed targeted molecular imaging and/or targeted drug delivery methods allow for prolonged retention of the fast-clearing detectable label and/or active agent, which consequently increases cellular uptake significantly. In certain non-limiting embodiments, the disclosed methods provide increased sensitivity and/or increased specificity. For example, the disclosed methods can convert low-affinity monovalent targeting molecule (~μM) into one with high avidity (~nM). In certain non-limiting embodiments, the disclosed targeted molecular imaging and/or targeted drug delivery methods can be broadly applied to various dual/multi-biomarker combinations and targets (e.g., tumors or cancer).

In certain non-limiting embodiments, the present invention provides a targeted molecular imaging and/or targeted drug delivery compound that binds more tightly to a cell of interest (e.g., a tumor or cancer cell) which can result in less non-specific binding and less false positive results. A tighter binding targeted molecular imaging and/or targeted drug delivery compound can result in smaller amounts of compound dissociating from the biological subject of interest. In certain non-limiting embodiments, the tighter binding compound increases cellular update and/or decreases uptake by non-targeted cells. By way of example, but not limitation, in the case of tumor cells, achieving high avidity can significantly enhance binding affinity on a tumor that overexpresses two targeted biomarkers simultaneously, but not increase the binding affinity on non-tumor tissues that express only one (or none) of the two targeted biomarkers, thus tumor/non-tumor ratio will increase significantly. In certain non-limiting embodiments, by increasing the local concentration of the targeting molecules due to increased total binding sites and by increasing the circulation time of the targeting molecules due to improved pharmacokinetic (such as clearance properties and excretion rates), the methods of the present invention provide a higher potential for clinical translation as the targeting ligand/molecule incorporated radioactive/drug molecule can accumulate at the site of interest, thereby increasing the uptake. For example, the density of targeted receptors can be increased by targeting an appropriate combination of complementary cell-surface receptors. In certain non-limiting embodiments, due to the change in size and lipophilicity, the multimers can also have improved pharmacokinetic performance.

In certain non-limiting embodiments, the invention provides a chelator for combining a targeting molecule to at least one of the same targeting molecule, at least one different targeting molecule, and/or a dye molecule. In certain non-limiting embodiments, the chelator is able to couple at least two targeting molecules. In certain non-limiting embodiments, the chelator is able to take part in solid phase peptide synthesis. In certain non-limiting embodiments, the chelator can simplify the process of developing targeted monomer, homodimers, heterodimers, and multimodalities as diagnostic tracers and/or radiotherapy agents.

In certain non-limiting embodiments, the invention provides an in vitro high-throughput screening platform for optimizing the length of spacers between the targeting molecules of the multimer. In certain non-limiting embodiments, the in vitro high-throughput screening platform is a sensitive assay which can utilize targeting molecules in the nM range for each test.

In certain non-limiting embodiments, the method combines click chemistry and radio chemistry to optimize the spacer length. In certain non-limiting embodiments, cells can be used as a screening platform via on-site (i.e., in vitro) formation of multimers (e.g., heterodimers). In certain non-limiting embodiments, the targeting molecules of the multimer can be functionalized separately with a reactive group (e.g. clickable group) and a photolabile group (e.g., clickable groups).

The term "biomarker", as used herein, refers to a marker (e.g., including but not limited to proteins (including monomeric and multimeric proteins, glycoproteins, lipoproteins, etc.), carbohydrates, lipids, nucleic acids and combinations thereof) that allows detection of a disease or disorder in an individual, including detection of disease or disorder in its early stages. Diseases or disorders include but are not limited to disorders of proliferation, including but not limited to cancer autoimmune conditions, degenerative conditions, vascular disorders, neurological disorders, and infectious diseases; biomarkers associated with numerous diseases and disorders in human and nonhuman animals are known in the art. In certain non-limiting embodiments, the presence or absence of a biomarker is determined by imaging. In certain non-limiting embodiments, the presence or absence of a biomarker in a biological sample of a subject is compared to a reference control.

The term "active agent" refers to an agent that is capable of having a physiological effect when administered to a subject. In certain non-limiting embodiments, the term "active agent" refers to a protein, peptide, small molecule, or radiopharmaceutical. In certain non-limiting embodiments, the active agent is a chemotherapeutic agent. In certain non-limiting embodiments, the active agent is an immunotherapeutic agent.

The term "therapeutically effective amount", as used herein, refers to that amount of active agent sufficient to treat, prevent, or manage a disease. Further, a therapeutically effective amount with respect to the second targeting probe of the disclosure can mean the amount of active agent alone, or in combination with other therapies, that provides a therapeutic benefit in the treatment or management of the disease, which can include a decrease in severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

The term "biological subject", as used herein, refers to, but is not limited to, a protein, virus, cell, tissue, organ or organism. In certain non-limiting embodiments, the biological subject can be a normal or diseased or degenerated or infected cell, tissue, or organ. In certain non-limiting embodiments, the cell can be a tumor or cancer cell.

The term "functionalized", as used herein, refers to a modification of an existing molecular segment to introduce a new functional group that is capable of undergoing a reaction with another functional group (e.g., an azide).

Ranges disclosed herein, for example "between about X and about Y" are, unless specified otherwise, inclusive of range limits about X and about Y as well as X and Y.

For clarity of description, and not by way of limitation, the detailed description of the invention is divided into the following subsections:
  (i) Targeted molecular imaging and/or drug delivery compounds and methods of use;
  (ii) Chelators and methods for making the targeted molecular imaging and/or drug delivery compounds;
  (iii) High-throughput screening platform for optimizing the length of spacers between the targeting molecules of the multimer;
  (iv) Biomarkers; and
  (v) Kits.

5.1. Targeted Molecular Imaging and/or Drug Delivery Compounds and Methods of Use The present invention provides targeted molecular imaging and/or targeted drug delivery compounds. In certain non-limiting embodiments, the invention provides two components or targeting molecules that each interacts with at least one biomarker (e.g., on a cell).

5.1.1. Targeting Molecules

The present invention provides for a targeted molecular imaging and/or targeted drug delivery compound having at least one first targeting molecule. In certain non-limiting embodiments, the invention provides for a targeted molecular imaging and/or targeted drug delivery compound having at least one first targeting molecule and at least one second targeting molecule. In certain non-limiting embodiment, the targeted molecular imaging and/or targeted drug delivery compound can have at least one, at least two, at least three, at least four, or at least five different targeting molecules directed to the same or different biomarkers. In certain non-limiting embodiment, the targeted molecular imaging and/or targeted drug delivery compound can have at one, two, three, four, five, or more targeting molecules. In certain non-limiting embodiment, the targeted molecular imaging and/or targeted drug delivery compound can have more than one of each targeting molecule.

In certain non-limiting embodiments, the targeting molecule can be an antibody, protein, peptide, small molecule, nanoparticle, polysaccharide, or polynucleotide that binds to the biomarker. In certain non-limiting embodiments, the targeting molecule is the active agent. In certain non-limiting embodiments, the targeting molecule can be internalizable or non-internalizable.

In certain non-limiting embodiments, the targeting molecule can be a protein. In certain non-limiting embodiments, the first targeting probe is an antibody. The term "antibody" as used herein, includes, but is not limited to antibodies, antibody derivatives, organic compounds derived there from, monoclonal antibodies, antibody fragments, modified antibodies, single chain antibodies and fragments thereof and miniantibodies, bispecific antibodies, diabodies, triabodies, or di-, oligo- or multimers thereof. In certain non-limiting embodiments, modified antibodies includes synthetic antibodies, chimeric or humanized antibodies, or mixtures thereof, or antibody fragments which partially or completely lack the constant region, e.g., Fv, Fab, Fab' or F(ab)'2 etc. In certain non-limiting embodiments, the antibody is a monoclonal antibody.

In certain non-limiting embodiments, the targeting molecule is commercially available. In certain non-limiting embodiments, the targeting molecule can be made against a specific biomarker by any technique understood by those of skill in the art.

In certain non-limiting embodiments, the targeted molecular imaging compound comprises one or two detectable labels. In certain non-limiting embodiments, the detectable label is an imaging label, and/or therapeutic probe.

In certain non-limiting embodiments, the imaging label can be, but is not limited to, $^{110}$In, $^{111}$In, $^{177}$Lu, $^{52}$Fe, $^{62}$Cu, $^{64}$Cu, $^{32}$P, 11C, $^{13}$N, 150, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, and other gamma-, beta- or positron-emitters. In certain non-limiting embodiments, the therapeutic probe is therapeutic radioisotope, such as but not limited to $^{67}$Cu, $^{177}$Lu, $^{90}$Y, $^{131}$I, $^{212}$Bi, $^{211}$At or $^{225}$Ac. In certain non-limiting embodiments, the therapeutic probe is an anticancer drug, such as, doxorubicin, paclitaxel, fluorouracil, etc.

In certain non-limiting embodiments, the targeted drug delivery compound comprises one or two active agents. In certain non-limiting embodiments, the active agent can be, but is not limited to, a protein, peptide, small molecule, peptide nucleic acid (PNA), or radiopharmaceutical.

In certain non-limiting embodiments, the detectable label is a dye molecule. In certain non-limiting embodiments, the compound can have more than one dye molecule. In certain non-limiting embodiments, the dye molecule is attached to one type of targeting molecule (one or more of the one type). In certain non-limiting embodiments, the dye molecule is attached to at least two types of targeting molecules (at least one of each). In certain non-limiting embodiments, the dye molecule can be, but is not limited to, cyanine dyes (Cy3, Cy3.5, Cy5, Cy7, Cy5.5, Cy7.5), GFP, Calcein, FITC, FluorX, Alexa dyes, Rhodamine dyes, 5-FAM, Oregon Green, Texas Red.

In certain non-limiting embodiments, the active agent can be, but is not limited to, trastuzumab, T-DM1, lapatinib, pertuzumab, cetuximab, panitumumab gefitinib, afatinib, dacomitinib, KD-019 erlotinib, cisplatin, carboplatin, gemcitabine, pemetrexed, irinotecan, 5-fluorouracil, paclitaxel, docetaxel, or capecitabine. In certain non-limiting embodiments, the radiopharmaceutical can be $^{111}$In-ibritumomab tiuxetan, $^{90}$Y-ibritumomab tiuxetan, $^{131}$I-tositumomab, $^{131}$I-labetuzumab, $^{131}$I-rituximab, $^{212}$Pb-trastuzumab, $^{131}$-trastuzumab, $^{111}$In-trastuzumab, $^{188}$Re-trastuzumab.

Table 1 below provides non-limiting examples of targeting molecules (i.e., the first targeting molecule and/or the second targeting molecule) that bind specific biomarkers.

TABLE 1

Examples of targeting molecules

| | Targeting Molecule | |
| --- | --- | --- |
| Biomarkers | antibody | peptide (or small molecule) ligand |
| CD13 | N/A | NGR (peptide) |
| Integrin α4β1 | N/A | LLP2A (peptide) |
| uPAR | N/A | AE105 (peptide) |
| | | AE105mut (peptide) |
| gastrin-releasing peptide (GRP) | N/A | BBN(7-14) (peptide) |
| SSTR2 | N/A | Tyr(3)-octreotate (peptide) |
| CCR5 | N/A | DAPTA (peptide) |
| Integrin αvβ3 | Etaracizumab | RGD (peptide) |
| | | RAD (peptide) |
| EGFR | Cetuximab | Erlotinib (small molecule) |
| VEGF | Bevacizumab | N/A |
| CA19-9 | 1116NS19-9, Human 5B1 | N/A |
| CD40 | CP-870,893 | N/A |
| PD-L1 | Atezolizumab | N/A |

The structure of LLP2A (CAS number 874148-50-2) is

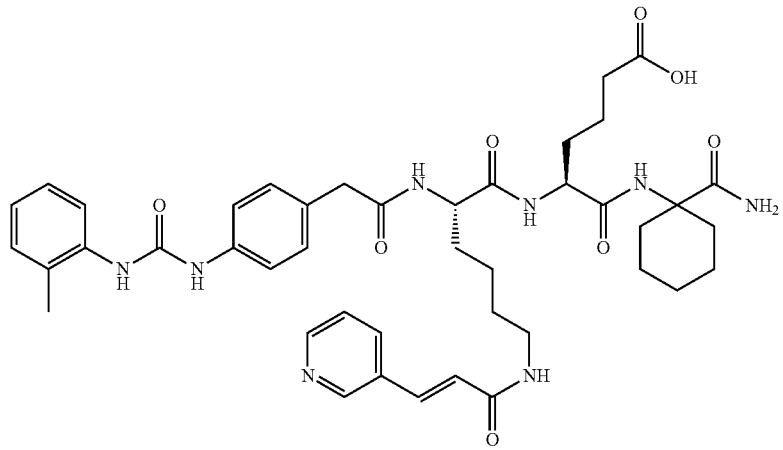 [SMILES: Cc1ccccc1NC(=O)Nc1ccc(CC(=O)N[C@@H](CCCCNC(=O)/C=C/c2cccnc2)C(=O)N[C@@H](CCCC(=O)O)C(=O)NC2(C(N)=O)CCCCC2)cc1]

In certain non-limiting embodiments, the targeted molecular imaging and/or targeted drug delivery compounds comprise at least one first targeting molecule, at least one second targeting molecule, and a detectable label and/or active agent. In certain non-limiting embodiments, the targeted molecular imaging and/or targeted drug delivery compounds comprise a first targeting molecule, a second targeting molecule, and a detectable label and/or active agent. In certain non-limiting embodiments, the targeted molecular imaging compounds comprise a first targeting molecule, a second targeting molecule, a detectable label, and optionally an active agent. In certain non-limiting embodiments, first targeting molecule and second targeting molecule can be a protein. In certain non-limiting embodiments, the detectable label can be an imaging label. In certain non-limiting embodiments, the imaging label can be $^{64}$Cu, $^{68}$Ga, or $^{18}$F. In certain non-limiting embodiments, the first targeting molecule can be, but is not limited to, uPAR targeting molecules. In certain non-limiting embodiments, the uPAR targeting molecule can be, but are not limited to uPA, ATF (amino terminal fragment of urokinase), AE105, or AE105mut. In certain non-limiting embodiments, the first targeting molecule can be, but is not limited to, a CD13 targeting molecule. In certain non-limiting embodiments, the CD13 targeting molecule can be, but is not limited to peptides containing the Asn-Gly-Arg (NGR) motif. In certain non-limiting embodiments, the CD13 targeting molecule can be a peptide such as, but is not limited to, cyclo(cNGRc), cyclo(cPNGRc), cyclo(NRGyK), linear cNGRc, or linear cPNGRc. In certain non-limiting embodiments, the second targeting molecule can be, but is not limited to, integrin αvβ3 targeting molecules. In certain non-limiting embodiments, the integrin αvβ3 targeting molecule can be, but is not limited to a protein with an exposed arginine-glycine-aspartic acid (RGD) tripeptide sequence or arginine-alanine-aspartic acid (RAD) sequence. In certain non-limiting embodiments, the integrin αvβ3 targeting molecule can be the peptide such as, but not limited to, cyclco (RGDyK) (RGD) or cyclo(RADyK) (RAD). In certain non-limiting embodiments, the biomarker can be, but is not limited to, CD13 and/or integrin αvβ3 (See e.g., FIG. 1). In certain non-limiting embodiments, the biomarker can be, but is not limited to, uPAR and/or integrin αvβ3.

In certain embodiments, the invention provides for the use of the above-described compounds for imaging a cell, tissue, or structure of interest in a subject in need of such treatment, for example a subject having a disease or disorder, at risk of having a disease or disorder, or being screened/tested for a disease of disorder. According to such methods, a subject is administered an effective amount of at least one first targeting molecule and a detectable label. In related embodiments, said subject may be further administered a second targeting molecule, and a chelator compound, as described above. Said method may be used, for example, to diagnose a tumor, an infection, a degenerative condition, etc. in a subject. In certain embodiments, said method may be used to determine the spread of disease, for example, the presence or absence of tumor metastasis or invasion in an organ or structure (e.g., bone).

5.1.2. Active Agent Delivery

In certain non-limiting embodiments, a subject is provided a therapeutically effective amount of a targeted drug delivery compound of the invention. In certain embodiments, the invention provides methods of treating a disease such as, but not limited to, cancer, congestive heart failure, diabetes, asthma, emphysema, infarction, ischemia, arteriosclerosis, toxicity, mental disease, depression or arrhythmia. One of skill in the art can select the proper biomarker(s) to target the active agent to the diseased cell.

Accordingly, in certain embodiments, the invention provides for the use of the above-described compounds for treating a disease or disorder of a subject or a cell, tissue or structure of interest in the subject comprising administering to the subject, an effective amount of at least one first targeting molecule and a detectable label. In related embodiments, said subject may be further administered a second targeting molecule, and a chelator compound, as described above.

In certain non-limiting embodiments, the subject includes any human or nonhuman animal. In certain non-limiting embodiments, the subject is a pediatric patient. In certain non-limiting embodiments, the subject is an adult patient. In certain non-limiting embodiments, nonhuman animal includes, but is not limited to, all vertebrates, e.g., mammals and non-mammals, such as nonhuman primates, sheep, dogs, cats, rodents, rabbits, horses, cows, chickens, amphibians, reptiles, etc.

In certain non-limiting embodiments, the targeted molecular imaging compound can be administered by, but not limited to, injection (e.g, intravenous, subcutaneous, intraperitoneally), infusion, inhalation, orally, topically, parenterally, transdermally, rectally or via an implanted reservoir.

5.1.3. Molecular Imaging

In certain non-limiting embodiments, after the administration of targeted molecular imaging compound, the subject is imaged. In certain non-limiting embodiments, imaging can be conducted by Positron Emission Tomography (PET), Single Photon Emission Computed Tomography (SPECT), Planar gamma camera, X-ray CT, planar X-ray, Magnetic Resonance Imaging (MRI), optical imager, or other diagnostic imaging technique.

In certain non-limiting embodiments, the subject includes any human or nonhuman animal. In certain non-limiting embodiments, the subject is a pediatric patient. In certain non-limiting embodiments, the subject is an adult patient. In certain non-limiting embodiments, nonhuman animal includes, but is not limited to, all vertebrates, e.g., mammals and non-mammals, such as nonhuman primates, sheep, dogs, cats, rodents, rabbits, horses, cows, chickens, amphibians, reptiles, etc.

The targeted molecular imaging compound can be administered by the same routes as disclosed for the targeted drug delivery compound.

5.2 Chelators and Methods for Making the Targeted Molecular Imaging and/or Drug Delivery Compounds The present invention provides targeted molecular imaging and/or targeted drug delivery compounds. In certain non-limiting embodiments, the invention provides two components or targeting molecules that each interacts with at least one biomarker (e.g., on a cell). In certain non-limiting embodiments, a chelator can be used to attach various moieties of the targeted molecular imaging and/or targeted drug delivery compounds. For example, the chelator can attach various targeting molecules together (see FIG. 2 by way of example). In certain non-limiting embodiments, the chelator can also attach the detectable label, dye molecule, and/or active agent to at least one targeting molecule. In certain non-limiting embodiments, the chelator can also attach the detectable label, dye molecule, and/or active agent to at least two targeting molecules.

In certain non-limiting embodiments, the chelator can be bound to one targeting molecule. In certain non-limiting embodiments, the chelator can be bound to two targeting molecules. In certain non-limiting embodiments, the chelator can be bound to more than one of the same targeting molecules. In certain non-limiting embodiments, the chelator can be bound to more than one type of targeting molecule. In certain non-limiting embodiments, the chelator can be bound to two types of targeting molecule.

In certain non-limiting embodiments, the chelator can be bound to one targeting molecule (e.g., either the first or second targeting molecule) for monomers. In certain non-limiting embodiments, the chelator can be bound to two of the same targeting molecules (e.g., either two of the first or two of the second targeting molecule) for homodimers. In certain non-limiting embodiments, the chelator can be bound to two different targeting molecules (e.g., the first and second targeting molecules) for heterodimers. In certain non-limiting embodiments, the chelator can be bound to one targeting molecule (e.g., either the first or second targeting molecule) and one dye molecule for multimodalities.

In certain non-limiting embodiments, the chelator can be attached to one or more of the targeting molecules via a spacer. In certain non-limiting examples, the spacer can be a polymer or a biomolecule. In certain non-limiting embodiments, the polymer can be synthetic or natural. In certain non-limiting examples, the polymer can be polyethylene glycol (PEG). For example, the polymer can have a molecular weight of between about 5 and 40 Da, about 40 Da, up to about 100 Da, up to about 200 Da, up to about 300 Da, up to about 400 Da, up to about 1,000 Da, up to about 10,000 Da, up to about 25,000 Da, up to about 30,000 Da, up to about 35,000 Da, or up to about Da 40,000, or for further example, from about 40 Da to about 100,000 Da, from about 40 Da to about 5,000 Da, from about 40 Da to about 10,000 Da, from about 40 Da to about 25,000 Da, from about 1,000 Da to about 25,000 Da, from about 200 Da to about 100,000 Da, from about 10,000 Da to about 100,000 Da, from about 25,000 to about 100,000 Da, or from about 25,000 Da to about 50,000 Da. For further example, the polymer can be polyacrylic acid; hydroxyethyl starch (HES); poly lactide-co-glycolide; poly-D, L-p-dioxanonepoly lacticacid-ethylene glycol block copolymer (PLA-DX-PEG); poly (ortho) esters; poly-glutamate; polyaspartates; a polymer of α-β-unsaturated monomers, such as (meth) acrylic acid, crotonic acid, maleic acid, maleic anhydride, fumaric acid, itaconic acid or anhydride, etc.; a comonomer comprising vinyl ethers, vinyl esters, vinylamine amides, olefins, diallyl dialkyl ammonium halides, preferably vinyl ether; poly (diethylenglycoladipat); polyethyleneimine; polyglycolide; polyurea; Polylimonen (or Polylimo); poly (2-methyl-1, 3-propylene adipate); a graft polymer; graft (block) polymer with other polymers. In certain non-limiting embodiments, the polymer is linear, branched, or dendrimic.

In certain non-limiting embodiments, the polymer is PEG. In certain non-limiting embodiments, the PEG spacer can have a molecular weight of about 44 Da to 20 kDa. In certain non-limiting embodiments, the PEG spacer can comprise non-PEG portions and/or non-PEG monomers.

In certain non-limiting embodiments, the spacer can comprise about 2 to about 30 monomers. In certain non-limiting embodiments, the spacer can comprise about 2 to about 20, about 2 to about 10, about 4 to about 10, about 4 to about 9, about 4 to about 8, about 4 to about 7, about 4 to about 6, or about 4 to about 5 monomers. In certain non-limiting embodiments, the spacer can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 55, at least 26, at least 27, at least 28, at least 29, or at least 30 monomers. In certain non-limiting embodiments, the spacer can comprise about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 monomers.

In certain non-limiting embodiments, the chelator comprises a mutlifunctional chelator having general Formula I:

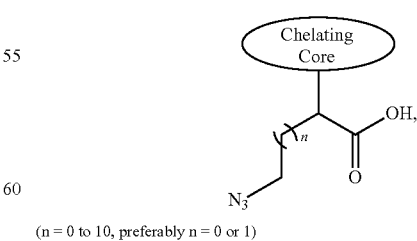

(n = 0 to 10, preferably n = 0 or 1)

where the chelating core groups is selected from NOTA, NETA, CB-TE2A, CB-TE1A1P, TETA, Pycu2A, DiAmSar, DOTA, DTPA, PCTA, DFO, etc.

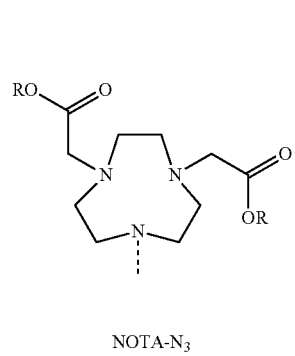
NOTA-N₃
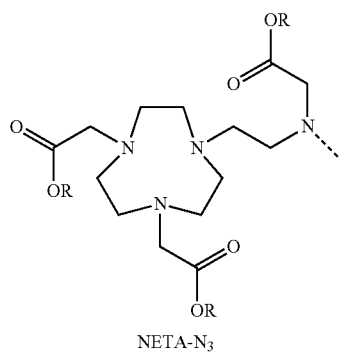
NETA-N₃
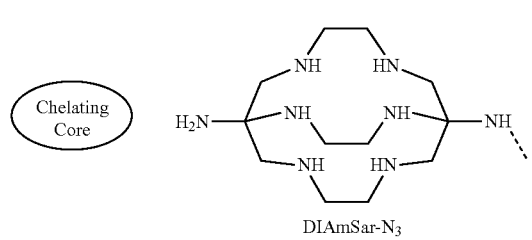
DIAmSar-N₃
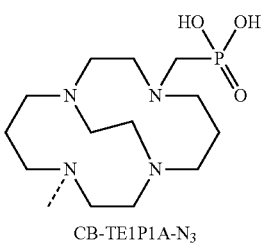
CB-TE1P1A-N₃
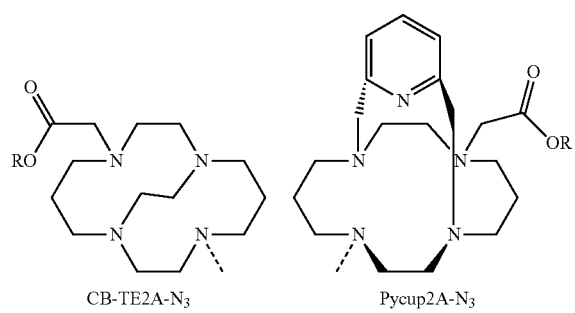
CB-TE2A-N₃
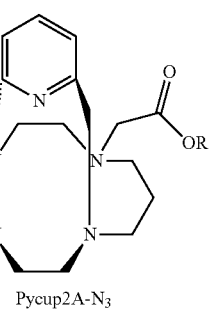
Pycup2A-N₃
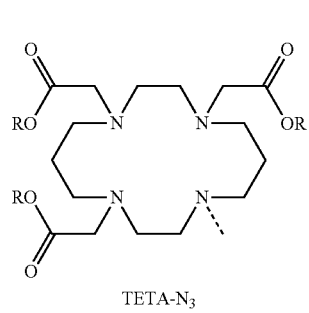
TETA-N₃
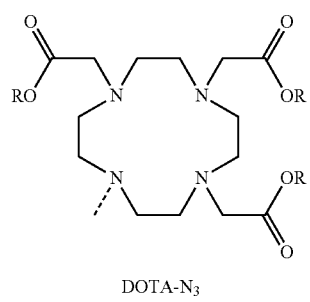
DOTA-N₃
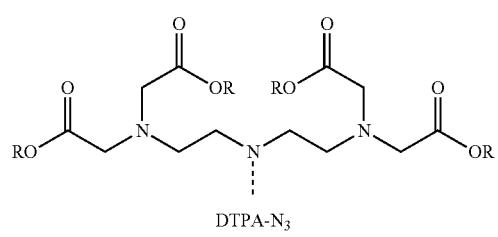
DTPA-N₃
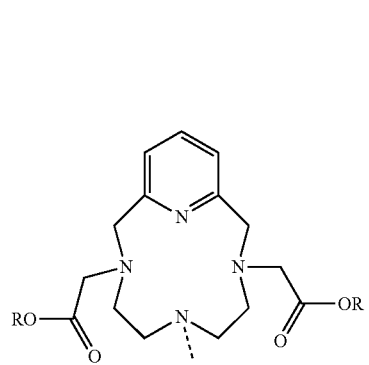
PCTA-N₃
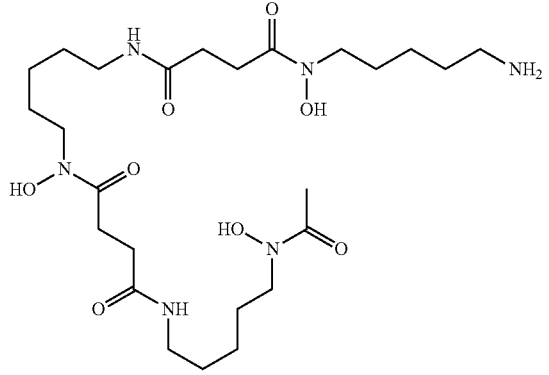
DFO-N₃

In certain embodiments, the chelating core is a group that can coordinate certain metal ions and form a stable chelate. The chelating core is the key group for complexing radiometal. In certain non-limiting embodiments, the chelator combines a carboxylic acid or active ester group for amide bond connection, and an azide group suitable for azide-alkyne based click chemistry, in addition to a chelating core that can coordinate with a radioistope, such as $^{64}$Cu, $^{68}$Ga, Al$^{18}$F, etc. In certain non-limiting embodiments, the chelator comprises a 1, 4, 7-triazacyclonenonane (TACN)-based chelator. In certain non-limiting embodiments, the chelator comprises a 1,4,7,10-tetraazacyclododecane(cyclen)-based chelator. In certain non-limiting embodiments, the chelator comprises a 1,4,8,11-tetraazabicyclo[6.6.2]hexadecane-based chelator. In certain non-limiting embodiments, the chelator comprises NOTA, DOTA, L-NETA, $N_3$—NO$^t$B$_2$ or $N_3$-DO$^t$B$_3$. Examples 1 and 2 provide sample synthetic schemes in accordance with the present invention.

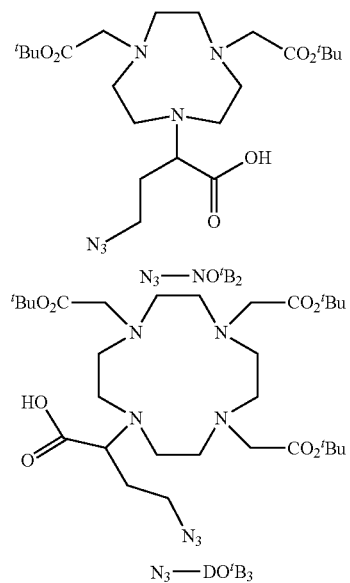

In addition to the metal chelating core, the disclosed chelator can contain two bioorthogonal functional groups: carboxylic acid group and azide group for attaching the first targeting molecule via assisted amide formation and the second targeting molecule (or, detectable label, or active agent) via click chemistry, respectively. Compared to other molecule chelators containing one functional group only, these newly developed bifunctional chelators (BFCs) demonstrated several advantages. First, the synthetic strategy can be more straightforward due to the use of a BFC that serves as both a chelator and a spacer; therefore, extensive protection and/or deprotection and/or multifunctional spacer preparation is not required. Secondly, condition optimization is not needed because the reactions (SPPS and click reaction) can easily be completed in nearly quantitative yield, which facilitates the ease of preparations. Maximum utilization of SPPS and click reaction allows for the use of only one chromatography purification step to obtain a pure imaging probe. Finally, this is a universal and robust platform that can be applied to prepare the multivalent and multimodal imaging probes containing any interested ligand(s), dye(s) and other functional moieties, not limited to the ones exemplified here.

In certain non-limiting embodiments, the chelator can be modified to be suitable for use for solid phase peptide synthesis (SPPS) by reducing the azide to amide group using commonly-used reduction agents such as PPh3. SPPS is based on the amide forming reaction between carboxylic acid and an amino group. The reduction of an azide provides an amino group for the following amino acid conjugation. Thus, with an amino group, the chelator is compatible to the SPPS system. In certain non-limiting embodiments, automatic peptide synthesis can be used to simplify the synthesis process after on-resin reduction of azide group to amide group. The automatic peptide synthesis works on the same principle as SPPS, which can save time and effort.

In certain non-limiting embodiments, the chelator can be synthesized by conjugating an active pendant arm, bearing both an azide group and a acarboxylic acid or ester group, to a chelating core by a nucleophilic substitution reaction.

In certain non-limiting embodiments, the detectable labels can be attached by incubating the chelator with radionuclides. In certain non-limiting embodiments, the second detectable labels can be attached by reacting the chelator with dye through click chemistry, esterification reaction, amidation reaction, or another conjugating reaction.

In certain non-limiting embodiments, the active agent can be added by reacting the chelator with the active agent through click chemistry, esterification reaction, amidation reaction, or another conjugating reaction.

5.2. High-Throughput Screening Platform for Optimizing the Length of Spacers Between the Targeting Molecules of the Multimer In certain non-limiting embodiments, the invention provides an in vitro high-throughput screening platform for optimizing the length of spacers between the targeting molecules of the imaging and/or targeted drug delivery compounds. In certain non-limiting embodiments, the in vitro high-throughput screening platform is a sensitive assay that only utilizes targeting molecules in the nM range for each test. Using fewer targeting molecules can reduce the cost of the screening assay. In certain non-limiting embodiments, the invention provides reactions involving only one to two steps. FIG. 3 is a non-limiting example of an in vitro high-throughput screening assay of the invention.

In certain non-limiting embodiments, the method combines click chemistry and radio chemistry to optimize the spacer length. In certain non-limiting embodiments, cells can be used as a screening platform via on-site formation of targeted molecular imaging and/or targeted drug delivery compounds. In certain non-limiting embodiments, the targeting molecules of the targeted molecular imaging and/or targeted drug delivery compounds can be functionalized separately with a nonactivated photolabile functional group (i.e., photo-triggerable functional group) or a reactive functional group that binds to the photoliable functional group once activated by a photon generating source.

In certain non-limiting embodiments, the high-throughput screening platform comprises exposing cells to a first functionalized targeting molecule and a second functionalized targeting molecule, wherein either the first functionalized targeting molecule and/or second functionalized targeting molecule comprises spacers of different lengths between the targeting molecule and the reactive functional group. In certain non-limiting embodiments, either the first functionalized targeting molecule or second functionalized targeting molecule comprises spacers of a set length between the targeting molecule and the reactive functional group.

In certain non-limiting embodiments, the cells are exposed to photon energy to activate a nonactivated photolabile functional group, which allows the two targeting molecules to be linked via their respective spacers. In certain non-limiting embodiments, the assay can be quenched with excess radio-metal labeled chelators that are able to bind to the unbound activated photolabile functional group. In certain non-limiting embodiments, the amount of bound radio-metal labeled chelators can be measured. In certain non-limiting embodiments, the decrease in measured radioactivity indicates that the spacer length is appropriate or optimized.

In certain non-limiting embodiments, the first functionalized targeting molecule comprises a photolabile functional group. In certain non-limiting embodiments, the photolabile functional group can be, but is not limited to, Photo-OIDBO or Photo-tertrazole.

In certain non-limiting embodiments, and the second functionalized targeting molecule comprises a reactive functional group that only binds to the photolabile functional group once the photolabile functional group has been exposed to photon energy. In certain non-limiting embodiments, the reactive functional group of the second functionalized targeting molecule can be, but is not limited to, an azide or an alkene.

5.2.1. Preparation of Multivalent Compounds

In certain non-limiting embodiments, the first functionalized targeting molecule is a Nonactivated Photolabile Functional Group-(Monomer) n-Targeting Molecule (exemplified as p-ODIBO in FIG. 3) that comprises spacers (e.g., PEG) of various monomer lengths. In certain non-limiting embodiments, the spacer can comprise about 2 to about 30 monomers (as discussed above). For example, but not by way of limitation, n can equal 2, 4, 6, 8, 10, 12, 14, 16, 18, 20, or 30 monomers. In certain non-limiting embodiments, the Nonactivated Photolabile Functional Group-(Monomer) n-Targeting Molecules can be prepared by first forming $NH_2$-(Monomer) n-Targeting Molecules by adding Boc-(Monomer) n-NHS to the targeting molecule of interest followed by Boc deprotection. For example, the Boc-(Monomer) n-NHS can be combined with the targeting molecule in a suitable buffer (e.g., phosphate buffered saline (PBS)) followed by deprotection with trifluoroacetic acid (TFA) (e.g., 95%). The prepared NH2-(Monomer) n-Targeting Molecule can then be mixed with Nonactivated Photolabile Functional Group-NHS to produce Nonactivated Photolabile Functional Group-(Monomer) n-Targeting Molecules.

In certain non-limiting embodiments, the second functionalized targeting molecule is a Reactive Functional Group-Spacer-Targeting Molecule (exemplified as $N_3$ in FIG. 3), which comprises a spacer with a set monomer length. In certain non-limiting embodiments, the spacer can comprise about 2 to about 30 monomers (as discussed above). For example, but not by way of limitation, the spacer can be 4 or 8 monomers. In certain non-limiting embodiments, the reactive functionalized targeting molecule can be prepared by mixing the targeting molecule and Reactive Functional Group-Spacer-NHS in a suitable buffer (e.g., PBS).

In certain non-limiting embodiments, the reactive functionalized targeting molecule comprises spacers of different lengths rather than the photolabile functionalized targeting molecule. As one non-limiting example, it can be more convenient to test the spacer length using a reactive functionalized targeting molecule instead of a photolabile functionalized targeting molecule, as the former can be easier to prepare.

By way of example, and not limitation, the photolabile functionalized targeting molecule can be a photo-ODIBO-PEGn-RGD peptide (e.g., n=2, 4, 6, 8, 10, 12, 14, 16, 18, 20). Also by way of example, and not limitation, the reactive functionalized targeting molecule can be N3-PEGn-AE105 and/or N3-PEGn-NGR peptides.

5.2.2. In Vitro High-Throughput Assay

In certain non-limiting embodiments, Reactive Functional Group-Spacer-Targeting Molecules can be mixed with one set of Nonactivated Photolabile Functional Group-(Monomer) n-Targeting Molecules with a spacer having a particular monomer length. For example, in such embodiments, there can be one mixture of each spacer length combination. In certain non-limiting embodiments, Nonactivated Photolabile Functional Group-Spacer-Targeting Molecules can be mixed with one set of Reactive Functional Group-(Monomer) n-Targeting Molecules with a spacer having a particular monomer length. In certain non-limiting embodiments, the reactive functionalized targeting molecules and nonactivated photolabile functionalized targeting molecules can be mixed in about a 1:1 molar ratio to prepare mixed-targeting molecule stock solutions. This ratio can be adjusted depending on the densities of the two targeted receptors. In certain non-limiting embodiments, each reaction mixture comprises functionalized targeting molecules each with one specific spacer length.

In certain non-limiting embodiments, one of the mixed-targeting molecule stock solutions can be added to cells comprising the biomarkers of interest. It is desirable to have a large excess of targeting molecules present. In certain non-limiting embodiments, after the targeting molecules bind to the targeted biomarker, the unbound targeting molecules will be washed off (e.g., using a suitable buffer).

In certain non-limiting embodiments, the cells are exposed to photon energy (including but not limited to laser and/or other light sources) for between, for example, about 1 min and 1 hour (inclusive), i.e., for a period of time effective to convert the nonactivated photolabile functional group on the functionalized targeting molecule to the activated photolabile functional group.

In certain non-limiting embodiments, radiolabeled reactive functional groups that bind to the activated photolabile functional group are added to the cells. In certain non-limiting embodiments, the cells are incubated 2-4 hours before adding the radiolabeled reactive functional group. In certain embodiments, the radiolabeled functional group can be a N3-Radioactive Element-Chelator (e.g., N3-($^{64}$Cu) NOTA), and can, in non-limiting embodiments, be added 2-4 hours after the photo irradiation to allow sufficient time for the click reaction between two different targeting molecules. The purpose of adding this N3-Radioactive Element-Chelator is to detect the amount of non-reacted photolabile functional group for measuring the extent of the click reaction between the two different targeting molecules. In certain non-limiting embodiments, the radiolabeled reactive functional groups bind to the "excess" activated photolabile group that is bound to the biomarker but did not bind to the reactive group of a functionalized targeting molecule.

In certain non-limiting embodiments, the cells are washed with an appropriate buffer to remove excess radiolabeled reactive groups before detecting the level of radioactivity by methods known to those of skill in the art. In certain non-limiting embodiments, the combination of functionalized targeting molecules with the lowest radio-counts, containing the lowest "excess" radiolabeled reactive groups, indicates that the corresponding spacers are of an appropriate or optimal length.

By way of example, and not limitation, the Reactive Functional Group-Spacer-Targeting Molecule (e.g., N3-PEG4-AE105) can be mixed with one or more (e.g., about ten) Nonactivated Photolabile Functional Group-(Monomer) n-Targeting Molecules (e.g., photo-ODIBO-PEGn-RGD peptides; n=2, 4, 6, 8, 10, 12, 14, 16, 18, 20) in a 1:1 molar ratio to prepare one or more (e.g., about ten) mixed-targeting molecules stock solutions. Each of the mixed-targeting molecules stock solutions can be added to separate cell culture wells pre-seeded with cells and the cells can be incubated with the mixed-targeting molecules (e.g., until binding equilibrium is achieved). In certain embodiments, the cells are pre-seeded in 24, 48, 96, 384, or 1536 well plates. Following incubation with the mixed targeting molecules, the cells can be washed with a suitable buffer (e.g., PBS) to remove unbound targeting molecules. The cells can then be exposed to photon energy (e.g., a UV lamp (365 nm)) to activate the photolabile functional group (e.g., to generate azide-active "ODIBO"), subsequently triggering ligation between the reactive group and the activated photolabile group (e.g., N3-PEGn-AE105 and ODIBO-PEGn-RGD) bound to the biomarkers on the cells. Following incubation to allow the two targeting molecules to bind (e.g., 2-4 hours), radiolabelled reactive groups (e.g., N3-($^{64}$Cu) NOTA) can be added to the cells, which will bind to the activated photolabile groups not bound to the reactive groups of the functionalized targeting molecules. The unbound radiolabelled reactive group can be washed away, and the plate of cells can be processed to be read with a plate reader (e.g., a high-throughput MicroBeta2 Plate Counter) to measure the radiolabelled reactive groups.

5.2.3. Cell Lines

In certain embodiments, this method can be applied using various cell cultures, including but not limited to, primary cell cultures, tissue explants, or transformed cell cultures known in the art. Non-limiting examples of such cell cultures include: Primary-hBM SC; Primary-hSkin FB; Primary-cow CC; Primary-rat BMSC; Primary-h CC; MC3T3-E1; Primary-hUVEC; Primary-rabbit CC; NIH 3T3; Primary-CC; Primary-rat Liver Hep; Primary-hSkin Keratinocyte; MG63; HEP-G2; L929; Primary-BM SC; Primary-rabbit BM SC; Primary-pig CC; Primary-hBone OB; MCF-7; Primary-rat Heart CM; Primary-h Foreskin FB; Primary-hAdipose SC; Primary-hFB; Primary-hAdipose SC; Primary-FB; Primary-ratAortaSMC; Primary-Bone; Primary-dog CC; 3T3 (nonspecific); C2C12; MDA-MB-231; SaOS-2; Primary-mouse BM SC; Primary-rat CC; Primary-h Mesoderm Mes Pre C; Primary-rat Brain Neuronal; PC12; Primary-Cancerous; Primary-h Skin EC; Primary-rat BM OB; Primary-mouse Embryo SC; MCF-10A; Primary-h Bone OB-like; Primary-goat BMSC; Primary-h Aorta SMC; MDCK (Madin-Darby Canine Kidney); Primary-hi DAnnulus C; Primary-ratBone OB; Primary-h Adipose Preadipocyte; Primary-SC; Primary-rat Skeletal Muscle Myoblast; Primary-Heart CM; Primary-cow AortaEC; Primary-dog BM SC; Primary-sheep BM SC; Primary-sheep CC; Primary-pig BMSC; Primary-cow BMSC; Primary-h BladderSMC; Primary-pig Aorta EC; Primary-h Cornea Epi C; Primary-h Aorta EC; Primary-h Cornea FB; Primary-pig Aorta SMC; Primary-mouse Liver Hep; A549; Primary-Bone OB; Primary-h Bladder Uro; Primary-h UV SMC; Swiss 3T3; Primary-Liver Hep; Primary-h Lig FB; Primary-h Coronary Artery SMC; Primary-OB-like; Primary-h Teeth Mes Pre C; HT1080; Primary-rat Heart FB; Primary-pig HV Intersticial C; C3A; Primary-h Breast Cancerous; Primary-h Foreskin Keratinocyte; Primary-h Oral Mucosa Keratinocyte; Primary-mouse Ovary Oocytes; Primary-h Vase SMC; 3T3-L1; Primary-h Lung FB; Primary-chicken Ganglia Neuronal; Primary-h U CStC; Primary-cow Aorta SMC; Primary-mouse Embryo FB; Primary-h Bronchi EpiC; CHO-K1; Primary-h Liver Hep; Primary-hSaphVEC; Primary-hTeethPDL; Primary-rat Skin FB; Primary-pig Liver Hep; PC-3; Primary-SMC; Primary-hMVEC; Primary-mouseFB; Primary-h Nasal Chondrocyte; Primary-hCorneaKeratinocyte; Primary-hOvaryCancerous; Primary-h U CBSC; Primary-rat Heart EC; Primary-Vasc; Primary-mouse Skin FB; Primary-h Tendon TC; Primary-rat Brain Astrocyte; Primary-rat Nerve SC; Ha CaT; Primary-h Gingiva FB; Primary-Neural; Primary-cow Bone OB; Primary-rat Adipose SC; Primary-mouse Bone OB; Primary-h Teeth PC; Primary-h Blood Mononuclear; Primary-rat Hippocampus Neuronal; D3; HeLa; HEK293; C17.2; Primary-h Skin Melanocyte; Primary-h Blood EC-like; HOSTE85; Primary-h UC SC-like; Primary-h Cornea SC; Primary-rat Aorta EC; Primary-h Saph VSMC; Primary-h UCBEC; Primary-mouse Heart CM; D10RL UVA; Primary-h Coronary Artery EC; Primary-h Aorta Myo FB; HT-29; Primary-h Tendon FB; RAW 264; Primary-rat Dental Pulp SC; 3T3-J2; H1; Primary-pig Teeth; Primary-rat Sciatic Schwann; Primary-rabbit Bone OB-like; Primary-sheep Aorta EC; Primary-rabbit Cornea Epi C; Primary-h Ovary Epi C; Primary-rabbit Ear Chondrocyte; SH-SY5Y; Primary-h Teeth FB; Primary-h Oral Mucosa FB; Primary-rabbit FB; C6; Primary-rat Testes Stertoli; Primary-cow Arterial EC; Primary-pigHVEC; Primary-cow Nucleus Pulposus Cells; Primary-rat Ganglia Neuronal; Primary-dog Bladder SMC; Primary-Vasc SMC; 129/SV; Primary-pig Ear Chondrocyte; ED27; Primary-rabbit Bone B; Primary-h Brain Glioblast; Primary-rat Adipose Preadipocyte; Primary-h Cartilage Synov; Primary-rat Pancreas Insulin; Primary-hEC; Primary-sheep Aorta SMC; Primary-h Endometrium EpiC; U251; Primary-h Endometrium StC; Primary-pig Bladder SMC; Primary-h HVIintersticial C; Primary-pig Esoph SMC; Primary-h NP Neuronal; Primary-rabbit Aorta SMC; Primary-h NSC; Primary-rabbit CorneaFB; Primary-h ral Cancerous; Primary-rabbit Lig FB; Primary-h SC; Primary-rat BMOB-like; Primary-h Skeletal Muscle Myoblast; COS-7; C-28/12; HK-2; Primary-h Uterus Cancerous; Primary-rat Ventricle CM; Primary-h Vase EC; Primary-sheep Carotid Artery SMC; HCT-116; ROS 17/2.8; Primary-h Vocal FB; UMR-106; Primary-mouse Aorta SMC; H9; R1; Primary-rat Fetal Neuronal; Primary-chicken Ear EpiC; Huh7; Primary-rat Vasc SMC; Primary-h NP SC; ES-D3; IMR-90; Primary-rat Bladder SMC; 293T; Primary-h Foreskin VascularEC; Primary-h Placenta EC; Primary-h Lung EpiC; Primary-h Prostate EpiC; U-87 MG; Primary-dog Carotid Artery SMC; Primary-rabbit Cornea StC; Primary-dog ID Annulus Fibrosus; Primary-chicken Embryo Chondrocyte; Primary-EC; HFF; Vero; HFL-1; Primary-h Adipose FB; Primary-cow FB; Primary-h UTSMC; Primary-rat Ventricle FB; AH 927; Primary-sheep Vasc FB; DU-145; ST2; B16.F10; Primary-h Nasal EpiC; Primary-ID Annulus C; Primary-h Dental Pulp SC; 3H10T1/2; Primary-Heart Valve; Primary-h Bone Alveolar; Primary-rabbit Tendon FB; Primary-mouse Kidney Insulin; HEPM; Primary-baboon Aorta SMC; HTK; Primary-mouse MDSC; Primary-rat Esoph EpiC; Primary-mouse Nerve SC; Primary-h Fetus OB-like; Primary-mouse Skeletal Muscle SC; hFOB 1.19; Primary-Nerve Schwann; Primary-h Ganglia Neuronal;

Caco-2; Primary-h Kidney Renal; Primary-h Breast EpiC; Primary-h Liver SC; Primary-pig Bladder Uro; Primary-h Lung EC; Primary-h Breast FB; Primary-sheep Jugular Vein EC; Primary-pig Esoph EpiC; Primary-h Lymph EC; Primary-chicken CC; Primary-h Lymph TCell; Primary-h Colon Adenocarcinoma; Primary-h Mammary EC; Primary-pig Vocal FB; Primary-h Mammary EpiC; Primary-rabbit Adipose SC; Primary-h Cornea EC; H9c2; Primary-h UT StC; Primary-cat Heart CM; Primary-mouse Pancreas EpiC; HS-5; Primary-sheep Skeletal Muscle Fetus Myoblast; Primary-cow ID; Primary-mouse BM OCpre; Primary-cow Knee Meniscus C; Hep-3B; Primary-cow Lig FB; HL-1; HuS-E/2; RWPE1; Primary-cow Retina EpiC; Primary-hVascMyoFB; IEC-6; Primary-mouse Fetal Hep; HS68; OVCAR-3; Primary-dog Knee MeniscusC; Primary-rabbit Mesoderm Mes PreC; Primary-dog Lig FB; Primary-rat Lung Alveolar; Primary-dog Skin Keratinocyte; CRL-11372; Primary-dog Vase SMC; HMEC-1; Primary-Embryo SC; T-47D1; Pimary-goatCC; Primary-h UVSC-like; Primary-guineapig Ear EpiC; Primary-Ligament; Primary-guineapig Skin FB; Primary-mouse Cortical Neuronal; Primary-hAdipose Adipocyte; Primary-mouse Liver SC; Primary-h Adipose FB-like; CAL72; J774; P19; Primary-h Amniotic fluid; Primary-rabbit Cornea EC; Primary-h Amniotic FSC; Primary-rat BMFB-like; ARPE-19; Primary-rat Kidney Mesangial; K-562; Primary-rat Nasal Ensheathing; Primary-h Bladder StC; Primary-chicken Embryo Proepicardium; ATDC5; Primary-sheep FB; Kasumi-1; Primary-Skeletal Muscle; Primary-h Bone Mes PreC; HMT-3522; Primary-h Bone Periosteal; A431; Primary-h Brain EC; Primary-h UTFB; KLE; 143b OST; BALB/3T3; Primary-h Vasc FB; LLC-PKI; Primary-h Vasc Pericyte; BHK21-C13; Primary-Mammary EpiC; M.DUNNI; C4-2B; ZR-75; HEC-1B; Primary-h Gingiva Keratinocyte; U178; Primary-h HN Cancerous; Primary-mouse Mammary EpiC; Primary-h Keratinocyte; Primary-mouse Sciatic N Schwann; OVCA429; Primary-h Kidney EpiC; Primary-pig Esoph FB; MBA-15; Primary-pig Mandible FB-like; Primary-h Liver Cancerous; Primary-rabbit Bladder Uro; GD25beta1A; Primary-rabbit ID AnnulusC; HSC-T6; Primary-rabbit NP Neuronal; DOV13; HEY; Primary-h Mammary FB; HTB-94; BZR-T33; Primary-chicken CorneaFB; MiaPaCa2; Primary-rat Mucosa Ensheathing; Primary-hOvaryFB; Primary-rat Salivary Acinar; Primary-h Ovary Oocyte; Primary-rat Testes Germ; Primary-h Pancreas Cancerous; Primary-chicken Embryo StC; Primary-h Pancreas Stellate Cells; Primary-sheep Carotid Artery FB; MLO-Y4; Primary-chicken Retina SC-like; Primary-h Prostate Cancerous; Primary-chicken Ten TC; Primary-h Saph V Myo FB; Primary-Synoviocyte; MTLn3; Primary-Vase EC; Primary-h Skeletal Muscle Pre; RT4-D6P2T; C2; SCA-9; HOC-7; T31; Primary-h UC EpiC; TR146; HCS-2/8; EA.hy926; Primary-rat Ebryo; SW480; Primary-sheep Fetus CC; Primary-dog Pancreas Insulin; KS-IMM; BPH-1; Primary-rat Pancreas SC; M2139; RIN-5F; Primary-hGallbladderCancerous; E14/TG2a; M4E; HES3; G8; Primary-hConjunctivaFB; Primary-dogSaphVEC; LN CaP; Primary-dog Saph V SMC; M4T; Primary-h Fetus CC; BR-5; Primary-pig UT Uro; Primary-Hippocampus Neuronal; PE-0041; Primary-dog Skin FB; Primary-rabbit Skeletal Muscle Myo-Blast; Primary-cow Denta ipulp; CGR8; Primary-dog Teeth PDL; Primary-rat Fetus Hep; Primary-dog Tendon FB; Primary-rat Mammary; Primary-h Knee C; Primary-rat SMC; BRC6; Primary-sheep Artery FB; Primary-dog Vasc EC; Primary-cow Mammary Alveolar; pZIP; 293 cell line; BMC9; Primary-h Lung Cancerous; SKOV-3; IOSE; TEC3; MCF-12A; Primary-rabbitBladderEpiC; Gli36DeltaEGFR; Primary-rabbit Conjunctiva EpiC; Primary-h Lung Neuronal; Primary-rabbit Endometrium EpiC; 1205Lu; Primary-rabbit MDSC; 3T3-A31; Primary-rabbit Tendon Tenocyte; MDA-MB-435; Primary-h Cancerous; Primary-cow EC; Primary-rat Cornea FB; Primary-EpiC; Primary-rat Fetal Cardiac; Primary-h Meninges Arachnoidal; COS-1; Primary-Eye; Primary-rat Liver Oval C; GLUTag-INS; Primary-rat Oral Mucosa Keratinocyte; GM3348; CRFK; 21NT; Primary-rat Testes EC; Primary-h Nasal FB; Primary-h Dura MaterSC; Primary-h Nasal OB; Primary-dog NP Neuronal; Primary-h Nasal Secretory; Primary-sheep Lung FB; AC-1M59; BHPrE1; MIN6; Primary-UT; MKN28; RAT-2; MLO-A5; RT112; CRL-2266; S91; GM5387; SK-ChA-1; Primary-horse CC; SPL201; Primary-horse Tendon FB; Primary-h Fetus Mes PreC; D283; Primary-pig Thyroid EpiC; H1299; Par-C10; AE-6; Primary-rabbit Blood Platelet; Primary-goat Carotid EC; Primary-rabbit Bone OC; Primary-goat Carotid FB; Primary-cow Comea FB-like; Primary-h Pancreas SC; Primary-rabbit CT Pericyte; Primary-goat Carotid SMC; Primary-rabbit Esophagus SMC; Primary-h Parotid Acinar; Primary-baboon Blood EC; A498; Primary-h Bronchi SMC; Primary-h Placenta SC; Primary-rabbit Sphincter SMC; Primary-cow Retina SC; 7F2; MM-Sv/HP; A10; Primary-h Prostate StC; Primary-buffalo Embryo SC-like; Primary-h Salivary Cancerous; CHO-4; Primary-h Salivary Salisphere; Primary-rat Cortical Neuronal; H13; Primary-rat Embryo Neuronal; Primary-guineapig Pancreas EpiC; Primary-rat Fetal OB; H144; CNE-2; MPC-11; 21PT; Primary-cow Synovium; Primary-rat Liver EC; Primary-cow Fetus CC; BEAS-2B; H2122; LM2-4; Detroit 551; C18-4; FLC4; Ishikawa; Primary-rat Skin Keratinocyte; H35; Primary-rat Tendon; Primary-h SMC; HTR8; Primary-h Synovial CC; E8.5; H460M; HL-60; MUM-2B; CRL-1213; MUM-2C; CRL-12424; W20-17; Lovo; Primary-dog Blood EC; Primary-sheep Nasal CC; HAK-2; Primary-sheep Skin FB; Primary-h Testes Sertoli; Primary-h Thyroid Cancerous; Primary-Trachea; Primary-h Trachea; LRM55; Primary-h UASC-like; Primary-Colon FB; Primary-hUASMC; r-CHO; HAT-7; RN22; HC-11; Primary-h Eye Vitreous; AEC2; S2-020; HCC1937; CRL-2020; AG1522; SCC-71; N18-RE-105; SK-N-AS; Primary-h Uterus SMC; SLMT-1; IMR-32; STO; NB4; Swan 71; Primary-h Alveolar Perosteum; Primary-dog Oral Mucosa EpiC; Primary-h Amnion EP; Primary-h Fetus Schwann; Primary-dog Bone OB; Primary-pig UTSMC; 184A1; Panc 1; NCTC 2544; 46C; Primary-cow Cornea EC; B6-RPE07; Primary-hamster EC; cBAL111; Primary-hamster Retina Neuronal; HEPA-1Clc7; NEB1; CCE; NHPrE1; Primary-rabbit Conjunctiva FB; 410; Hepa RG; Primary-Keratinocyte; PMC42-LA; Primary-dog Cartilage Synov; 21MT; NOR-PT; Primary-rabbit Endometrium StC; Primary-Lymphnode Lymphocyte; DLD-1; Primary-Lymphnode TCell; Primary-rabbit Lacrimal Gland Acinar; AB2.1; primary-rabbit Lung Pneumocyte; Primary-monkey Embryo; ES-2; Primary-monkey Kidney FB-like; Primary-rabbit Penis SMC; Primary-mouse Adipose StC; Primary-rabbit Skin FB; NR6; Primary-Blood SC; Primary-mouse BM Macrophage; 786-0; AT2; Primary-rat Adrenal Chromaffin; AT3; CCF-STTGI; Primary-mouse Bone Calvarial; Primary-rat Bladder Uro; HCT-8/E11; CE3; Primary-mouse Brain Neuronal; CFK2; Primary-mouse Breast Cancerous; L6; Primary-mouse Chondrocytes; HeyA8; Primary-mouse Colon EpiC; Primary-rat Cortical Astrocyte; Primary-dog CFB; Primary-buffalo Ovary EpiC; Primary-dog Cornea Chondrocyte; Primary-rat Embryo CM; Primary-mouse Embryo Neuronal; A2780; C5.18; Primary-dog MV EpiC; Primary-mouse Esophagus SC; Primary-rat Fetal Renal;

HEK001; A357; EFO-27; Primary-chicken Bone OB; Primary-mouse Fetal Lung; Primary-rat Heart SC-like; Primary-mouse Germ; Primary-rat Kidney; EN Stem-A™; Primary-rat Lacrimal Acinar; U-251 MG; Primary-dog Myofibroblasts; A4-4; Primary-rat Liver SC-like; Primary-cow Brain EC; Primary-rat Lung FB; Primary-mouse Kidney Renal; BEL-7402; NT2; HIAE-101; Primary-h BM Mononuclear; Primary-rat Ovary; Primary-mouse Lymph FB-like; Primary-rat Pancreas Islets; Primary-dog Esophageal EpiC; Primary-rat Renal EpiC; Primary-mouse Mast; Primary-chicken Embryo Blastoderm; NTera2/c1.D1; G-415; Null; Primary-rat Small Intestine; Primary-mouse Ovary Cumulus C; Primary-rat Teeth SC-like; HEL-299; Primary-rat Tendon Tenocyte; KB; b-End-2; Primary-mouse Pancreas Insulin; Primary-rat Vase EC; Primary-mouse Salivary Salisphere; Primary-h Duodenum EpiC; Primary-h Bone Fetus OB; Primary-Respiratory EpiC; Primary-mouse Skeletal Muscle Myoblast; Primary-sheep Amniotic fluid; OC2; Primary-chicken Heart CM; Daudi; Primary-shee pArtery MyoFB; Primary-mouse SkinKeratinocyte; Primary-sheep Bone OB-like; Primary-mouse Small Intestine; Primary-chicken Heart ECM; Primary-mouse Spleen Tcell; LNZ308; Primary-mouse Teeth Odontoblast; Primary-sheep ID Annulus Fibrosus; Primary-mouse Testes SC; Primary-sheep Jugular Vein SMC; Primary-mouse Testes Sperm; Primary-sheep Lung SC; Primary-mouse UT Uro; Primary-sheep Saph VEC; Primary-mouse Uterus EpiC; Primary-sheep Skin EC; OCT-1; Primary-sheep Vasc EC; HELF; Primary-sheep Vasc SMC; CAC2; HL-7720; OPC1; Primary-Teeth PDL; Primary-dog Heart SC; Primary-UCB Mononuclear; Primary-pig Artery Carotid EC; Primary-h Endometriotic CystStC; Primary-pig Artery Carotid SMC; Primary-Colon Cancerous; Primary-pig Artery Coronary SMC; QCE-6; Primary-pig Bladder FB; R221A; OSCORT; LS180; B35; RIF-1; Calu-1; RL-65; Calu-3; Primary-cow Adrenal ChrC; B5/EGFP; RT-112; Primary-pigEC; RW.4; Primary-pig ESC; S2-013; OVCAR-5; S5Y5; Primary-h Bone OC-like; SA87; INT-407; SAV-I; Primary-pig Fetus Hep; SCC-68; P69; HNPSV-1; CaSki; SK-CO15; Primary-pig Iliac EC; SK-N-DZ; Hep2; SKOV3Ip.1; Primary-pig Mandible Ameloblast; SNB 19; Primary-cow Joint Synovial; Primary-h Fetus FB; Primary-pig Mandible Odontoblast; SW1353; Primary-pig NP Neuronal; SW948; Primary-pig Oral MucosaEpiC; CRL-2102; Primary-pig PancreasIslets; T4-2; Primary-pig PulmonarySMC; TE-85; Primary-pig Salivary Acinar; THP-1; Primary-pig SynoviumSC; BME-UV1; KG-1; D4T; HUES-9; Primary-mouse Hippocampus Neuronal; ECV304; NRK; Primary-mouse Kidney Mesangial; D407; I0T1/2 cell line; and Primary-h Foreskin Melanocyte.

5.3. Biomarkers

In certain non-limiting embodiments, the first targeting molecule and the second targeting molecule target at least one biomarker of a biological subject of interest. In certain non-limiting embodiments, the first and second targeting molecules can target the same or different biomarker(s) of a biological subject of interest. In certain non-limiting embodiments, when the first and second targeting molecule are targeting two different biomarkers, the biomarkers are expressed on the same cell.

In certain non-limiting embodiments, there is only one targeting molecule targeting one biomarker.

In certain non-limiting embodiments, the biomarker can be expressed on the surface of the cell or internally. In certain non-limiting embodiments, the biomarker can be a cell surface protein, receptor, receptor subunit, tissue-specific antigen, virally derived protein, virally encoded envelope protein, bacterially derived protein, bacterial surface protein, etc. In certain non-limiting embodiments, the biomarker is an integrin.

In certain non-limiting embodiments, the biological subject is a protein, virus, cell, tissue, organ or organism. In certain non-limiting embodiments, the cell can be, but is not limited to, a tumor, cancer, or diseased cell. In certain non-limiting embodiments, the first and second targeting molecules bind to a cell (including a tumor or cancer) such as, but not limited to, pancreatic cancer, breast cancer, colorectal cancer, NSCLC, lung cancer, bone cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, vaginal carcinoma, vulval carcinoma, Hodgkin's Disease, esophagus cancer, small intestine cancer, endocrine system cancer, thyroid gland cancer, parathyroid gland cancer, adrenal gland cancer, soft tissue sarcoma, urethral cancer, penis cancer, prostate cancer, bladder cancer, kidney cancer, ureter cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiform, astrocytoma, schwannoma, ependymoma, medulloblastoma, meningioma, squamous cell carcinoma and pituitary adenoma tumors, or tumor metastasis. In certain non-limiting embodiments, the level of biomarkers are lower than would be detectable by other methods. In certain non-limiting embodiments, the current method is able to detect early stages of the disease (e.g., cancer). In certain non-limiting embodiments, the current method is able to detect low levels of biomarker presence.

In certain non-limiting embodiments, the biomarker can be epidermal growth factor receptor (EGFR), integrin $\alpha_1\beta_1$, integrin $\alpha_2\beta_1$, integrin $\alpha_3\beta_1$, integrin $\alpha_4\beta_1$, integrin $\alpha_5\beta_1$, integrin $\alpha_6\beta_1$, integrin $\alpha_v\beta_3$, uPAR, gastrin-releasing peptide (GRP), SSTR2, SSTR3, SSTR4, SSTR5, Folate receptor, CCR5, CXCR4, plectin-1, VEGF, CA19-9, PD-l1, Her2/neu, 5-alpha reductase, α-fetoprotein, AM-1, APC, APRIL, BAGE, β-catenin, Bcl2, ber-ab1 (b3a2), CA 125, CASP-8/FLICE, Cathepsins, CD13, CD19, CD20, CD21, CD23, CD22, CD38, CD33, CD35, CD40, CD44, CD45, CD46, CD5, CD52, CD55, CD59 (791Tgp72), CDC27, CDK4, CEA, c-myc, COX-2, Cytokeratin, DCC, DcR3, E6/E7, EGFR, EMBP, Ena78, Estrogen Receptor (ER), FGF8b and FGF8a, FLK 1/KDR, G250, GAGE-Family, gastrin 17, Gastrin-releasing hormone (bombesin), GD2/GD3/GM2, GnRH, GnTV, gp100/Pme117, gp-100-in4, gp15, gp75/TRP-1, hCG, Heparanase, Her3, HMTV, Hsp70, hTERT (telomerase), IGFR1, IL 13R, iNOS, Ki 67, KIAA0205, K-ras, H-ras, N-ras, KSA (CO17-1A), LDLR-FUT, MAGE Family (MAGE1, MAGE3, etc.), Mammaglobin, MAP17, Melan-A/MART-1, mesothelin, MIC A/B, MT-MMP's, such as MMP2, MMP3, MMP7, MMP9, Mox1, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, Progesterone Receptor (PR), PSA, PSM, RAGE-1, Rb, RCAS1, SART-1, SSX gene family, STAT3, STn (mucin assoc.), TAG-72, TGF-α, TGF-β, Thymosin β-15, IFN-γ, TPA, TPI, TRP-2, Tyrosinase, VEGF, ZAG, p161NK4, Myo D1, Glutathione, or S-transferase. In certain non-limiting embodiments, the biomarker can be epidermal growth factor receptor (EGFR), integrin $\alpha_v\beta_3$, uPAR, gastrin-releasing peptide (GRP), SSTR2, CCR5, integrin U401, VEGF, CA19-9, CD13, CD40, or PD-L1. In certain non-limiting embodiments, the biomarker is uPAR and/or integrin $\alpha_v\beta_3$. In certain non-limiting embodiments, the biomarker is CD13 and/or integrin $\alpha_v\beta_3$.

Integrins are cell adhesion molecules that mediate cell-cell and cell-matrix interactions and contribute to migration, proliferation, angiogenesis, tumor invasion, and metastasis. Integrin $\alpha_v\beta_3$ serves as a receptor for extracellular matrix proteins with exposed arginine-glycine-aspartic (RGD) tripeptide sequence. Importantly, integrin $\alpha_v\beta_3$ usually expresses at very low (or undetectable) levels in most adult epithelia cells, but are highly upregulated in various tumor cells. Recent expression analysis demonstrated that the patients with high $\alpha_v\beta_3$ expression showed significantly shorter survival times than those with low $\alpha_v\beta_3$-expression. Its restricted expression during tumor growth, invasion, and metastasis presents an interesting molecular target for diagnosis and treatment of the rapidly growing and metastatic tumors and, therefore, $\alpha_v\beta_3$ is an example of one of the biomarkers of the invention.

Aminopeptidase N (APN)/CD13, a transmembrane protease, is another important biomarker. Similar to integrin $\alpha_v\beta_3$, CD13 is also up-regulated in the angiogenic vessels in the tumor but only barely expressed in the normal blood vessels, and high expression of CD13 has been observed in a number of human solid tumors, including melanoma, prostate, lung and ovarian cancer and pancreatic cancer. NGR sequence containing peptides have shown high efficiency/selectivity in binding with CD13. Thus, CD13 provides another example biomarker in accordance with the invention.

uPAR is another important biomarker for cancer imaging, as both clinical studies and laboratory research revealed that overexpression of uPA/uPAR is strongly correlated with poor prognosis in malignant tumors. Moreover, uPAR is overexpressed in various malignancies (normally expresses several thousand receptors per cell), but absent or very poorly expressed in normal and adjacent tissues. Thus, uPAR is an example of another biomarker of the invention.

In certain non-limiting embodiments, multivalent compounds of the present invention directed to integrin $\alpha_v\beta_3$ and CD13 (e.g., CNGRC-($^{68}$Ga)NOTA-RGDyK heterodimer ("CNGRC" disclosed as SEQ ID NO: 1)) can be used to detect early stages of the cancer. In certain non-limiting embodiments, multivalent compounds of the present invention directed to integrin $\alpha_v\beta_3$ and CD13 can be used to detect low levels of integrin $\alpha_v\beta_3$ and/or CD13.

5.4. Kits

The present invention further provides kits that can be used to practice the invention. For example, and not by way of limitation, a kit of the present invention can comprise at least one imaging and/or drug delivery compound. In certain non-limiting embodiments, a kit of the present invention can optionally comprise instructions on how to use the kit for molecular imaging and/or targeted drug delivery. In certain non-limiting embodiments, a kit can further comprise an administration device such as a syringe and/or catheter and/or introducer sheath.

In certain non-limiting embodiments, the imaging and/or drug delivery compound comprises a monomer with a detectable label and/or active agent. In certain non-limiting embodiments, the imaging and/or drug delivery compound comprises a homodimer with a detectable label and/or active agent. In certain non-limiting embodiments, the imaging and/or drug delivery compound comprises a heterodimer with a detectable label and/or active agent. In certain non-limiting embodiments, the imaging and/or drug delivery compound comprises a targeting molecule with a dye molecule with a detectable label and/or active agent.

The present invention further provides kits for preparing the imaging and/or drug delivery compound. In certain non-limiting embodiments, the kit of the present invention contains the first targeting molecule (in dry or liquid form) and/or the second targeting molecule (in dry or liquid form) and/or the chelator for assembly into the imaging and/or drug delivery compound. When the molecule is provided in dry form, the kit can contain the appropriate buffer or solvent to create a solution or composition.

The present invention further provides kits for determining the optimal length of spacers of the imaging and/or drug delivery compound. In certain non-limiting embodiments, the kit of the present invention contains the first targeting molecule (in dry or liquid form) and/or the second targeting molecule (in dry or liquid form) and/or spacers of different length and/or a radio-metal labeled chelator for a high-throughput screening platform. In certain non-limiting embodiments, the kit can contain the appropriate buffer or solvent to create perform the high-throughput assay.

The following Examples are offered to more fully illustrate the disclosure, but is not to be construed as limiting the scope thereof. Methods and materials described in the examples are hereby incorporated by reference into the detailed description of the invention.

6. EXAMPLES

Example 1: Synthesis of a Metal Chelator of the Invention

The 1, 4, 7-triazacyclonenonane (TACN)-based chelator (N3-NOtB2) was prepared as shown in Scheme 1:

Scheme 1 Synthesis of N3—NOtB2

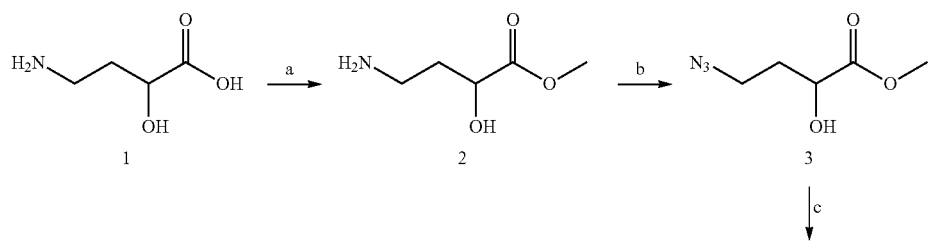

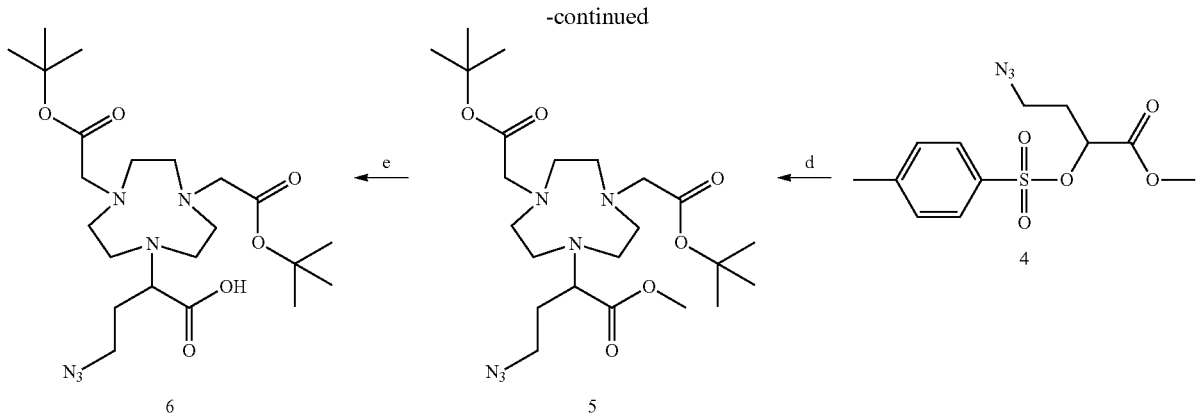

Reaction conditions: a) MeCOCl, MeOH; b) imidazole-1-sulfonyl azide hydrochloride, CuSO₄, K₂CO₃, MeOH c) TsCl, TEA, DCM; d) NO2A(tBu), Cs₂CO₃, MeCN; e) 30% nBu₃NOH, MeOH

4-amino-2-hydroxybutanoate (2)

MeCOCl (15 mL) was dropwise added to anhydrous methanol (100 mL) at 0° C. The resulting mixture was stirred at room temperature for 1 h. Then, starting material (1) (10 g, 84 mmol) was added and the mixture was stirred for 2 h at room temperature. Solvent was removed under reduced pressure, and the residue was treated with ether (50 mL) to obtain (2) (12.67 g, 88.5%) as a white solid after filtration. No further purification is needed suggested by TLC and NMR. ¹H NMR (400 MHz, D₂O) 64.53-4.44 (m, 1H, —CH(COOH)—), 3.82 (s, 3H, —CH₃), 3.27-3.11 (m, 2H, —CH₂N₃), 2.31-2.19 (m, 1H, —CH₂CH₂N₃), 2.13-1.98 (m, 1H, —CH₂CH₂N₃). ¹³C NMR (101 MHz, D₂O) δ 175.16, 68.50, 52.89, 36.66, 30.42. ESI-MS: observed, m z (M+H)⁺=133.92, calculated, (M+H)⁺=134.08.

methyl 4-azido-2-hydroxybutanoate (3)

Imidazole-1-sulfonyl azide hydrochloride (2.5 g, 12 mmol) was added to the slurry of (2) (1.7 g, 5 mmol), K₂CO₃ (3.2 g, 23 mmol), and CuSO₄·5H₂O (30 mg, 100 μmol) in MeOH (30 mL) and the mixture was stirred overnight. The mixture was concentrated, diluted with H₂O (100 mL), acidified with conc. HCl and extracted with EtOAc (50×3 mL). The combined organic layers were dried (MgSO₄), filtered and concentrated to obtain crude (3) (1.22 g, 76.6%) as a colorless liquid. The crude was used in the next step without further purification. For NMR spectra, a little crude was purified by silica gel chromatography (DCM/MeOH, 10:1) to give pure (3) as a colorless liquid. ¹H NMR (400 MHz, CDCl₃) δ 4.31 (dd, J=7.6, 4.0 Hz, 1H, —CH(COOH)—), 3.83 (s, 3H, —CH₃), 3.59-3.43 (m, 2H, —CH₂N₃), 2.93 (brs, 1H, —OH), 2.15-2.04 (m, 1H, —CH₂CH₂N₃), 1.99-1.86 (m, 1H, —CH₂CH₂N₃). ¹³C NMR (101 MHz, CDCl₃) δ 175.06, 67.60, 52.81, 47.18, 33.16.

methyl 4-azido-2-(tosyloxy)butanoate (4)

TsCl (2.7 g, 14 mmol) was added to a solution of (3) (1.5 g, 9.4 mmol) and TEA (3 g, 30 mmol) in DCM (50 mL) and the mixture was stirred at room temperature overnight. The mixture was then washed by water (30×2 mL), dried over MgSO₄, and filtered. Concentration of the filtrate and flash chromatography (EtOAc/Hexane, 1:4) gave (4) (2.37 g, 70.8%) as a white solid. ¹H NMR (400 MHz, CDCl₃) δ 7.84 (d, J=8.3 Hz, 2H, Ar—H), 7.38 (d, J=8.1 Hz, 2H, Ar—H), 4.97 (dd, J=7.6, 5.0 Hz, 1H, —CH(COOH)—), 3.72-3.68 (m, 3H, —CH₃), 3.47-3.39 (m, 1H, —CH₂CH₂N₃), 3.37-3.27 (m, —CH₂CH₂N₃), 2.47 (s, 3H, Ar—CH₃), 2.13-1.98 (m, 2H, —CH₂N₃). ¹³C NMR (101 MHz, CDCl₃) δ 168.68, 145.46, 132.89, 129.88, 128.08, 74.36, 52.77, 46.36, 31.53, 21.69.

di-tert-butyl 2,2'-(7-(4-azido-1-methoxy-1-oxobutan-2-yl)-1,4,7-triazonane-1,4-diyl)diacetate (5)

To a slurry of NO2A(tBu) (0.8 g, 2.24 mmol) and Cs₂CO₃ (1.1 g, 3.36 mmol) in MeCN (20 mL), (4) (0.95 g, 2.67 mmol) was added and the mixture was heated at 50° C. for 1 d. After cooling to room temperature, the mixture was filtered and concentrated. The residue was purified by silica gel chromatography (DCM/MeOH, 10:1) to give (5) (0.73 g, 65.2%) as a yellowish liquid. ¹H NMR (400 MHz, CDCl₃) δ 3.73-3.60 (m, 3H, —OCH₃), 3.58-3.44 (m, 2H, —CH₂N₃), 3.39 (s, 1H—NCH—), 3.28 (s, 4H, 2*—CH₂CO—), 3.02-2.58 (m, 12H, 6*—NCH₂—), 2.01-1.79 (m, 2H, —CH₂CH₂N₃), 1.43 (s, 18H, 6*—CH₃). ¹³C NMR (101 MHz, CDCl₃) δ 173.51, 171.54, 80.70, 63.83, 59.40, 56.11, 55.77, 53.31, 51.23, 48.52, 29.52, 28.21. ESI-MS: observed, m z (M+H)⁺=499.266, calculated, (M+H)⁺=499.32. ESI-HRMS: observed, m z (M+H)⁺=499.3239, calculated, (M+H)⁺=499.3239.

4-azido-2-(4,7-bis(2-(tert-butoxy)-2-oxoethyl)-1,4,7-triazonan-1-yl)butanoic acid (N3-NO'B₂, 6)

To a solution of (5) (100 mg, 0.2 mmol) in pyridine (2 mL), LiI (134 mg, 1 mmol) was added and the mixture was stirred for 4 h at room temperature. The mixture was treated with DCM (20 mL), and washed with saturated citric acid (10×2 mL) and water (20 mL). The organic layer was dried over MgSO₄, filtered and concentrated to give crude (6). Pure (6) (50 mg, 51.5%) as a white solid was obtained after purification with silica gel chromatography (DCM/MeOH, 20:3). ¹H NMR (400 MHz, CDCl₃) δ 3.72 (d, J=7.1 Hz, 1H, —NCH(COOH)—), 3.70-3.41 (m, 6H, 2*—CH₂CO— &—CH₂N₃), 3.43-2.75 (m, 12H, 6*—NCH₂—), 2.36-2.21 (m, 1H, —CH₂CH₂N₃), 1.91 (dd, J=12.9, 5.2 Hz, 1H, —CH₂CH₂N₃), 1.46 (s, 18H, 6*—CH₃). ¹³C NMR (101 MHz, CDCl₃) δ 172.17 (—COOH), 169.51 (2*—CO₂C(CH₃)₃), 82.28 (—CO₂C(CH₃)₃), 63.12 (—NCH(COOH)—), 56.35 (2*—NCH₂CO₂C(CH₃)₃), 50.79

(—N—CH$_2$—), 49.80 (—N—CH$_2$—), 49.16 (—N—CH$_2$—), 49.04 (—CH$_2$N$_3$), 28.62 (—CH$_2$CH$_2$N$_3$), 28.12 (6*—CH3). ESI-MS: observed, m z (M+H)$^+$=485.45, calculated, (M+H)$^+$=485.31. ESI-HRMS: observed, m z (M+H)$^+$=485.3064, calculated, (M+H)$^+$=485.3082.

N$_3$—NOtB2 was synthesized with an overall yield of 15%.

Example 2: Synthesis of a Metal Chelator of the Invention

The TACN-based chelator (N$_3$-DOtB3) was prepared as shown in Scheme 2:

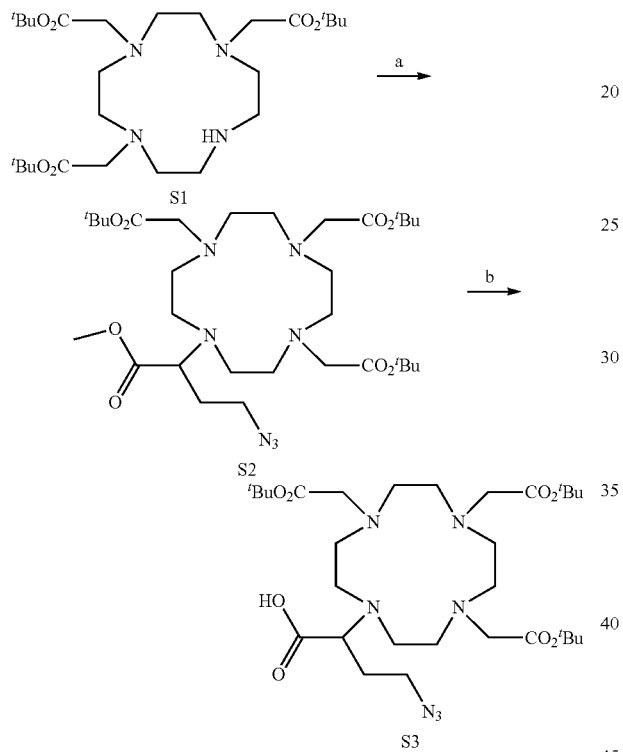

Reagents: a) 4, CsCO$_3$, MeCN; b) LiI, Pyridine tri-tert-butyl 2,2',2''-(10-(4-azido-1-methoxy-1-oxobutan-2-yl)-1,4,7,10-tetraazacyclododecan-1,4,7-triyl) triacetate (S2)

To a slurry of (S1) (DO3A(tBu)) (51.4 mg, 0.1 mmol) and Cs$_2$CO$_3$ (49 mg, 0.15 mmol) in MeCN (1 mL), (4) (38 mg, 0.12 mmol) was added and the mixture was shaken at 50° C. for 1 d. After cooling to room temperature, the mixture was filtered and concentrated. The reaction was monitored by LC-MS. Pure (S2) (30 mg, 38.4%) was obtained after purification with silica gel chromatography (DCM/MeOH, 10:1) $^1$H NMR (500 MHz, CDCl$_3$) δ 3.70-3.18 (m, 10H, —CHCO— & —NCH$_2$CO— & —OCH$_3$), 3.04-2.07 (m, 16H—NCH$_2$—), 1.97-1.81 (m, 2H, —CH$_2$N), 1.71-1.63 (m, 2H, —CH$_2$CH$_2$N$_3$), 1.48-1.45 (m, 27H, 9*—CH$_3$). ESI-MS: observed, m z (M+H)$^+$=656.455, calculated, (M+H)$^+$=656.435. ESI-HRMS: observed, m z (M+H)$^+$=656.4322, calculated, (M+H)$^+$=656.4347.

4-azido-2-(4,7,10-tris(2-(tert-butoxy)-2-oxoethyl)-1,4,7,10-tetraazacyclododecan-1-yl)butanoic acid (S3)

To a solution of S2 (10 mg, 0.015 mmol) in pyridine (0.5 mL), LiI (10 mg, 0.075 mmol) was added and the mixture was shaken for 2 h at room temperature. The mixture was treated with DCM, and washed with saturated citric acid and water. The organic layer was dried over MgSO$_4$, filtered and concentrated to give crude (S3). Silica gel chromatography (DCM/MeOH, 10:1) was applied to obtain pure S3 (3 mg, 31.2%). $^1$H NMR (500 MHz, CDCl$_3$) δ 3.87-3.74 (m, 2H, —CH$_2$CO—), 3.63-3.53 (m, 1H, —NCH(COOH)—), 3.46-3.33 (m, 4H, —CH$_2$CO—), 3.08-1.98 (m, 18H, —NCH$_2$— & —CH$_2$N), 1.67-1.56 (m, 2H, —CH$_2$CH$_2$N$_3$), 1.51-1.46 (m, 27H, 9*—CH$_3$). ESI-MS: observed, m z (M+H)$^+$=642.439, calculated, (M+H)$^+$=642.419. ESI-HRMS: observed, m z (M−H)$^-$=640.4046, calculated, (M−H)$^-$=640.4034.

N$_3$-DOtB3 was synthesized with an overall yield of 12%.

Example 3: Synthesis of an AE105-Dimers of the Invention

The TACN-based chelator was prepared as provided in Example 1. The TACN-based chelator was then attached to the AE105 peptide via solid-phase synthesis (SPS). In particular, N$_3$—NOtB$_2$ was attached to the N-terminal of peptide AE105 with a high yield via SPS.

Peptides were prepared on resin (Resin-AE105*, Resin-AE105-PEG$_8$-NH$_2$) using standard SPS protocol by a peptide synthesizer. Compound 6 (from Example 1) (3 eq.) was coupled to the resin by mixing them with HATU (5 eq.) and DIEA (10 eq.) in DMF for 2 h at room temperature. Moiety-A-NOTA-N$_3$ (7) was then obtained after cleavage from resin support using TFA/H$_2$O/TIS/phenol (90:5:2.5:2.5) and HPLC purification.

To obtain hetero-dimeric, homo-dimeric, and dual-modality compounds, the monomer (AE105-NOTA-N3) was cleaved from the Rink amide resin, and was then conjugated to a BCN-functionalized RGDyk (or AE105 or cynaine dyes Cy3 or Cy5) via a strain-promoted alkyne-azide cycloaddition (SPAAC) in high yield as outlined in Scheme 3:

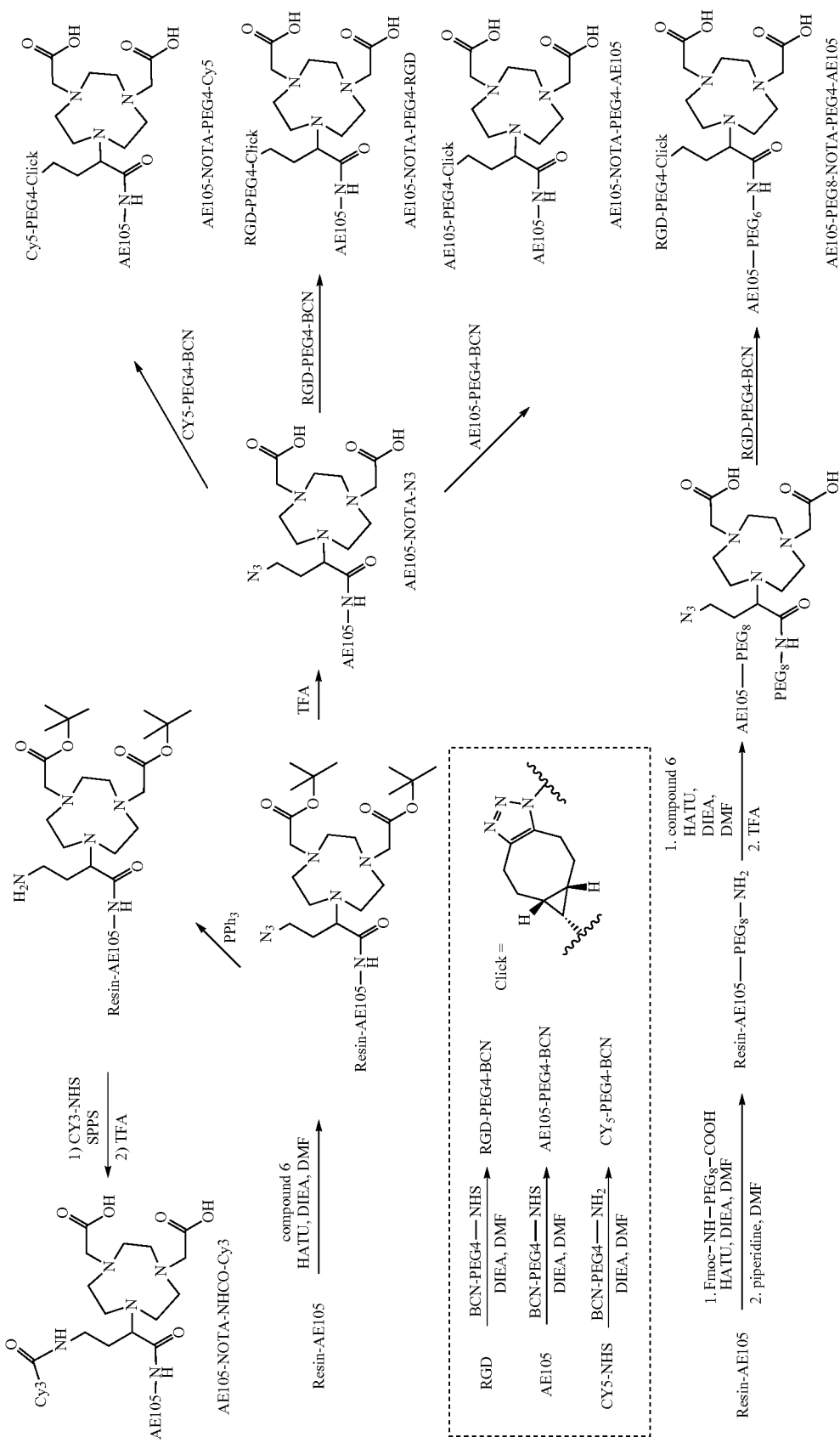

Rendered by the metal-free click reaction, >95% yield was achieved after incubating the monomer (AE105-NOTA-$N_3$) with 1.0 equivalent of BCN-attached peptides or dye overnight at 37° C. The resulting compounds could be used directly. HPLC purification through gradient elution staring from 0% acetonitrile 100% water to 100% acetonitrile could further increase the puritiy of those synthesized probes.

The above prepared probes were successfully labeled with $^{64}$Cu, $^{68}$Ga, and $Al^{18}F$ at 37° C., 70° C., and 90° C., respectively. Generally, nearly 100% labeling yield could be achieved for $^{64}$Cu and $^{68}$Ga labeling when a 1 nmol probe and 1 mCi radioactivity were used. FIG. 5 provides representative examples of the radio-HPLC results of the radio-labeling.

All above compounds could be labeled with $^{64}$Cu under mild conditions, with a specific activity of 1.0 mCi/nmol. The resulting radiotracers showed great stabilities in human serum after being incubated at 37° C. for 24 hours (with <2% $^{64}$Cu dissociation).

The resulting heterodimer (AE105-NOTA-RGD; FIG. 6) and monomers (AE105-NODAGA and RGD-NODAGA; FIG. 6) were radiolabeled with $^{64}$Cu at 70° C. in $NH_4OAc$ buffer (pH~6.8), and their serum stabilities were evaluated. The resulting radiotracers remained intact after being incubated at 37° C. for 24 hours, showing great serum stability. FIG. 7 provides radio-HPLC results demonstrating that there was no significant $^{64}$Cu-disassociation from the probe after incubating in serum for 1 day. The good serum stability demonstrates that the probe is able to stay intact during the circulation in the blood stream in vivo. The larger molecular weight and size will also increase retention of the probe in the blood.

Radiolabeling of compounds: For Cu-64 labeling, all compounds was conducted in a 0.1 M $NH_4OAC$ buffer (pH=6.8). Briefly, $^{64}CuCl_2$ (usually in 0.1 N HCl) was first buffered in a 0.1 M $NH_4OAC$ buffer (pH=6.8), and then the prepared NOTA-bioconjugates were added. The resulting mixture was vortexed for 10 sec and incubated in a thermomixer at 37° C. for 0.5 h, after which the $^{64}$Cu incorporation yield was determined by radio-HPLC.

FIG. 8 depicts a dimer made with N3-DOtB3-AE105-PEG4-DOTA-PEG4-RGD.

Cell stain study: Cells were seeded in an 8 well chamber slide (100,000 cells per well) 24 h prior to the experiment. Before the experiment, cells were washed twice with PBS twice and added culture media. Then block agent (10 μg AE105) was added to half of the wells as cold block to determine in vitro non-specific uptake and incubated for 1 h. Then, AE105-NOTA-NHCO-Cy3 (10 pmol per well) was added to each well and further incubated for 2 h. Media was then removed and the cells were washed twice with PBS. After fixing the cells using 1% Paraformaldehyde, the nucleus was stained by DAPI. The slide was sealed and observed under fluorescence microscopy (40×, oil).

As shown in FIG. 9, staining and blocking were observed on U87MG human glioblastoma cell line, which confirmed the strong affinity of peptide AE105 towards uPAR receptor and indicated that AE105-NOTA-NHCO-Cy3 could also be used as optical probe.

Example 4: Cell-Uptake and Binding Studies

Cell uptake and stain studies were measured in U87MG human cancer cells. In particular, a comparison was made between the AE105-RGD heterodimer (FIG. 4) and the monomers AE105-NODAGA and RGD-NODAGA (FIG. 6).

Cell-uptake assay: U87MG human cancer cells were purchased from American Type Culture Collection (Manassas, VA). All cell handling was aseptically performed in a laminar flow hood. The U87MG cells were cultured in Dulbecco's Modified Eagle Medium, supplemented with 10% FBS, penicillin (100 unit/mL), streptomycin (100 μg/mL) L-glutamine (300 μg/mL) and sodium pyruvate (100 mg/mL), glucose (4.5 g/L) and maintained at 37° C., 5% $CO_2$.

Cells were seeded in 12-well plates (200,000 cells per well) 24 h prior to the experiment. Before the experiment, cells were washed with 1 mL HBSS twice and 1 mL media (DMEM with 0.1% BSA and 1 mM $Mn^{2+}$) was added to each well. Cells were then incubated with the $^{64}$Cu-labeled conjugates (10 pmol $^{64}$Cu-GYK12, $^{64}$Cu-RGD or $^{64}$Cu-AE105 per well). At each time point (1, 2 and 4 h) radioactive media was aspirated. The cells were washed twice with HBSS (pH 7.2) and dissolved in 0.5% SDS. The radioactivity in each fraction was measured with a gamma counter. The protein content of each cell lysate sample was determined. The measured radioactivity associated with the cells was normalized to same amount of cell protein per well. The cell uptake was expressed as the percentage added dose after decay correction.

The heterodimer showed significant improvements on the cell-uptake as compared to the monomers AE105-NODAGA and RGD-NODAGA at all examined time points ($p<0.1$) (FIG. 10).

Cell saturation binding assay: Cells were seeded in 24-well plates (100,000 cells per well) 24 h prior to the experiment. Before the experiment, cells were washed with 1 mL HBSS twice and 0.5 mL binding media (HBSS with 0.1% BSA and 1 mM $Mn^{2+}$) was added to each well. Then block agents (10 μg AE105 and/or 10 μg RGD) were added to half of the wells as cold block to determine in vitro non-specific binding, followed by $^{64}$Cu-AE105-RGD, $^{64}$Cu-RGD and $^{64}$Cu-AE105 in increasing concentrations (1-100 nM). The samples were incubated for 2 h on ice (4° C.). After incubation, the radioactive media was removed. Cell pellets were rinsed with ice cold binding buffer (1 mL) twice and dissolved in 0.5% SDS solution. The radioactivity in each fraction was measured in a gamma counter. The protein content of each cell lysate sample was determined (BCA Protein Assay Kit, Pierce). The measured radioactivity associated with the cells was normalized to the amount of cell protein present (fmol/mg).

The results showed that $^{64}$Cu-GYK12 exhibited significantly enhanced $B_{max}$ (488±73 fmol/mg) and binding affinity (9.9±4.2 nM), compared to those of two $^{64}$Cu-monomers: $^{64}$Cu-AE105 ($B_{max}$ 269±43 fmol/mg, $K_d$ 65±49 nM), and $^{64}$Cu-RGD ($B_{max}$ 260±44 fmol/mg, $K_d$ 91±36 nM).

Statistical analysis: All the experiments were performed in triplicate. Comparisons between different groups of experiments were made using the two-way ANOVA test (GraphPad Prism 6). When more than two data sets were compared, a two-way ANOVA analysis with Bonferroni post-tests were applied. P values <0.05 were considered statistically significant.

Example 5: PET Imaging Using the AE105-RGD Heterodimer

In vivo PET/CT imaging was conducted in NCr nude mice bearing U87MG tumor xenografts.

Nude mice were injected with U87MG cells (5 million cells in 150 μL PBS) into the subcutaneous flank of the right shoulder. Either AE105-RGD heterodimer (FIG. 4), AE105-NODAGA, or RGD-NODAGA were injected into bloodstream via tail vein injection. Blocking studies were conducted for the heterodimer studies by co-injecting 100 times of AE105 and RGD. Small animal PET/CT was performed at 1 h and 4 h post injection of tracers. Organ uptakes were determined by analysis of ROI. For AE105-RGD dimer, ex vivo biodistribution was also performed. The organs of mice were taken and counted using Gama-counter.

All xenografted tumors were visible at both 1 h and 4 h p.i. (FIG. 11). Organ uptake was determined from PET imaging quantitation. The results showed that higher tumor uptake (p<0.01) was observed with mice injected with $^{64}$Cu-heterodimer (1 h 3.13±0.49% ID/g, 4 h 3.27±0.25% ID/g), compared to that of the mice injected with two monomeric PET probes: $^{64}$Cu-AE105 (1 h 1.45±0.15% ID/g, 4 h 1.55±0.31% ID/g) and $^{64}$Cu-RGD (1 h 1.50±0.42% ID/g, 4 h 1.73±0.51% ID/g). The tumor to muscle ratio of $^{64}$Cu-heterodimer was 7.6±1.9 at 4 h, which is significantly higher than that of $^{64}$Cu-AE105 (4.2±1.1). The tumor to liver ratio of $^{64}$Cu-heterodimer was 1.5±0.4 at 4 h, which is also significantly higher than that of $^{64}$Cu-AE105 (0.43±0.1). The high intestine uptake can be attributed to the fact that $\alpha_v\beta_3$ integrin and uPAR are also highly expressed in intestine in young mice. In a blocking study performed by co-injecting unlabeled cyclo(RGDyK) and AE105 (100 µg for each one) (FIG. 12), the tumor uptake of $^{64}$Cu-heterodimer was reduced to 1.01±0.18% ID/g (4 h, p<0.01), which further confirmed the specificity of the heterodimer for targeting $\alpha_v\beta_3$ integrin and uPAR in U87MG xenografts. Ex vivo biodistribution was also conducted for AE105-RGD to validate the PET imaging quantitation data. The results are shown in FIG. 13.

Statistical analysis: All the experiments were performed in triplicate. Comparisons between different groups of experiments were made using the two-way ANOVA test (GraphPad Prism 6). When more than two data sets were compared, a two-way ANOVA analysis with Bonferroni post-tests were applied. P values <0.05 were considered statistically significant.

Example 6: Synthesis of Heterodimers for Dual Targeting

This Example provides an alternative method of synthesizing heterodimers for dual targeting. This method can be modified to prepare heterodimers combining various peptides.

A first peptide (Peptide A) can be prepared on resin (Resin-Peptide A-PEG$_n$-NH$_2$) using standard SPS protocol by a peptide synthesizer. N$_3$—NO$^t$B$_2$ can be coupled to the resin and peptide. The resulting Peptide A-PEG$_n$-NOTA-N$_3$ can be cleaved from the resin support using TFA and HPLC purification. The heterodimer can be prepared by further combination with Peptide B (e.g., Peptide B-PEG$_4$-BCN), as shown in Scheme 4.

Scheme 4 Synthesis of a heterodimer of two peptides.

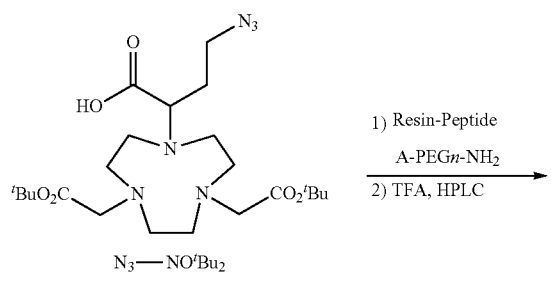

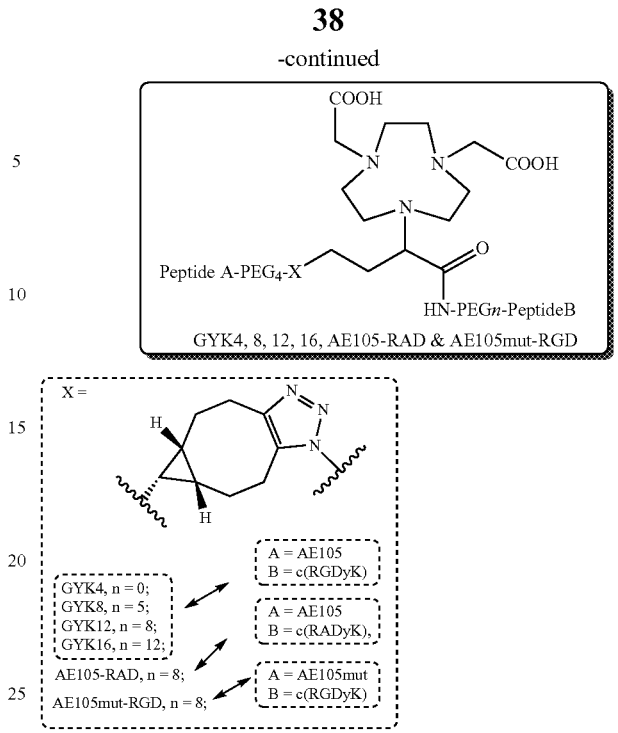

As shown in Scheme 4, the Peptides A and B can be selected from a number of suitable peptides. For example, they can be selected to target integrin and CD13. As such, Peptide A can be selected from AE105 and AE105mut and Peptide B can be selected from cyclo(RGDyK) and cyclo(RADyK). Additionally, the PEG spacer can be varied in length, e.g., from n=0 to n=12. For example, the heterodimers of AE105 and cyclo(RGDyK) are the same as described above in Example 4 (i.e., GYK4, GYK8, GYK12, and GYK16). However, this Example further demonstrates that heterodimers can be prepared with alternative targeting molecules, such as AE105mut and cyclo(RADyK).

The prepared heterodimers can be radiolabeled for in vitro and/or in vivo evaluation respectively. Cell uptake and/or efflux assays can be used to identify one or more heterodimers with the greatest potential for cell uptake and retention, as will be described in greater detail in Example 13, below. Additionally, a cell saturation binding assay can be performed as described in Example 4 to evaluation the Bmax and binding affinity of the heterodimers as compared to the monomers.

Example 7: Synthesis of an Integrin-CD13 Dual Targeting Compound

The integrin-CD13 dual targeting compound was prepared as shown in Scheme 4 (Scheme 4 discloses "CNGRC" as SEQ ID NO: 1):

Scheme 4 Synthesis of integrin-CD13 dual targeting compound

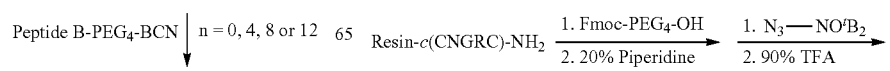

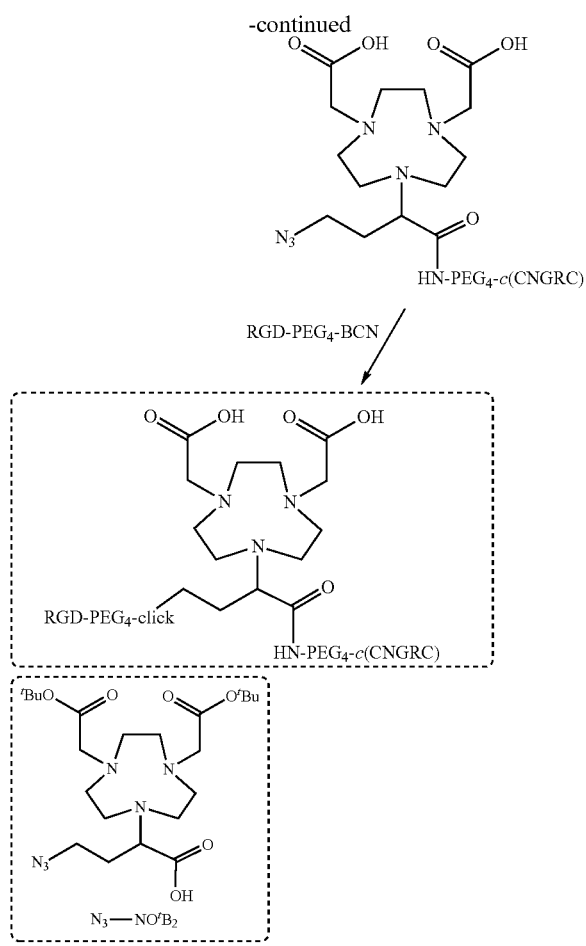

Using the bifunctional chelator (BFC) $N_3$—$NO'B_2$, the peptidic ligands c(CNGRC) ("CNGRC" disclosed as SEQ ID NO: 1) and c(RGDyK), targeting CD13 and $\alpha_v\beta3$ respectively, were linked covalently via a metalfree click reaction and an amide formation reaction. FIG. 1 depicts a dimer made with $N_3$—$NO'B_2$-c(CNGRC)-PEG4-NOTA-PEG4-RGD ("CNGRC" disclosed as SEQ ID NO: 1).

The Fmoc-$PEG_4$-OH and TACN-based chelators were attached to the cyclo(CNGRC) peptide ("CNGRC" disclosed as SEQ ID NO: 1) via solid-phase synthesis (SPS) sequentially. In particular, the $N_3$—$NOtB_2$ was attached to the N-terminus of the peptide cyclo(CNGRC)-PEG4-NH2 ("CNGRC" disclosed as SEQ ID NO: 1) with a high yield via SPS.

Peptide on resin (Resin-CNGRC) ("CNGRC" disclosed as SEQ ID NO: 1) was prepared using standard SPS protocol by a peptide synthesizer, and then the side chain of cysteine was deprotected and then cyclized by treating with thallium (III) trifluoroacetate. Fmoc-$PEG_4$-OH and $N_3$—$NO'B_2$ were attached to the resin sequentially, by mixing them with HATU (5 eq.) and DIEA (10 eq.) in DMF for 2 h at room temperature. The c(CNGRC)-PEG4-NOTA-$N_3$ ("CNGRC" disclosed as SEQ ID NO: 1) was then obtained after cleavage from the resin support using TFA/$H_2$O/TIS/phenol (90:5:2.5:2.5) and HPLC purification, and then ligated with cyclo(RGDyK)-$PEG_4$-BCN (prepared by mixing BCN-$PEG_4$-NHS with cyclo(RGDyK) in pH~8.5 PBS buffer) via strain-promoted alkyne-azide cycloaddition (SPAAC) between $N_3$ and BCN moieties.

Rendered by the triazole formation after metal-free click reaction, the purified heterodimers (NGR-NOTA-RGD) were successfully labeled with $^{64}$Cu, $^{68}$Ga and $Al^{18}$F at 37° C., 70° C., and 90° C., respectively. Labeling results were monitored by radio HPLC. Labeling yields were above 90% for $^{64}$Cu and $^{68}$Ga, close to 50% for $Al^{18}$F.

Example 8: Synthesis of an Integrin-CD13 Dual Targeting Compound

The integrin-CD13 dual targeting compound was prepared as shown in Scheme 5. The solid phase synthesis (Scheme 4) is more convenient from the aspect of synthesis as coupling agents used in the amide formation (the reaction between the amino group from the peptide and the carboxylic acid group from the BFC) can be easily removed. However, the solution phase synthesis (Scheme 5) consumed less amount of peptides and BFC; thus it can be suitable for small scale preparation when the amount of peptide and/or BFC available is limited.

Scheme 5 Synthesis of integrin-CD13 dual targeting compound
(Scheme 5 discloses "CNGRC" as SEQ ID NO: 1)

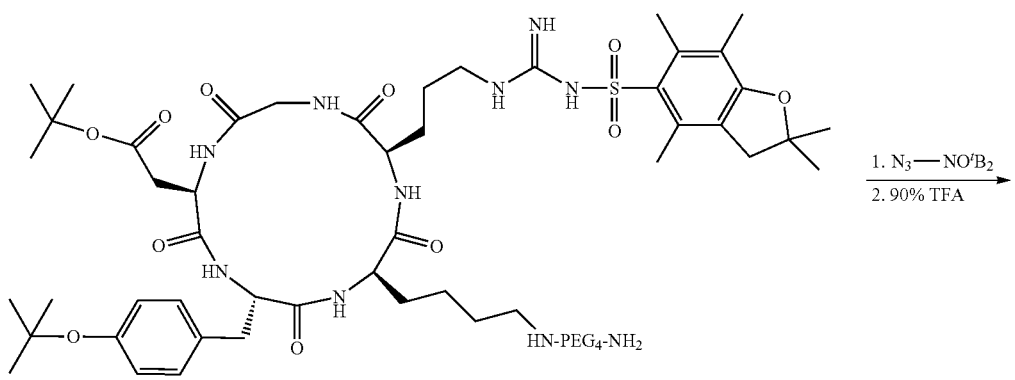

Pretected c(RGDyK)

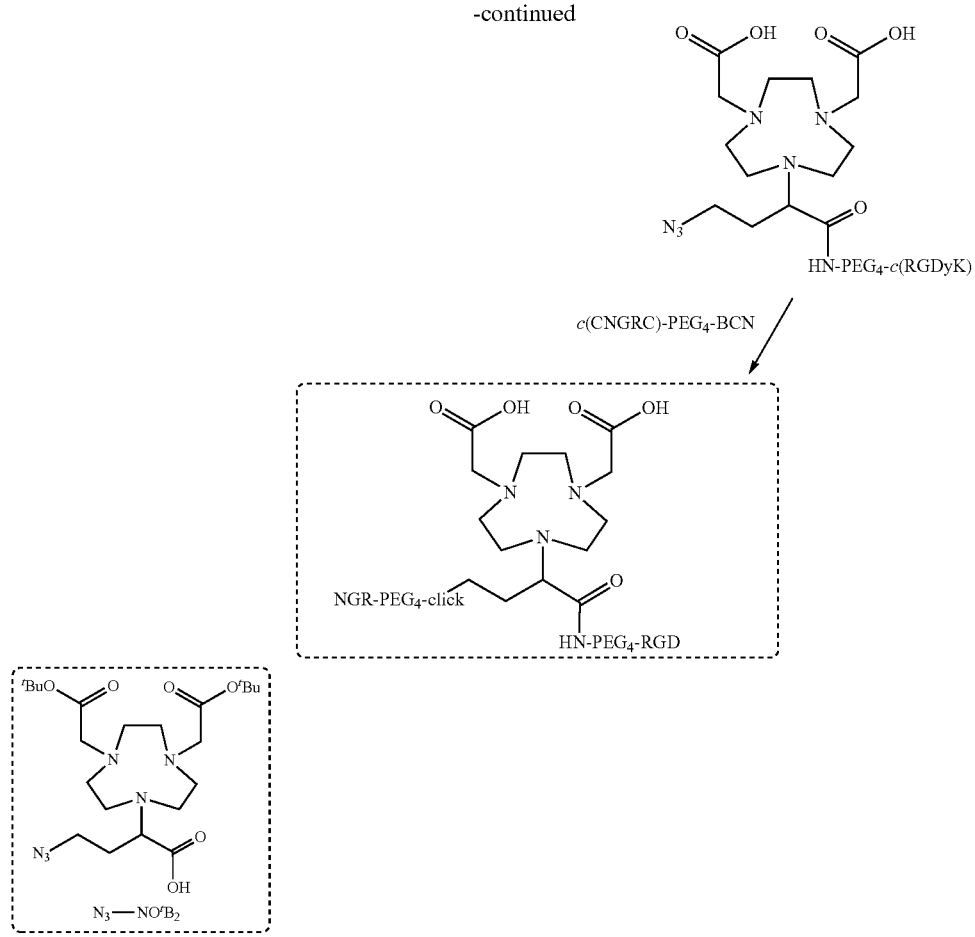

Using the bifunctional chelator (BFC), $N_3$—$NO^tB_2$ was conjugated to the fully protected c(RGDyK) via an amide formation reaction and then the protection group was removed in strong acid conditions. The resulting peptide was ligated to BCN-c(CNGRC) ("CNGRC" disclosed as SEQ ID NO: 1) via metal-free click reaction.

FIG. 1 depicts a dimer made with $N_3$—$NO^tB_2$-c(CN-GRC)-PEG4-NOTA-PEG4-RGD ("CNGRC" disclosed as SEQ ID NO: 1). The protected linear RGDyK was prepared via solid-phase synthesis (SPS), and then was cleaved from resin using 2% TFA in DCM. Cyclization of protected RGDyK was performed by treating with Diphenyl phosphoryl azide (DPPA). After ivDde on the lysine was deprotected, Fmoc-PEG$_4$-OH was attached to the primary amine on the side chain of lysine, and then the Fmoc was deprotected using 20% piperidine in DMF. After HPLC purification, the resulting protected cyclo(RGDyK)-PEG$_4$-NH$_2$ was conjugated with the $N_3$—$NOtB_2$ using EDCI and DMAP. The purified cyclo(RGDyK)-PEG4-NOTA-N$_3$ was ligated with cyclo(CNGRC)-PEG$_4$-BCN ("CNGRC" disclosed as SEQ ID NO: 1) (prepared by mixing BCN-PEG$_4$-NHS with cyclo(CNGRC) ("CNGRC" disclosed as SEQ ID NO: 1) in pH~8.5 PBS buffer) via strain-promoted alkyne-azide cycloaddition (SPAAC) between N$_3$ and BCN moieties.

Rendered by the triazole formation after metal-free click reaction, the purified heterodimers (NGR-NOTA-RGD) were successfully labeled with $^{64}Cu$, $^{68}Ga$, and $Al^{18}F$ at 37° C., 70° C., and 90° C., respectively. Labeling results were monitored by the radio HPLC. Labeling yields were above 90% for $^{64}Cu$ and $^{68}Ga$, close to 50% for $Al^8F$.

Example 9: PET Imaging Using the c(cNGRc)-c(RGDyK) Heterodimer in the Subcutaneous Xenograft Mouse Model In vivo PET/CT imaging was conducted in NCr nude mice bearing bxpc3 (human pancreatic adenocarcinoma cell line) and 4T1 (a murine breast cancer cell line that overexpresses integrin $\alpha_v\beta3$ and CD13) tumor xenografts.

Mice were injected with bxpc3 cells (1 million cells in 150 μL PBS) into the subcutaneous flank of the right shoulder and 4T1 cells (1 million cells in 150 μL PBS) into the subcutaneous flank of the left shoulder. Either the CNGRC-($^{68}Ga$)NOTA-RGDyK heterodimer ("CNGRC" disclosed as SEQ ID NO: 1), ($^{68}Ga$)NOTA(CNGRC) ("CN-GRC" disclosed as SEQ ID NO: 1), or ($^{68}Ga$)NOTA (RGDyK) were injected into the bloodstream via tail vein injection. Blocking studies were conducted for the heterodimer studies by co-injecting 100 times of cyclo(CNGRC) ("CNGRC" disclosed as SEQ ID NO: 1) and cyclo (RGDyK). Small animal PET/CT was performed at 1 hour post injection of tracers (FIG. 14). The heterodimer CNGRC-($^{68}Ga$)NOTA-RGDyK ("CNGRC" disclosed as SEQ ID NO: 1) showed improved enhanced in in vivo performance (such as longer blood retention, better tumor/non-tumor ratios).

Example 10: PET Imaging Using the c(cNGRc)-c(RGDyK) Heterodimer in the Orthotopic Xenograft Mouse Model In vivo PET/CT imaging was conducted in Balb/c mice. One week after the orthotropic implantation of $1 \times 10^6$ luciferase-transfected KPCP cancer cells into the pancreas of Balb/c mice, the mice were used for PET imaging. Either the CNGRC-($^{68}$Ga)NOTA-RGDyK heterodimer ("CNGRC" disclosed as SEQ ID NO: 1), ($^{68}$Ga)NOTA(CNGRC) ("CNGRC" disclosed as SEQ ID NO: 1), or ($^{68}$Ga)NOTA (RGDyK)] were injected into the bloodstream via tail vein injection. Blocking studies were conducted for the heterodimer studies by co-injecting 100× of CNGRC (SEQ ID NO: 1) and RGDyK. Small animal PET/CT was performed at 1 hour post injection of tracers (FIGS. 15A-15C). The heterodimer CNGRC-($^{68}$Ga)NOTA-RGDyK ("CNGRC" disclosed as SEQ ID NO: 1) showed improved in in vivo performance (such as longer blood retention, better tumor/non-tumor ratios) (FIG. 15A). Uptakes of the RGD-NGR heterodimer in muscle, blood, liver, spleen, kidney, pancrease, and orthotopic tumor were 0.10% ID/g, 0.10% ID/g, 1.8% ID/g, 1.10% ID/g, 2.2% ID/g, 0.36% ID/g, and 1.4% ID/g, respectively.

Example 11: PET Imaging Using the c(cNGRc)-c(RGDyK) Heterodimer in the Spontaneous Transgenic Mouse Model In vivo PET/CT imaging was conducted in the genetically engineered KCH (Pdx1-Cre;K-RasG12D/+; HMGB1−/−) mouse model. High mobility group box 1 (HMGB1) is a critical regulator of autophagy, a major pathway for degradation of effete proteins and damaged organelles, and the conditional genetic ablation of HMGB1 limited to the pancreas inhibits autophagy, promotes proliferation, activates normally quiescent pathways, and renders mice extraordinarily sensitive to K-RasG12D/+-driven pancreatic carcinogenesis. The progression of PanINs from low grade PanIN1 to high grade PanIN3 could be observed as early as seven days (normally three-nine months) after birth in KCH (Pdx1-Cre;K-RasG12D/+;HMGB1−/−). PET imaging normally was performed~6 weeks old KCH mice.

Either the CNGRC-($^{68}$Ga)NOTA-RGDyK ("CNGRC" disclosed as SEQ ID NO: 1) heterodimer, ($^{68}$Ga)NOTA (CNGRC) ("CNGRC" disclosed as SEQ ID NO: 1), or ($^{68}$Ga)NOTA(RGDyK)] were injected into the bloodstream via tail vein injection. Blocking studies were conducted for the heterodimer studies by co-injecting 100× of CNGRC (SEQ ID NO: 1) and RGDyK. Small animal PET/CT was performed at 1 hour post injection of tracers (FIGS. 16A-16D). The heterodimer CNGRC-($^{68}$Ga)NOTA-RGDyK ("CNGRC" disclosed as SEQ ID NO: 1) showed improved in vivo performance (such as longer blood retention, better tumor/non-tumor ratios) (FIG. 16A). Uptakes of the RGD-NGR heterodimer in muscle, blood, liver, spleen, kidney, and malignant pancreas were 0.38% ID/g, 0.23% ID/g, 4.7% ID/g, 3.1% ID/g, 5.0% ID/g, and 5.9% ID/g, respectively.

In addition, as compared to the clinically widely-used $^{18}$F-FDG, which did not show any specific tumor uptake in the spontaneous transgenic mouse model (FIG. 16B), the heterodimer CNGRC-($^{68}$Ga)NOTA-RGDyK ("CNGRC" disclosed as SEQ ID NO: 1) showed specific tumor uptake and good tumor/non-tumor ratios (FIG. 16A).

Example 12: In Vitro High-Throughput Screening Platform

In a proof of concept study, a platform for screening different lengths of PEG spacers (PEG4, 8, 12 and 16) between RGD and AE105 was developed for the heterodimer targeting to avowal and uPAR. Results showed that PEG12 was the best spacer, which was validated by the in vivo PET imaging.

Preparation of chemicals for the above optimization are outlined in FIG. 3 (RGD and AE105 are peptides targeting to biomarker $\alpha_v\beta_3$ and uPAR, respectively):
1) Ten $NH_2$—$PEG_n$-RGD peptides containing spacers of various PEG lengths (n=2, 4, 6, 8, 10, 12, 14, 16, 18, 20) can be prepared by adding the corresponding Boc-$PEG_n$-NHS to RGD in a PBS buffer (pH=8.2), followed by Boc deprotection with 95% TFA. Then, the prepared NH2-$PEG_n$-RGD is mixed with photo-ODIBO-NHS in a PBS buffer (pH=8.2) to produce photo-OIDBO-$PEG_n$-RGD (abbreviated to p-ODIBO in FIG. 3).
2) N3-PEG4-AE105 can be prepared by mixing AE105 with N3-PEG4-NHS in a PBS buffer (pH=8.2).

In Vitro Optimization Procedures:
1) N3-PEG4-AE105 will be mixed with one of the ten photo-ODIBO-$PEG_n$-RGD peptides (n=2, 4, 6, 8, 10, 12, 14, 16, 18, 20) in a 1:1 molar ratio to prepare ten mixed-targeting molecule stock solutions;
2) One of the ten mixed-targeting molecule stock solutions will be added into a well in 96-well plate that is pre-seeded with cells, (in total ten wells are needed for ten mixed-targeting molecule solution);
3) After the targeting molecules bind to the targeted receptors, the unbound targeting molecules will be washed off using a PBS buffer;
4) A UV lamp (365 nm) will be applied to deprotect the azide-inactive photo-ODIBO and generate azide-active "ODIBO", subsequently triggering ligation between the N3-PEG4-AE105 and ODIBO-$PEG_n$-RGD (both bind to biomarkers on the cells);
5) After being incubated for an additional 2-4 h, N3-($^{64}$Cu)NOTA will be added to react with the "excess" ODIBO-$PEG_n$-RGD (that binds to cancer cells, but does not react to N3-PEG4-AE105);
6) The excess N3-($^{64}$Cu)NOTA will be washed off using a PBS buffer; and N3-(64Cu)NOTA can be retained on cells only after it ligates to the "excess" ODIBO-$PEG_n$-RGD.
7) The 96-well plate will be then be loaded into a high-throughput MicroBeta2 Plate Counter to measure the N3-($^{64}$Cu)NOTA ligated to "excess" ODIBO-$PEG_n$-RGD on cells.

The well with the lowest radio-counts, containing the lowest "excess" ODIBO, should get the highest amount of ligation product (between AE105-PEG4-N3 and ODIBO-$PEG_n$-RGD), thus the corresponding spacers are of an appropriate length.

Example 13: High-Throughput Screening Platform for Heterodimer Spacer Optimization A high throughput cell-based universal platform for rapid heterodimer spacer optimization has been developed to generate heterodimers with high avidity effects. By using the developed platform, the repetition of the traditional approach, which requires repeated synthesis and evaluation of a heterodimer library, is avoided. The platform can screen heterodimers with various spacers to identify a heterodimer with the best performance in in vitro and/or in vivo evaluations.

Methodology

Two ligands of interest, RGD (targeting to integrin $\alpha_v\beta_3$) and AE105 (targeting to urokinase-type plasminogen activator receptor (uPAR)), were functionalized with a photo ODIBO group and $N_3$ group, respectively, for the in-situ formation of a heterodimer. Herein, the photo-ODIBO group is a photo-triggered metal-free click chemistry moiety, which can be deprotected to ODIBO and react with azide via the strain-promoted alkyne-azide cycloadditions (SPAAC) upon UV 365 nm irradiation. To offer the capability of high-throughput screening and facilitate its application in research groups, the preparation of chemical tools was designed to avoid complex purifications (see FIG. 23). In particular, photo-ODIBO-PEG$_4$-RGD was prepared via treating RGD dissolved in DMSO with 6 eqv. DIEA and 3 eqv. ODIBO-PEG$_4$-NHS. After the pegylation was completed, 1×PBS was added to the reaction mixture so that the excess photo-ODIBO-PEG4-NHS could be hydrolyzed to non-cell reactive photo-ODIBO-PEG$_4$-COOH. Parallel synthesis of four N$_3$ functionalized AE105 analogues with different spacers was conducted via in a similar way via incubating AE105 with N$_3$-PEG$_n$-NHS (one of the four selected PEG spacers for each analogue), followed by hydrolyzing excess NHS with 1×PBS. Without further purification, the resulting photo-ODIBO-PEG$_4$-RGD and four N$_3$-PEG$_{Pn}$-AE105 solutions could be directly applied in the following heterodimer spacer optimization experiments.

Spacer optimization was performed as illustrated in FIG. 17: the photo-ODIBO-PEG$_4$-RGD and one of the N$_3$-PEG$_n$-AE105 prepared above were mixed and then added into a 96-well plate that pre-seeded with u87MG cells (a human brain cancer cell line which over expressed both integrin α$_v$β3 receptor and uPAR). Those cells were pre-fixed with 4% paraformaldehyde to minimize the internalization. After a 2 h incubation to allow sufficient binding of RGD and AE105 to integrin α$_v$β3 and uPAR respectively, the excess (unbound) ligands were washed off using PBS buffer. Then the plate was irradiated with a UV lamp (365 nm) for 2 minutes to deprotect the azide-inactive photo-ODIBO to the azide-active "ODIBO", triggering the metal-free click reaction between the N$_3$-PEG$_n$-AE105 and the ODIBO-PEG$_4$-RGD. After being incubated for an additional 2 h to allow the completion of the metal-free click reactions, ($^{64}$Cu) NOTA-N$_3$ was added as a radio scavenger to click with the "excess" ODIBO-PEG$_4$-RGD (that binds to cells, but did not click with N$_3$-PEG$_n$-AE105). Upon the removal of unbound ($^{64}$Cu)NOTA-N$_3$, the ($^{64}$Cu)NOTA-N$_3$ clicked to ODIBO-PEG$_n$-RGD was measured on MicroBeta2 Plate Counter. One group without UV irradiation was used as a background control to get counts resulting from the non-specific binding of ($^{64}$Cu)NOTA-N$_3$. After subtracting the background counts due to the non-specific binding, the well with the lowest radioactivity counts contained the least amount of ($^{64}$Cu)NOTA-click-PEG$_4$-RGDso as the highest amount of the in situ generated heterodimer (AE105-PEG$_n$-click-PEG$_4$-RGD), indicating the corresponding spacer length (PEG$_n$+4) will be the most suitable for achieving high avidity.

Compared with the traditional strategy, this platform avoided the abundant synthesis and evaluation of a heterodimer library consisting of heterodimers bearing varied spacers. In addition, owning to the high sensitivity of the beta counter, ligands were consumed at a nanomole scale for each test so that the cost of expensive starting materials was significantly reduced. Taking into account advantages of convenience, sensitivity, and capability on high throughput screening, this universal rapid spacer optimization platform can greatly facilitate the development of heterodimeric pharmaceuticals for research and/or clinical applications.

Results and Discussion

Firstly, the distance between one integrin α$_v$β3 receptor and one uPAR on a cell surface was estimated to select spacers of proper length for screening, and it was found that the possible distance between two receptors could be 5 nm or less. Given that the length of a single bond was around 1.5 Å (0.15 nm), the length of a PEG$_4$ unit consisting of 12 single bonds would be around 1.2 nm, when taking the bond angle into account. Therefore, to cover the length from 1 nm to 5 nm, 4 spacers consisting of PEG$_4$, PEG$_8$, PEG$_{12}$, and PEG$_{16}$ were selected for the screening purpose (see Table 2).

TABLE 2

| | Spacers selected for in vitro screening | | | |
|---|---|---|---|---|
| entrance | PEG units attached to RGD | PEG units attached to AE105 | Total PEG units | Estimated length (nm) |
| 1 | 4 | 0 | 4 | 1.2 |
| 2 | 4 | 4 | 8 | 2.4 |
| 3 | 4 | 8 | 12 | 3.6 |
| 4 | 4 | 12 | 16 | 4.8 |

Then RGD-PEG4-photo-ODIBO and AE105-PEG$_n$-N$_3$ (n=0, 4, 8, and 12) were prepared as shown in FIG. 23. Due to the use of 3 eqv. R-PEG-NHS ester, conversion yields of peptidic ligands reached above 95% within 30 minutes, as monitored by HPLC. FIG. 18 shows an example of converting RGD into RGD-PEG4-photo-ODIBO, in which RGD, RGD-PEG$_4$-photo-ODIBO, photo-ODIBO-PEG$_4$-COOH, and photo-ODIBO-PEG$_4$-NHS were eluted at 13, 19, 20, and 21 minutes respectively. In FIG. 18, the HPLC conditions were as follows: 0-2 minutes, 100% H$_2$O; 2-12 minutes, changing from 100% H$_2$O to 80% H$_2$O and 20% ACN; 12-22 minutes, changing from 80% H$_2$O and 20% ACN to 10% H$_2$O and 90% ACN; 22-26 minutes, 10% H$_2$O and 90% ACN; 26-27 minutes changing from 10% H$_2$O and 90% ACN to 100% H$_2$O; 27-35 minutes, 100% H$_2$O with a flow rate of 1.5 ml/min. Based on the quantitative results obtained from the HPLC spectra, after the reaction mixture was stirred for 0.5 h at room temperature, the RGD conversion yield was above 95%, and less than 5% photo-ODIBO-PEG$_4$-NHS was hydrolyzed to photo-ODIBO-PEG$_4$-COOH.

After the addition of 1×PBS, the reaction mixture was allowed to stand overnight to maximize hydrolysis of photo-ODIBO-PEG$_4$-NHS, and only RGD-PEG$_4$-photo-ODIBO as well as photo-ODIBO-PEG$_4$-COOH remained in the reaction mixture. Similar observations were obtained when the AE105-PEG$_n$-N$_3$ (n=0, 4, 8, and 12) was prepared. Because neither photo-ODIBO-PEG$_4$-COOH nor N$_3$-PEG$_n$-COOH would bind to cells due to the lack of a targeting ligand, they were washed away together with unbound RGD-PEG$_4$-photo-ODIBO or AE105-PEG$_n$-N$_3$. Therefore, the resulting five reaction mixtures can be directly applied in the cell based screening without further purification.

Subsequently, the RGD-PEG$_4$-photo-ODIBO was parallelly mixed with either AE105-PEG$_0$-N$_3$ or AE105-PEG$_4$-N$_3$ or AE105-PEG$_8$-N$_3$ or AE105-PEG$_{12}$-N$_3$, resulting in four groups of stock solutions each containing both RGD-PEG$_4$-photo-ODIBO and one of the AE105-PEG$_n$-N$_3$ (n=0, 4, 8, 12). As illustrated in FIG. 17, the four groups of stock solutions were applied in the designed cell based screening assay using u87MG cells pre-fixed with 4% paraformaldehyde. In addition to the four experimental groups, a negative control group was prepared in which cells were treated with RGD-PEG4-photo-ODIBO and NH$_2$—PEG$_0$-AE105; thus, no heterodimer could be generated in this negative control group as there was no ligation between ODIBO and NH$_2$. Additionally, there was a background control group, in which no UV irradiation was applied; thus, the amount of ($^{64}$Cu)NOTA-N$_3$ detected was caused by its non-specific binding on cells. After subtracting the non-specific binding recorded in the background control group, the specific bindings of ($^{64}$Cu)NOTA-N$_3$ in different groups caused by its ligation with the RGD-PEG$_4$-ODIBO were compared. As shown in FIG. 19, the groups treated with N$_3$-PEG$_4$-AE105 and N$_3$—PEG$_8$-AE105 exhibited less amount of the specific binding of ($^{64}$Cu)NOTA-N$_3$, suggesting that RGD-PEG$_8$-

AE105 and RGD-PEG$_{12}$-AE105 were the two most abundant heterodimers formed on u87MG cells. Accordingly, the two corresponding spacers (entrance 2 & 3) were the most potent among the four tested spacers.

Finally, the result obtained from the above screening assay was validated both in vitro and in vivo. The four RGD-AE105 heterodimers possessing various PEG spacers (PEG$_4$, PEG$_8$, PEG$_{12}$ and PEG$_{16}$, respectively) were prepared as described in the previous examples. The prepared heterodimers were then radiolabeled with either Cu-64 or Ga-68 for in vitro and in vivo evaluation respectively. Based on the cell uptake result as shown in FIG. 20A, the PEG$_{16}$-containing heterodimer exhibited the highest cell uptake, followed by the PEG$_{12}$-, PEG$_8$-, and PEG$_4$-contained heterodimers with 4 h uptake values of 0.46%, 0.38%, 0.24% and 0.16% respectively. In the cell efflux study (FIG. 20B), the PEG$_8$ and PEG$_{12}$-containing heterodimers showed the best cell retention, followed by the PEG$_4$-, and PEG$_{16}$-containing heterodimers with 2 h retention values of 44%, 43%, 35% and 26%, respectively. Taking into account both the cell uptake and efflux results among the four tested heterodimers, the PEG$_{12}$-containing heterodimer demonstrated the highest potential in this in vitro evaluation, consistant with the result obtained from the designed cell based screening assay.

Further in vivo validation was conducted by comparing PET imaging results obtained from mice bearing u87MG xenografts. As shown in FIG. 21, tumors could be visualized by using all the four tested heterodimeric PET tracers while the PEG$_{12}$-contained heterodimer exhibited the highest tumor to background contrast, followed by the PEG$_8$-, PEG$_{16}$-, and PEG$_4$-containing heterodimers. Quantitative tumor uptake values were subsequently revealed by the region of interest (ROI) analysis (FIG. 22). The tumor uptake value of the PEG$_{12}$-containing heterodimer was 2.8%, while those of PEG$_8$-, PEG$_{16}$-, and PEG$_4$-containing heterodimers were 2.4%, 2.1% and 1.7%, respectively, reaffirming the result obtained from the designed cell based screening assay. Collectively, results from both in vitro and in vivo evaluations successfully validated the accuracy and reliability of the rapid spacer-optimization platform. The selected AE105-PEG$_{12}$-RGD was further compared with two corresponding monomer AE105 and RGD via PET imaging of u87MG xenografts on nude mice. Superior imaging results were obtained in mice administrated with the heterodimer, indicating its better in vivo performance than the two monomer counterparts due to the avidity effects.

Thus, using a photo-triggered metal-free click reaction, a universal in vitro screening platform can be established for simplifying the spacer optimization process involved in developing high avidity heterodimers, which can be broadly applied to various dual-biomarker combinations and different diseases. The developed screening platform was successfully applied in the spacer optimization of the integrin αvo$_3$-uPAR dual-targeted heterodimeric ligand. The accuracy and reliability of this platform was further validated via both in vitro and in vivo evaluations, in which heterodimers containing all the tested spacers were prepared and evaluated individually. In addition to the demonstrated capability of high throughput screening (as shown in FIG. 17), this universal platform can significantly accelerate and/or enhance the application of the dual-receptor-targeting strategy in various biomedical fields, particularly when targeted receptors are expressed in low abundance and/or when high affinity (and/or specificity) monovalent ligands are not available.

Example 14: Exploring Spacer Lengths

Eight NH$_2$—PEG$_n$-RGD peptides containing spacers of various PEG lengths (n=2, 4, 6, 8, 10, 12, 14, 16) will be prepared by adding the corresponding Boc-PEG$_n$-NHS to RGD in a PBS buffer (pH=8.2), followed by Boc deprotection. Photo-ODIBO-NHS, prepared using previously reported procedures, will then be mixed with the prepared NH$_2$—PEG$_n$-RGD in a PBS buffer (pH=8.2) to produce photo-OIDBO-PEG$_n$-RGD. N$_3$-PEG$_4$-cetuximab will be prepared using previously reported procedures. N$_3$—PEG$_4$-cetuximab and the eight photo-ODIBO-PEG$_n$-RGD peptides (n=2, 4, 6, 8, 10, 12, 14, 16) will be used for in vitro screening (at 4° C. to minimize the internalization of targeting probes). As shown in FIG. 11: 1): eight mixed-ligands stock solutions will be prepared by mixing N$_3$-PEG$_4$-cetuximab with one of the eight photo-OIDBO-PEG$_n$-RGD peptides; 2) U87MG cells will be cultured in a 96-well plate; 3) one of the above eight mixed-ligands stock solution will be added into each well (eight wells in total) pre-seeded with U87MG; 2) after the ligands bind to the targeted receptors, the excess (unbound) targeting ligands will be washed off using a PBS buffer (repeated 5 times to ensure complete removal); 3) a UV lamp (365 nm) will be applied to deprotect the azide-inactive photo-ODIBO and generate azide-active "ODIBO", subsequently triggering ligation between the N$_3$-PEG$_4$-cetuximab and ODIBO-PEG$_n$-RGD; 4) after being incubated for an additional 2 h, $^{64}$Cu-labeled N$_3$—NOTA will be added to click with the "excess" ODIBO-PEG$_n$-RGD (that binds to cells, but does not click to N$_3$-PEG$_4$-cetuximab); and 5) the excess N$_3$-($^{64}$Cu)NOTA will be removed, and the N$_3$-($^{64}$Cu)NOTA clicked to "excess" ODIBO-PEG$_n$-RGD will be measured on Micro-Beta2 Plate Counter. One group without UV irradiation will be used as a negative control to get counts from the non-specific binding of N$_3$-($^{64}$Cu)NOTA. After subtracting the non-specific binding, the specific binding of N$_3$-($^{64}$Cu)NOTA obtained from the eight ODIBO-PEG$_n$-RGD (n=2, 4, 6, 8, 10, 12, 14, 16) will be compared. The well with the lowest specific binding will contain the highest amount of clicking product (between cetuximab-PEG$_4$-N$_3$ and ODIBO-PEG$_n$-RGD), thus the corresponding spacer will be the most potent.

The ODIBO-PEG$_n$-RGD containing the most potent PEG spacer will click with Tz-NOTA-N$_3$ and then be radiolabeled with $^{64}$Cu, and the resulting Tz-($^{64}$Cu)NOTA-PEG$_n$-RGD will be used for the in vitro avidity studies on U87MG cells. Tz-($^{64}$Cu)NOTA-RGD (without a PEG spacer) will be used as a negative control because the distance between RGD and cetuximab in the resulting heterodimer is too short to achieve avidity effect (proved in preliminary study, FIG. 5B). Briefly, Tz-($^{64}$Cu)NOTA-PEG$_n$-RGD/TCO-PEG$_4$-cetuximab ligation product (cetuximab-PEG$_4$-($^{64}$Cu)NOTA-PEG$_n$-RGD) will be used for cell uptake/efflux, binding affinity and Bmax measurements on U87MG cells. After high avidity effect is confirmed on the above ligation product, in vivo evaluation will be performed then. Mice bearing U87MG xenografts will be pre-injected with 100 μg of TCOPEG$_4$-cetuximab, and 24 h later, ~250-350 pCi of Tz-($^{64}$Cu)NOTA-PEG$_n$-RGD (or Tz-($^{64}$Cu)NOTA-RGD in the negative control group) will be injected. Then 1 h dynamic PET scans will be performed at multiple time points (p.i., 4, 18, and/or 28 h). As cetuximab is cleared through the liver, kinetics on tumor and liver at mid and late time points can be evaluated. At mid/late time points (4, 18, 28 h) when most of the un-ligated Tz-($^{64}$Cu)NOTAPEGn-RGD has been washed off, observation of relatively slower tumor washing out and faster liver clearing (compared to that from Tz-($^{64}$Cu)NOTA-RGD) can indicate the much stronger binding with tumor cells, and thus an avidity effect of in vivo ligation product (cetuximab-PEG$_2$-($^{64}$Cu)NOTA-PEG$_n$-RGD) is being achieved.

Various references are cited in this document, which are hereby incorporated by reference in their entireties herein.

What is claimed is:

1. A compound for molecular imaging or therapy comprising:

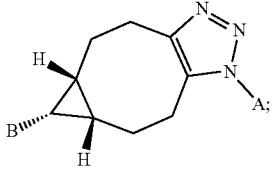

wherein A comprises a first peptide and a chelator;
wherein B comprises a second peptide;
wherein the chelator comprises a chelating core selected from the group consisting of NOTA, NETA, CB-TE2A, CB-TE1A1P, TETA, Pycu2A, DiAmSar, DOTA, DTPA, PCTA, and DFO; and
wherein the first and the second peptide are independently selected from the group consisting of NGR, LLP2A, BBN(7-14), Tyr(3)-octreotate, DAPTA, RGD c(cNGRc), c(RGDyK), and RAD.

2. The compound of claim 1, further comprising a detectable label, wherein the detectable label is selected from the group consisting of $^{110}$In, $^{111}$In, $^{177}$Lu, $^{52}$Fe, $^{62}$Cu, $^{64}$Cu, $^{32}$P, $^{11}$C, $^{13}$N, $^{15}$O, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{186}$Re, $^{188}$Re, $^{51}$Mn, $^{52m}$Mn, $^{55}$Co, $^{72}$As, $^{75}$Br, $^{76}$Br, $^{82m}$Rb, and $^{83}$Sr.

3. The compound of claim 1, further comprising a detectable label, wherein the detectable label is a dye molecule.

4. The compound of claim 3, wherein the dye molecule is selected from the group consisting of Cy3, Cy3.5, Cy5, Cy7, Cy5.5, Cy7.5, GFP, Calcein, FITC, FluorX, Alexa dye, Rhodamine dye, 5-FAM, Oregon Green, and Texas Red.

5. The compound of claim 1, wherein A and B further comprise a spacer.

6. The compound of claim 5, wherein the spacer comprises polyethylene glycol.

7. The compound of claim 1, wherein the first and second peptides are a RGD sequence and a NGR sequence, respectively.

8. The compound of claim 1, wherein the first and second peptides are c(cNGRc) and c(RGDyK), respectively.

* * * * *